US009277737B2

(12) United States Patent
Demuth et al.

(10) Patent No.: US 9,277,737 B2
(45) Date of Patent: *Mar. 8, 2016

(54) MOUSE MODELS CARRYING A KNOCK-OUT MUTATION OF THE QPCTL-GENE

(71) Applicant: Probiodrug AG, Halle/Saale (DE)

(72) Inventors: Hans-Ulrich Demuth, Halle/Saale (DE); Anett Stephan, Halle/Saale (DE); Birgit Koch, Amsdorf (DE); Holger Cynis, Halle/Saale (DE); Stephan Schilling, Halle/Saale (DE); Reinhard Sedlmeier, Munich (DE); Sigrid Graubner, Munich (DE)

(73) Assignee: PROBIODRUG AG, Halle/Saale (DE)

( * ) Notice: Subject to any disclaimer, the term of this patent is extended or adjusted under 35 U.S.C. 154(b) by 0 days.

This patent is subject to a terminal disclaimer.

(21) Appl. No.: 13/888,239

(22) Filed: May 6, 2013

(65) Prior Publication Data

US 2013/0291133 A1    Oct. 31, 2013

Related U.S. Application Data

(60) Continuation-in-part of application No. 13/325,015, filed on Dec. 13, 2011, now Pat. No. 8,647,834, which is a continuation of application No. 12/497,082, filed on Jul. 2, 2009, now Pat. No. 8,129,160, which is a division of application No. 11/859,217, filed on Sep. 21, 2007, now abandoned, application No. 13/888,239, which is a continuation-in-part of application No. 12/782,953, filed on May 19, 2010, now abandoned.

(60) Provisional application No. 60/846,244, filed on Sep. 21, 2006, provisional application No. 60/947,780, filed on Jul. 3, 2007, provisional application No. 61/179,423, filed on May 19, 2009.

(51) Int. Cl.
*A01K 67/027* (2006.01)
*C12N 9/00* (2006.01)
*C12N 9/10* (2006.01)

(52) U.S. Cl.
CPC ............ *A01K 67/0276* (2013.01); *C12N 9/104* (2013.01)

(58) Field of Classification Search
None
See application file for complete search history.

(56) References Cited

U.S. PATENT DOCUMENTS

| | | | |
|---|---|---|---|
| 4,873,191 A | 10/1989 | Wagner et al. | |
| 4,873,316 A | 10/1989 | Meade et al. | |
| 5,175,384 A | 12/1992 | Krimpenfort et al. | |
| 5,602,299 A | 2/1997 | Lazzarini | |
| 5,981,830 A | 11/1999 | Wu et al. | |
| 6,037,521 A | 3/2000 | Sato et al. | |
| 6,066,778 A | 5/2000 | Ginsburg et al. | |
| 7,304,086 B2 | 12/2007 | Schilling et al. | |
| 7,371,871 B2 | 5/2008 | Schilling et al. | |
| 7,381,537 B2 | 6/2008 | Demuth et al. | |
| 7,462,599 B2 | 12/2008 | Schilling et al. | |
| 8,129,160 B2 * | 3/2012 | Schilling et al. | 435/183 |
| 8,647,834 B2 * | 2/2014 | Schilling et al. | 435/7.8 |
| 2002/0194632 A1 | 12/2002 | McConlogue et al. | |
| 2004/0006011 A1 | 1/2004 | Gour et al. | |
| 2004/0224875 A1 | 11/2004 | Schilling et al. | |
| 2005/0137142 A1 | 6/2005 | Schultz et al. | |
| 2005/0171112 A1 | 8/2005 | Schultz et al. | |
| 2006/0100253 A1 | 5/2006 | Niestroj et al. | |
| 2007/0079389 A1 | 4/2007 | Noda et al. | |
| 2007/0191366 A1 | 8/2007 | Hoffman et al. | |
| 2008/0153892 A1 | 6/2008 | Schilling et al. | |
| 2008/0249083 A1 | 10/2008 | Schilling et al. | |
| 2008/0260688 A1 | 10/2008 | Buchholz et al. | |
| 2008/0286810 A1 | 11/2008 | Demuth et al. | |
| 2009/0018087 A1 | 1/2009 | Schilling et al. | |
| 2009/0068699 A1 | 3/2009 | Schilling et al. | |
| 2009/0098052 A1 | 4/2009 | Schilling et al. | |
| 2009/0149394 A1 | 6/2009 | Schilling et al. | |

FOREIGN PATENT DOCUMENTS

| | | |
|---|---|---|
| DE | 293584 | 5/1991 |
| EP | 264166 | 4/1986 |
| EP | 1262552 | 4/2002 |
| WO | WO 90/08832 | 9/1990 |
| WO | WO 01/09090 | 2/2001 |
| WO | WO 01/53331 | 7/2001 |
| WO | WO 2003/045321 | 6/2003 |
| WO | WO 2004/098591 | 11/2004 |
| WO | WO 2004/098625 | 11/2004 |
| WO | WO 2005/039548 | 5/2005 |
| WO | WO 2005/049025 | 6/2005 |
| WO | WO 2005/075436 | 8/2005 |
| WO | WO 2008/034891 | 3/2008 |

(Continued)

OTHER PUBLICATIONS

Chica et al. Curr Opin Biotechnol. Aug. 2005;16(4):378-84.*
Sen et al. Appl Biochem Biotechnol. Dec. 2007;143(3):212-23.*
Banerji et al., A Lymphocyte-Specific Cellular Enhancer is Located Downstream of the Joining Region in Immunoglobulin Heavy Chain Genes, Cell, 1983, pp. 729-740, vol. 33.
Bateman et al., Evidence for Essential Histidines in Human Pituitary Glutaminyl Cyclase, Biochemistry, 2001, pp. 11246-11250, vol. 40.
Bhatia et al., Treatment with Bindarit, a Blocker of MCP-1 Synthesis, Protects Mice Against Acute Pancreatitis, Am J Physiol Gastrointest. Liver Physiol, 2005, pp. G1259-1265, vol. 288.

(Continued)

*Primary Examiner* — Christian Fronda
(74) *Attorney, Agent, or Firm* — Dentons US LLP

(57) ABSTRACT

A knock-out non-human animal, in particular a mouse, carrying a QPCTL knock-out mutation. Additionally, respective cells and cell lines and methods and compositions for evaluating agents that affect QPCTL, for use in compositions for the treatment of QPCTL-related diseases are disclosed.

19 Claims, 32 Drawing Sheets

(56) References Cited

FOREIGN PATENT DOCUMENTS

| WO | WO2008034891 | * | 3/2008 |
|---|---|---|---|
| WO | WO 2008/087197 | | 7/2008 |

OTHER PUBLICATIONS

Binder et al., The Role of Neurotensin in the Pathophysiology of Schizophrenia and the Mechanism of Action of Antipsychotic Drugs, Society of the Biological Psychiatry, 2001, pp. 856-872, vol. 50.

Bockers et al., Glutaminyl-Cyclase Expression in the Bovine/Porcine Hypothalamus and Pituitary, Journal of Neuroendocrinology, 1995, pp. 445-453, vol. 7.

Booth et al., Human Glutaminyl Cyclase and Bacterial Zinc Aminopeptidase Share a Common Fold and Active Site, BMC Biology, 2004, 9 pages.

Borchelt et al., Familial Alzheimer's Disease-Linked Presenilin 1 Variants Elevate Aβ1-42/1-40 Ratio in Vitro and in Vivo, Neuron, 1996, pp. 1005-1013, vol. 17.

Buchholz et al., The first potent inhibitors for human glutaminyl cyclase: Synthesis and structure-activity relationship, Journal of Medicinal Chemistry, 2006, pp. 664-677, vol. 49, No. 2.

Busby et al., An Enzyme(s) That Converts Glutaminyl-Peptides into Pyroglutamyl-Peptides, The Journal of Biological Chemistry, 1987, pp. 8532-8536, vol. 262, No. 18.

Byrne and Ruddle, Multiplex Gene Regulation: A Two-Tiered Approach to Transgene Regulation in Transgenic Mice, Proc. Natl. Acad. Sci., 1989, pp. 5473-5477, vol. 86.

Calame and Eaton, Transcriptional Controlling Elements in the Immunoglobulin and T Cell Receptor Loci, Advances in Immunology, 1988, pp. 235-275, vol. 43.

Casas et al., Massive CA1/2 Neuronal Loss with Intraneuronal and N-Terminal Truncated Aβ42 Accumulation in a Novel Alzheimer Transgenic Model, American Journal of Pathology, 2004, pp. 1289-1300, vol. 165, No. 4.

Ceballos-Picot et al., Neuronal-Specific Expression of Human Copper-Zinc Superoxide Dismutase Gene in Transgenic Mice: Animal Model of Gene Dosage Effects in Down's Syndrome Brain Research, 1991, pp. 198-214, vol. 552.

Chica et al., Semi-rational approaches to engineering enzyme activity: combining the benefits of directed evolution and rational design, Current Opinion Biotechnology, pp. 378-384, 2005, vol. 16, No. 4.

Citron et al., Mutant Presenilins of Alzheimer's Disease Increase Production of 42-Residue Amyloid β-Protein in Both Transfected Cells and Transgenic Mice, Nature Medicine, 1997, pp. 67-72, vol. 3, No. 1.

Cohen et al., The "Goldilocks Effect" in Cystic Fibrosis: identification of a lung phenotype in the cftr knockout and heterozygous mouse, BMC Genetics, 2004, pp. 1-6, vol. 5, No. 21.

Coll et al., HIV-Infected Patients with Lipodystrophy have Higher Rates of Carotid Atherosclerosis: The Role of Monocyte Chemoattractant Protein-1, Cytokine, 2006, pp. 51-55, vol. 34.

Comery et al., Acute γ-Secretase Inhibition Improves Contextual Fear Conditioning in the Tg2576 Mouse Model of Alzheimer's Disease, The Journal of Neuroscience, 2005, pp. 8898-8902, vol. 25, No. 39.

Consalvo et al., A Rapid Fluorometric Assay for N-Terminal Glutaminyl Cyclase Activity Using High-Performance Liquid Chromatography, Analytical Biochemistry, 1988, pp. 131-138, vol. 175.

Cynis et al., Isolation of an Isoenzyme of Human Glutaminyl Cyclase: Retention in the Golgi Complex Suggests Involvement in the Protein Maturation Machinery, J. Mol. Biol., 2008, pp. 966-980, vol. 379.

Cynis et al., Inhibition of Glutaminyl Cyclase Alters Pyroglutamate Formation in Mammalian Cells, Biochimica et Biopysica Acta, 2006, pp. 1618-1625.

Dahl et al., Caria Papaya Glutamine Cyclotransferase Belongs to a Novel Plant Enzyme Subfamily: Cloning and Characterization of the Recombinant Enzyme, Protein Expression and Purification, 2000, pp. 27-36, vol. 20.

Darnell et al., Molecular Cell Biology 2nd Edition, Scientific American Books, 1990, 63.

Edlund et al., Cell-Specific Expression of the Rat Insulin Gene: Evidence for Role of Two Distinct 5' Flanking Elements, Science, 1985, pp. 912-916, vol. 230.

El Moussaoui et al., Revisiting the Enzymes Stored in the Laticifers of Carica papaya in the context of their Possible-Participation in the Plant Defense Mechanism, Cell Mol Life Sci, 2001, pp. 556-570, vol. 58.

Faessler et al., Knockout Mice: How to Make Them and Why. The Immunological Approach, International Archives of Allergy and Immunology, 1995, pp. 323-334, vol. 106.

Fischer and Spiess, Identification of a Mammalian Glutaminyl Cyclase Converting Glutaminyl into Pyroglutamyl Peptides, Proc. Natl. Acad. Sci., 1987, pp. 3628-3632, vol. 84.

Forss-Petter et al., Transgenic Mice Expressing β-Galactosidase in Mature Neurons Under Neuron-Specific Enolase Promoter Control, Neuron, 1990, pp. 187-197, vol. 5.

Fraser et al., Fertilization Promoting Peptide—A Possible Regulator of Sperm Function in Vivo, Vitamins and Hormones, 2001, pp. 1-28, vol. 63.

Funato et al., Astrocytes Containing Amyloid β-Protein (Aβ)-Positive Granules Are Associated with Aβ40-Positive Diffuse Plaques in the Aged Human Brain, American Journal of Pathology, 1998, pp. 983-992, vol. 152, No. 4.

Garden et al., Formation of N-Pyroglutamyl Peptides from N-Glu and N-Gln Precursors in Aplysia Neurons, Journal of Neurochemistry, 1999, pp. 676-681, vol. 72.

Geddes et al., N-Terminus Truncated β-Amyloid Peptides and C-Terminus Truncated Secreted Forms of Amyloid Precursor Protein: Distinct Roles in the Pathogenesis of Alzheimer's Disease, Neurology of Aging, 1999, pp. 75-79, vol. 20.

Ghiso et al., Chromosome 13 Dementia Syndromes as Models of Neurodegeneration, Amyloid J. Protein Folding Disord, 2001, pp. 277-284,vol. 8.

Glenner et al., Alzheimer's Disease: Initial Report of the Purification and Characterization of a Novel Cerebrovascular Amyloid Protein, Biochemical and Biophysical Research Communications, 1984, pp. 885-890, vol. 120.

Golobov et al., Substrate and Inhibitor Specificity of Glutamine Cyclotransferase (QC), Biol Chem. Hoppe Seyler, 1996, pp. 395-398, vol. 377.

Gong et al., An Antagonist of Monocyte Chemoattractant Protein 1 (MCP-1) Inhibits Arthritis in the MRL-lpr Mouse Model, J. Exp. Med, 1997, pp. 131-137, vol. 186.

Gosling et al., MCP-1 Deficiency Reduces Susceptibility to Atherosclerosis in Mice that Overexpress Human Apolipoprotein B, The Journal of Clinical Investigation, 1999, pp. 773-778, vol. 103.

Gossen et al., Tight Control of Gene Expression in Mammalian Cells by Tetracycline-Responsive Promoters, Proc. Natl. Acad. Sci., 1992, pp. 5547-5551, vol. 89.

Gossen et al., Transcriptional Activation by Tetracyclines in Mammalian Cells, Science, 1995, pp. 1766-1769, vol. 268.

Gu et al., Absence of Monocyte Chemoattractant Protein-1 Reduces Atherosclerosis in Low Density Lipoprotein Receptor-Deficient Mice, Molecular Cell, 1998, pp. 275-281, vol. 2.

Guntert et al., High Sensitivity Analysis of Amyloid-Beta Peptide Composition in Amyloid Deposits from Human and Ps2App Mouse Brain, Neuroscience, 2006, pp. 461-475, vol. 143.

Haase et al., Cellular Processing of β-Amyloid Precursor Protein and the Genesis of Amyloid β-Peptides, Cell, 1993, pp. 1039-1042, vol. 75.

Harigaya et al., Amyloid β Protein Starting Pyroglutamate at Position 3 is a Major Component of the Amyloid Deposits in the Alzheimer's Disease Brain, Biochemical and Biophysical Research Communication, 2000, pp. 422-427, vol. 276.

Haskell et al., Efficient Production of Transgenic Cattle by Retroviral Infection of Early Embryos, Molecular Reproduction and Development, 1995, pp. 386-390, vol. 40.

He et al., The Aβ 3-Pyroglutamyl and 11-Pyroglutamyl Peptides Found in Senile Plaque Have Greater β-Sheet Forming and Aggregation Propensities In Vitro than Full-Length Aβ, Biochemistry, 1999, pp. 10871-10877, vol. 38.

(56) References Cited

OTHER PUBLICATIONS

Hemmerich et al., Identification of Residues in the Monocyte Chemotactic Protein-1 that Contact the MCP-1 Receptor, CCR2, Biochemistry, 1999, pp. 13013-13025, vol. 38, No. 40.
Hosoda et al., Quantification of Modified Amyloid β Peptides in Alzheimer Disease and Down Syndrome Brains, Journal of Neuropathology and Experimental Neurology, 1998, pp. 1089-1095, vol. 57.
Huse et al., β-Secretase Processing in the Trans-Golgi Network Preferentially Generates Truncated Amyloid Species That Accumulate in Alzheimer's Disease Brain, The Journal of Biological Chemistry, 2002, pp. 16278-16284, vol. 277, No. 18.
Inoshima et al., Anti-Monocyte Chemoattractant Protein-1 Gene Therapy Attenuates Pulmonary Fibrosis in Mice, American Journal of Physiology/Lung Cellular and Molecular Physiology, 2004, pp. L1038-L1044, vol. 286.
Itagaki et al., Relationship of Microglia and Astrocytes to Amyloid Deposits of Alzheimer Disease, Journal of Neuroimmunology, 1989, pp. 173-182, vol. 24.
Iwatsubo et al., Full-Length Amyloid-β(1-42(43)) and Amino-Terminally Modified and Truncated Amyloid-β42(43) Deposit in Diffuse Plaques, American Journal of Pathology, 1996, pp. 1823-1830, vol. 149, No. 6.
Jacobsen et al., Early-Onset Behavioral and Synaptic Deficits in a Mouse Model of Alzheimer's Disease, Proc. Natl. Acad. Sci USA, 2006, pp. 5161-5166, vol. 103.
Janeisch et al., Transgenic Animals, Science, 1988, pp. 1468-1474, vol. 240.
Jaenisch et al., Germ Line Integration and Mendelian Transmission of the Exogenous Moloney Leukemia Virus, Proc. Nat. Acad. Sci. USA, 1976, pp. 1260-1264, vol. 73.
Jahner et al., De Novo Methylation and Expression of Retroviral Genomes During Mouse Embryogenesis, Nature, 1982, pp. 623-628, vol. 298.
Jahner et al., Insertion of the Bacterial GPT Gene into the Germ Line of Mice by Retroviral Infection, Proc. Natl. Acad. Sci., 1985, pp. 6927-6931, vol. 82.
Jansen et al., Hydantoin-Substituted 4,6-Dichloroindole-2-carboxylic Acids as Ligands with High Affinity for the Glycine Binding Site of the NMDA Receptor, J Med Chem, 2003, pp. 64-73, vol. 46.
Johnson et al., Plaque Rupture after Short Period of Fat Feedings in the Apolipoprotein E-Knockout Mouse: Model Characterization and Effects of Pravastatin Treatment, Circulation, 2005, pp. 1422-1430, vol. 111.
Kang et al., The Precursor of Alzheimer's Disease Amyloid A4 Protein Resembles a Cell-Surface Receptor, Nature, 1987, pp. 733-736, vol. 325.
Katabuchi et al., Characterization of Macrophages in the Decidual Atherotic Spiral Artery with Special Reference to the Cytology of Foam Cells, Med Electron Microsc, 2003, pp. 253-262, vol. 36.
Karim et al., Human hypothetical protein FLJ20084 DNA, Accession AAL61267, 2003, 3 pages.
Lalowski et al., The "Nonamyloidogenic" p3 Fragment (Amyloid β17-42) Is a Major Constituent of Down's Syndrome Cerebellar Preamyloid, The Journal of Biological Chemistry, 1996, pp. 33623-33631, vol. 271.
Lavitrano et al., Sperm Cells as Vectors for Introducing Foreign DNA into Eggs: Genetic Transformation of Mice, Cell, 1989, pp. 717-723, vol. 57.
Lee et al., Glucocorticoids Regulate Expression of Dihydrofolate Reductase cDNA in Mouse Mammary Tumour Virus Chimaeric Plasmids, Nature, 1981, pp. 228-232, vol. 294.
Lemere, et al., The E280A Presenilin 1 Alzheimer Mutation Produces Increased Aβ42 Deposition and Severe Cerebellar Pathology, Nature Medicine, 1996, pp. 1146-1150, vol. 2.
Li et al., MCP-1 Overexpressed in Tuberous Sclerosis Lesions Acts as a Paracrine Factor for Tumor Developments, J Exp Med., 2005, pp. 617-624, vol. 202.
Lo, Transformation by Iontophoretic Microinjection of DNA: Multiple Integrations Without Tandem Insertions, Molecular and Cellular Biology, 1983, pp. 1803-1814, vol. 3.
Mann et al., Diffuse Plaques in the Cerebellum and Corpus Striatum in Down's Syndrome Contain Amyloid β Protein (Aβ) only in the Form of Aβ42(43), Neurodegeneration, 1996, pp. 115-120, vol. 5.
Masure et al., Expression of a Human Mutant Monocyte Chemotactic Protein 3 in Pichia pastoris and Characterization as an MCP-3 Receptor Antagonist, Journal of Interferon and Cytokine Research, 1995, pp. 955-963, vol. 15.
Maue et al., Neuron-Specific Expression of the Rat Brain Type II Sodium Channel Gene is Directed by Upstream Regulatory Elements, Neuron, 1990, pp. 223-231, vol. 4.
Meir et al., Atherosclerosis in the Apolipoprotein E-Deficient Mouse: A Decade of Progress, Arteriosclerosis, Thrombosis, and Vascular Biology, 2004, pp. 1006-1014, vol. 24.
Messer, Enzymatic Cyclization of L-Glutamine and L-Glutaminyl Peptides, 1963, Nature, pp. 1299, vol. 4874.
Mori et al., Mass Spectrometry of Purified Amyloid β Protein in Alzheimer's Disease, The Journal of Biological Chemistry, 1992, pp. 17082-17086, vol. 267.
Morris, Spatial Localization Does Not Require the Presence of Local Cues, Learning and Motivation, 1981, pp. 239-260, vol. 12.
Muller, Ten years of gene targeting: targeted mouse mutants, from vector design to phenotype analysis, Mechanisms of Development, 1999, pp. 3-21, vol. 82, Nos. 1-2.
No et al., Ecdysone-inducible Gene Expression in Mammalian Cells and Transgenic Mice, Proc. Natl. Acad. Sci. USA, 1996, pp. 3346-3351, vol. 93.
Ogata et al., The Role of Monocyte Chemoattractant Protein-1 (MCP-1) in the Pathogenesis of Collagen-Induced Arthritis in Rats, Journal of Pathology, 1997, pp. 106-114, vol. 182.
Ohashi et al., Cellular and Molecular Mechanisms of Atherosclerosis with Mouse Models, Trends Cardiovasc. Med., 2004, pp. 187-190, vol. 14.
Ohsugi et al., Anti-platelet aggregation and anti-blood coagulation activities of dipicolinic acid, a sporal component of Bacillus subtilis natto, Database accession No. 145:369541, 2005, Database CA (Online), Chemical Abstracts Service, Columbus, Ohio, US & Food Science and Technology Research, 2005, pp. 308-310, vol. 11, No. 3.
Ohta et al., Monocyte Chemoattractant Protein-1 Expression Correlates with Macrophage Infiltration and Tumor Vascularity in Human Gastric Carcinomas, International Journal of Oncology, 2003, pp. 773-778, vol. 22.
Park et al., HIV-1 Tat Promotes Monocyte Chemoattractant Protein-1 Secretion Followed by Transmigration of Monocytes, Blood, 2001, pp. 352-358, vol. 97.
Penn et al., Human genome derived single exon probe, Database accession No. ACH86904, 2004, Database Geneseq, 2 pages.
Pike et al., Amino-Terminal Deletions Enhance Aggregation of β-Amyloid Peptides In Vitro, The Journal of Biological Chemistry, 1995, pp. 23895-23898, vol. 270.
Pinkert et al., An Albumin Enhancer Located 10 kb Upstream Functions Along with its Promoter to Direct Efficient, Liver-Specific Expression in Transgenic Mice, Genes & Development, 1987, pp. 268-277, vol. 1.
Pohl et al., Primary Structure and Functional Expression of a Glutaminyl Cyclase, Proc. Natl. Acad. Sci USA., 1991, pp. 10059-10063, vol. 88.
Prokal et al., Metabolism-Based Brain-Targeting System for a Thyrotropin-Releasing Hormone Analogue, J. Med. Chem., 1999, pp. 4563-4571, vol. 42.
Proost et al., Posttranslational Modifications Affect the Activity of the Human Monocyte Chemotactic Proteins MCP-1 and MCP-2: Identification of MCP-2(6-76) as a Natural Chemokins Inhibitor, Journal of Immunology, 1998, pp. 4034-4041, vol. 160.
Queen et al., Immunoglobulin Gene Transcription is Activated by Downstream Sequence Elements, Cell, 1983, pp. 741-748, vol. 33.
Ray et al., Ectopic Expression of a C-KitW42 Minigene in Transgenic Mice: Recapitulation of W Phenotypes and Evidence for C-Kit Function in Melanoblast Progenitors, Genes & Development, 1991, pp. 2265-2273, vol. 5.

(56) References Cited

OTHER PUBLICATIONS

Russo et al., Presenilin-1 Mutations in Alzheimer's Disease, Nature, 2000, pp. 531-532, vol. 405.

Russo et al., Heterogeneity of Water-Soluble Amyloid β-Peptide in Alzheimer's Disease and Down's Syndrome Brains, FEBS Letters, 1997, pp. 411-416, vol. 409.

Russo et al., Identification of Amino-Terminally and Phosphotyrosine-Modified Carboxy-Terminal Fragments of the Amyloid Precursor Protein in Alzheimer's Disease and Down's Syndrome Brain, Neurobiology of Disease, 2001, pp. 173-180, vol. 8.

Russo et al., Pyroglutamate-Modified Amyloid β-Peptides—AβN3(pE)—Strongly Affect Cultured Neuron and Astrocyte Survival, Journal of Neurochemistry, 2002, pp. 1480-1489, vol. 82.

Saido et al., Involvement of Polyglutamine Endolysis Followed by Pyroglutamate Formation in the Pathogenesis of Triplet Repeat/Polyglutamine-Expansion Diseases, Medical Hypothesis, 2000, pp. 427-429, vol. 54, No. 3.

Saido et al., Dominant and Differential Deposition of Distinct β-Amyloid Peptide Species, AβN3(pE), in Senile Plaques, Neuron, 1995, pp. 457-466, vol. 14.

Saiura et al., Antimonocyte Chemoattractant Protein-1 Gene Therapy Attenuates Graft Vasculopathy, Arterioscler. Thromb. Vasc. Biol., 2004, pp. 1886-1890, vol. 24.

Sasahara et al., PDFG B-Chain in Neurons of the Central Nervous System, Posterior Pituitary, and in a Transgenic Model, Cell, 1991, pp. 217-227, vol. 64.

Schilling et al., Inhibition of Glutaminyl Cyclase Prevents pGlu-Aβ Formation after Intracortical/Hippocampal Microinjection in Vivo/In Situ, Journal of Neurochemistry, 2008, pp. 1225-1236, vol. 106, No. 3.

Schilling et al., Isolation, Catalytic Properties, and Competitive Inhibitors of the Zinc-Dependent Murine Glutaminyl Cyclase, Biochemistry, 2005, pp. 13415-13424, vol. 44, No. 40.

Schilling et al., Identification of Human Glutaminyl Cyclase as a Metalloenzyme, Potent Inhibition by Imidazole Derivatives and Heterocyclic Chelators, Journal of Biological Chemistry, 2003, pp. 49773-49779, vol. 278, No. 50.

Selkoe, Alzheimer's Disease: Genes, Proteins, and Therapy, Physiological Review, 2001, pp. 741-765, vol. 81.

Selkoe, The Cell Biology of β-Amyloid Precursor Protein and Presenilin in Alzheimer's Disease, Trends in Cell Biology, 1998, pp. 447-453, vol. 8.

Sen et al., Development in directed evolution for improving enzyme functions, Appl Biochem Biotechnol, 2007, pp. 212-223, vol. 143, No. 3.

Shirotani et al., Generation of Amyloid β Peptide with Pyroglutamate at Position 3 in Primary Cortical Neurons, Neuroscience Letters, 2002, pp. 25-28, vol. 327.

Simons et al., Amyloidogenic Processing of the Human Amyloid Precursor Protein in Primary Cultures of Rat Hippocampal Neurons, The Journal of Neuroscience, 1996, pp. 899-908, vol. 16.

Stewart et al., Expression of Retroviral Vectors in Transgenic Mice Obtained by Embryo Infection, The EMBO Journal, 1987, pp. 383-388, vol. 6.

Sturchler-Pierrat et al., Two Amyloid Precursor Protein Transgenic Mouse Models with Alzheimer Disease-Like Pathology, Proc. Natl. Acad. Sci., 1997, pp. 13287-13292, vol. 94.

Subramaniam et al., Tissue-Specific Regulation of the a-Myosin Heavy Chain Gene Promoter in Transgenic Mice, The Journal of Biological Chemistry, 1991, pp. 24613-24620, vol. 266.

Suzuki et al., *Homo sapiens* mRNA for glutaminyl-peptide cyclotransferase-like variant, Database accession No. AK222636, May 2006, Database EMBL, 2 pages.

Suzuki et al., Glutaminyl-peptide cyclotransferase-like variant, Database accession No. Q53HE4, Sep. 2006, Database UniProt, 2 pages.

Tekirian et al., N-Terminal Heterogeneity of Parenchymal and Cerebrovascular Aβ Deposits, Journal of Neuropathology and Experimental Neurology, 1998, pp. 76-94, vol. 57.

Tekirian et al., Toxicity of Pyroglutaminated Amyloid β-Peptides 3(pE)-40 and -42 is Similar to That of Aβ-40 and -42, Journal of Neurochemistry, 1999, pp. 1584-1589, vol. 73.

Terry and Katzman, Robert, Senile Dementia of the Alzheimer Type, Ann Neurol, 1983, pp. 497-506, vol. 14.

Thompson et al., Germ Line Transmission and Expression of a Corrected HPRT Gene Produced by Gene Targeting in Embryonic Stem Cells, Cell, 1989, pp. 313-321, vol. 56.

Van Damme et al., The Role of CD26/DPP IV in Chemokine Processing, Chem Immunol, 1999, pp. 42-56, vol. 72.

Van Der Putten et al., Efficient Insertion of Genes into the Mouse Germ Line Via Retroviral Vectors, Proc. Natl. Acad. Sci USA, 1985, pp. 6148-6152, vol. 82.

Wada et al., Gene Therapy via Blockage of Monocyte Chemoattractant Protein-1 for Renal Fibrosis, J. Am. Soc. Nephrol, 2004, pp. 940-948, vol. 15.

Werbel and Elslager, Antischistosomal Effects of 5-(2,4,5-Trichlorophenyl)hydantoin and Related Compounds, J Med Chem, 1977, pp. 1569-1572, vol. 20.

White et al., Excitatory Monocyte Chemoattractant Protein-1 Signaling is Up-Regulated in Sensory Neurons after Chronic Compression of the Dorsal Root Ganglion, PNAS, 2005, pp. 14092-14097, vol. 102.

Whisstock et al., Prediction of protein function from protein sequence and structure, Quarterly Review of Biophysics, 2003, pp. 307-340, vol. 36, No. 3.

Winoto et al., A Novel, Inducible and T Cell-Specific Enhancer Located at the 3' End of the T Cell Receptor α Locus, The EMBO Journal, 1989, pp. 729-733, vol. 8.

Xi et al., Expression of a Large Family of POU-Domain Regulatory Genes in Mammalian Brain Development, Nature, 1989, pp. 35-42, vol. 340.

Yamamoto et al., Overexpression of Monocyte Chemotactic Protein-1/CCL2 in β-Amyloid Precursor Protein Transgenic Mice Show Accelerated Diffuse β-Amyloid Deposition, American Journal of Pathology, 2005, pp. 475-1485, vol. 166.

Yao et al., Functional Ecdysone receptor is the Product of EcR and Ultraspiracle Genes, Letters to Nature, 1993, pp. 476-479, vol. 366.

Zhang et al., Structure/Activity Analysis of Human Monocyte Chemoattractant Protein-1 (MCP-1) by Mutagenesis, The Journal of Biological Chemistry, 1994, pp. 15918-15924, vol. 269.

* cited by examiner

Figure 7
(a)
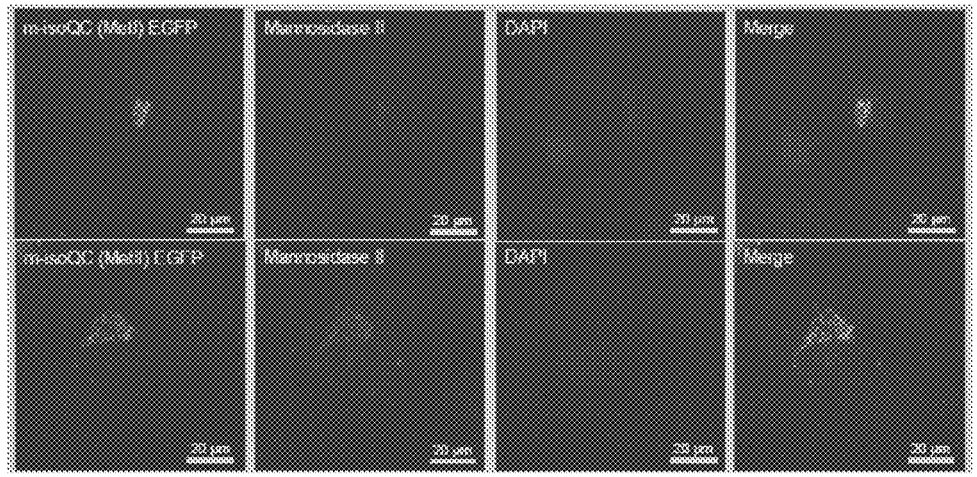
(b)
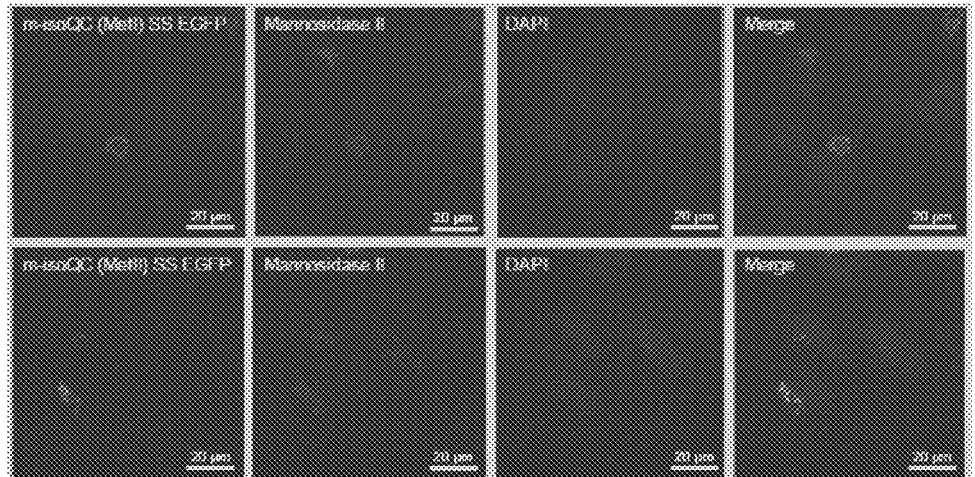

Figure 8
(a)
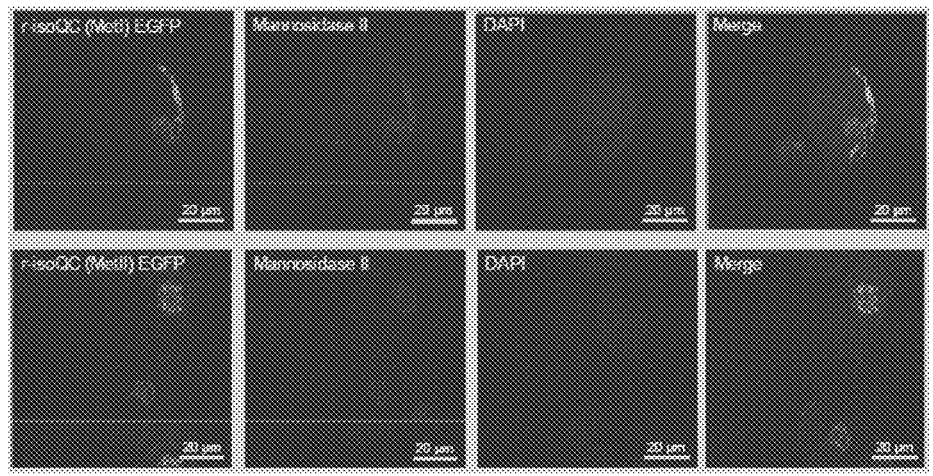
(b)
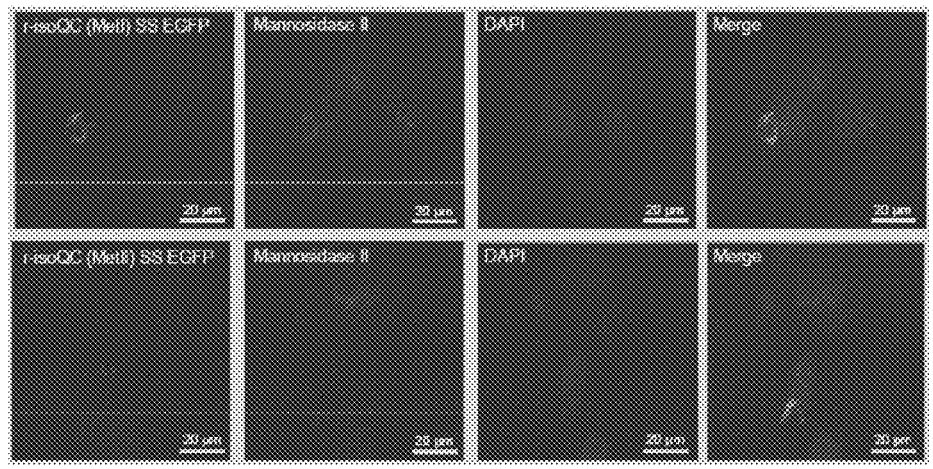

Figure 9
(a)
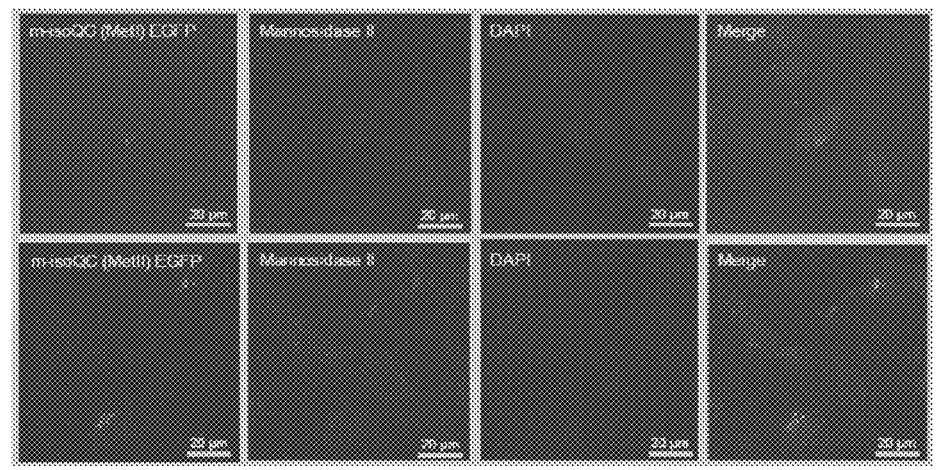
(b)
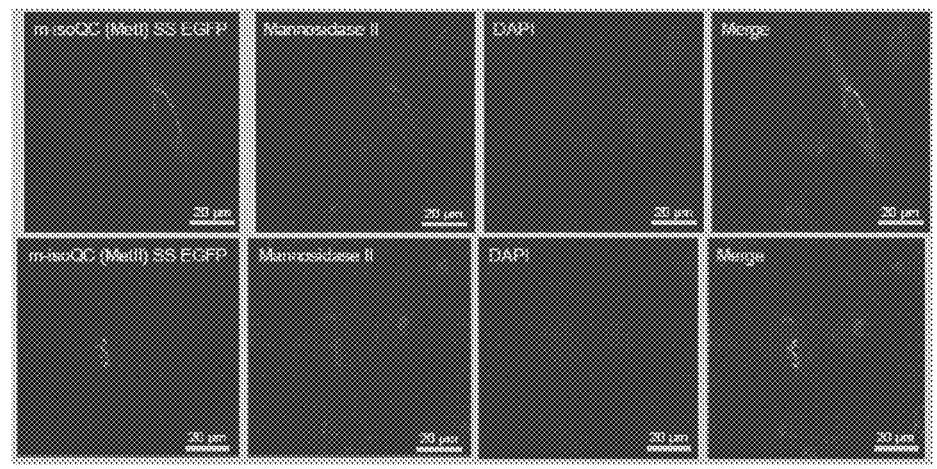

Figure 10
(a)
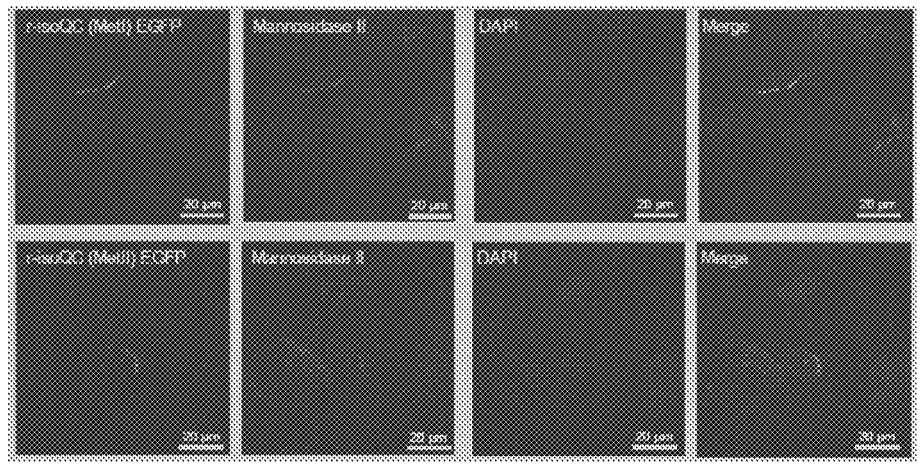
(b)
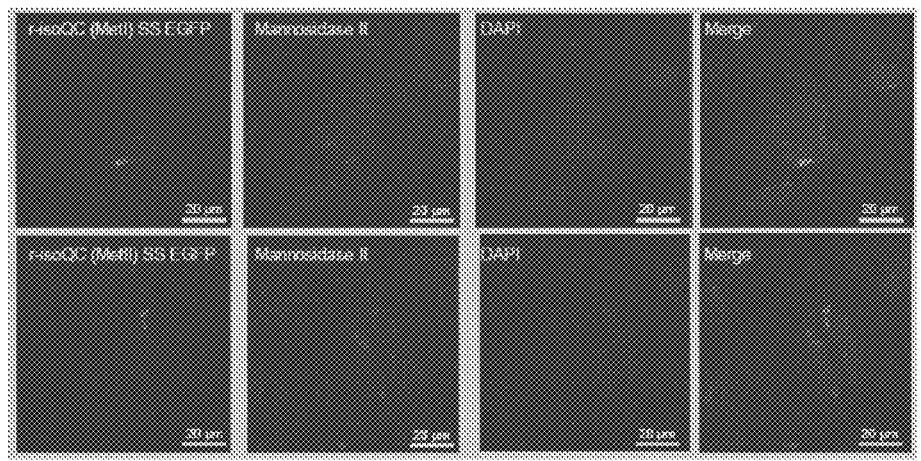

Figure 11
(a)
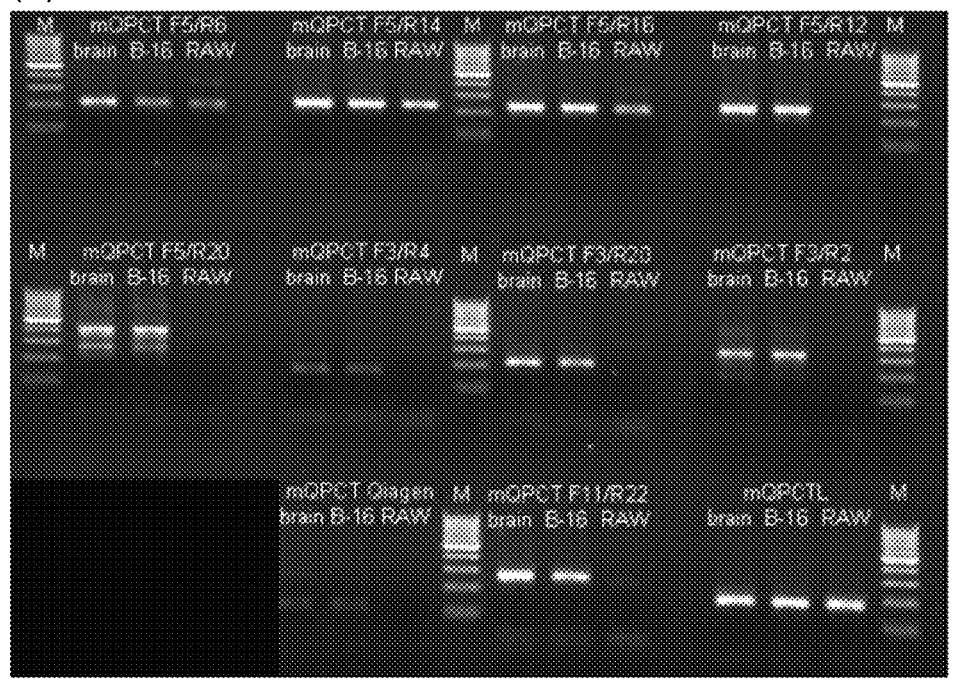
(b)
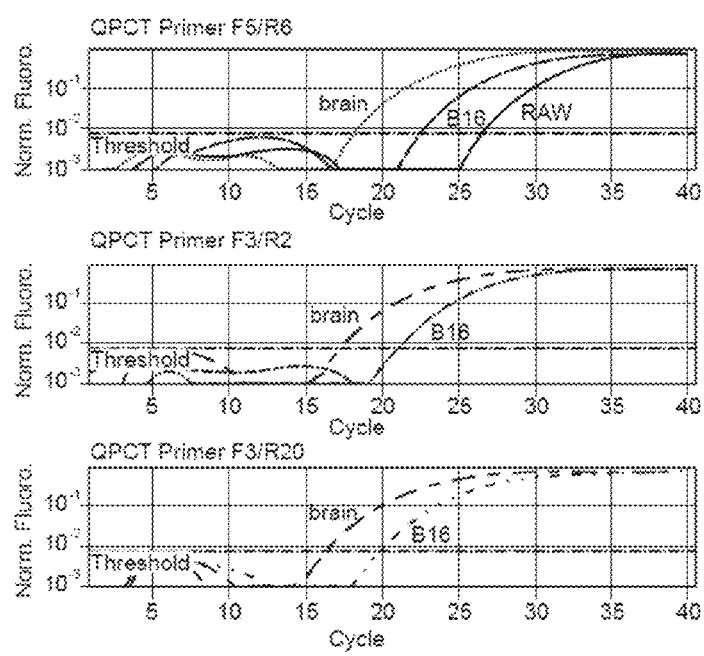

Figure 12
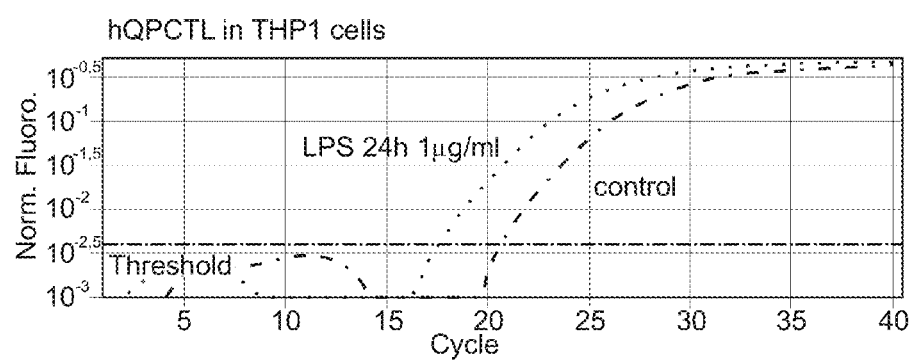
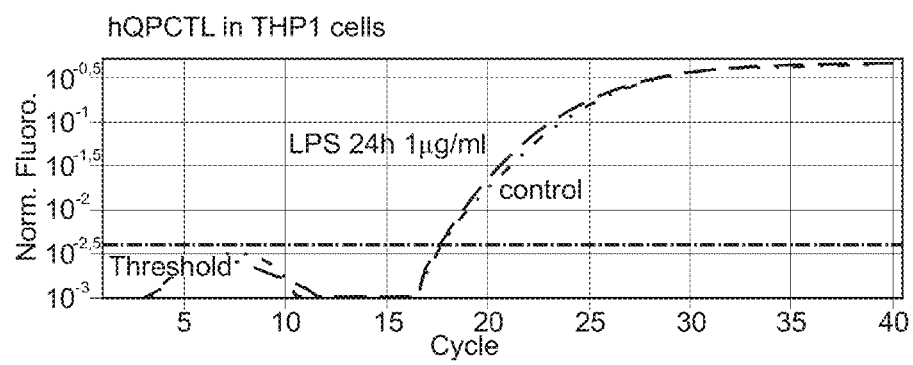

Figure 13

```
hisoQC  MRSGGRGRPRLRLGERGLMEPLLPPKRRLLPRVRLLP-LLLALAVGSAFYTIWSGWHRRT
misoQC  MSPGSRGRPRQRLEDRGLMKPPSLSKRRLLPRVQFLPLLLLALAMGLAFYIVWNSWHPGV
risoQC  MSPASRGRSRQRLGDRGLMKPPSLSKRRLLPRVQLLPLLLLALALGLAFYIVWNSWHPGV
        *  ..***.* ** :***:*   ,*******:;** ******;* *** ;*..** .

hisoQC  EELPLGRELRVPLIGSLPEARLRRVVGQLDPQRLWSTYLRPLLVVRTPGSPGNLQVRKFL
misoQC  EEMSRSRDLRVPLIGSLSEAKLRLVVGQLDPQRLWGTFLRPLLIVRPPGSSGNLQVRKFL
risoQC  EEVSRSRDLRVPLIGSLSEAKLRLVVGQLDPQRLWGTFLRPLLIVRPPGSPGNLQVRKFL
        **:.  .*:******.: ********.*:*** :.* ****** hisoQC  EATLRSLTAGWHVELDPFTASTPLGPVDFGNVVATLDPRAARHLTLACHYDSKLFPPGST
misoQC  EATLQSLSAGWHVELDPFTASTPLGPLDFGNVVATLDPGAARHLTLACHYDSKFFPPGLP
risoQC  EATLQSLSAGWHVELDPFTASTPLGPLDFGNVVATLDPGAARHLTLACHYDSKFFPPGLP
        ****:**:******************:********** **************:****  .

hisoQC  PFVGATDSAVPCALLLELAQALDLELSRAKKQAAPVTLQLLFLDGEEALKEWGPKDSLYG
misoQC  PFVGATDSAVPCALLLELVQALDAMLSRIKQQAAPVTLQLLFLG-EEALKEWGPKDSLYG
risoQC  PFVGATDSAVPCALLLELVQALDVMLSRIKQQAAPVTLQLLFLDGEEALKEWGPKDSLYG
        ****************.  * *:***********. *********** hisoQC  SRHLAQLMESIPHSPGPTRIQAIELFMLLDLLGAPNPTFYSHFPRTVRWFHRLRSIEKRL
misoQC  SRHLAQIMESIPHSPGPTRIQAIELFVLLDLLGASSPIFFSHFPRTARWFQRLRSIEKRL
risoQC  SRHLAQIMESIPHSPGPTRIQAIELFVLLDLLGAPSPIFFSHFPRTARWFQRLRSIEKRL
        ****:**************:*****..* *:**** .*:******** hisoQC  HRLNLLQSHPQEVMYFQPGEPSGSVEDDHIPFLRRGVPVLHLISTPFPAVWHTPADTEVN
misoQC  HRLNLLQSHPQEVMYFQPGEPPGPVEDDHIPFLRRGVPVLHLIATPFPAVLHTPADTEAN
risoQC  HRLNLLQSHPQEVMYFQPGEPPGPVEDDHIPFLRRGVPVLHLIAMPFPAVWHTPADTEAN
        *********************.*.****************:  * *****.* hisoQC  LHPPTVHNLCRILAVFLAEYLGL
misoQC  LHPPTVHNLSRILAVFLAEYLGL
risoQC  LHPPTVHNLSRILAVFLAEYLGL
        *********.*************
```

Figure 18
(a)
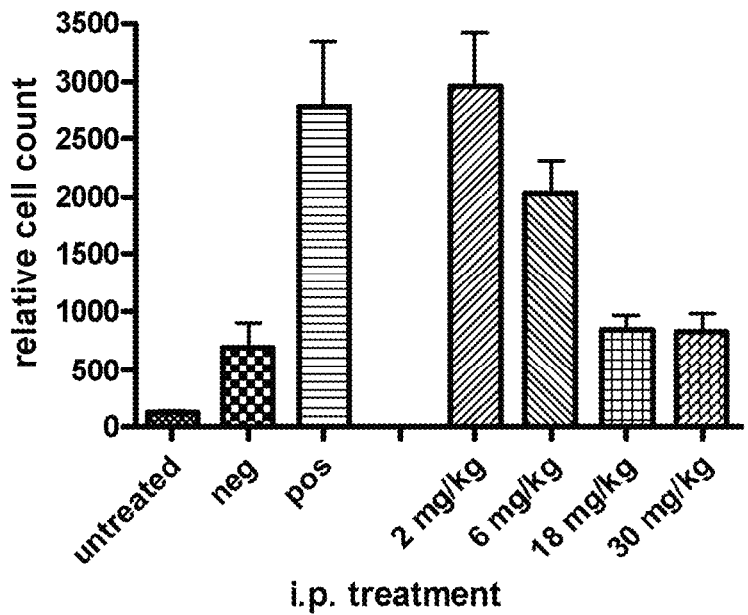
(b)
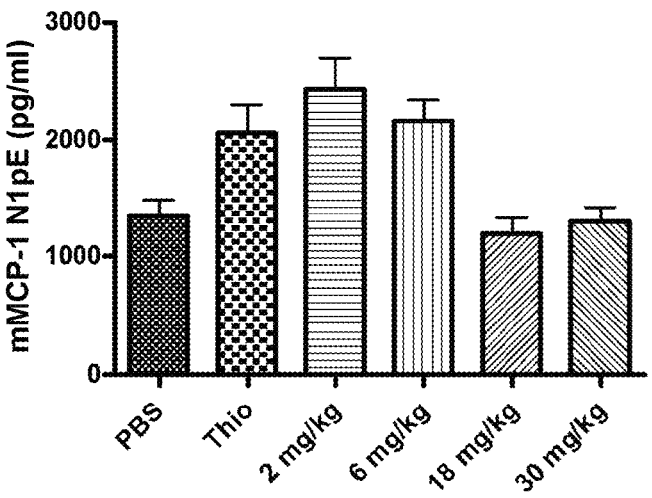

Figure 19
(a)
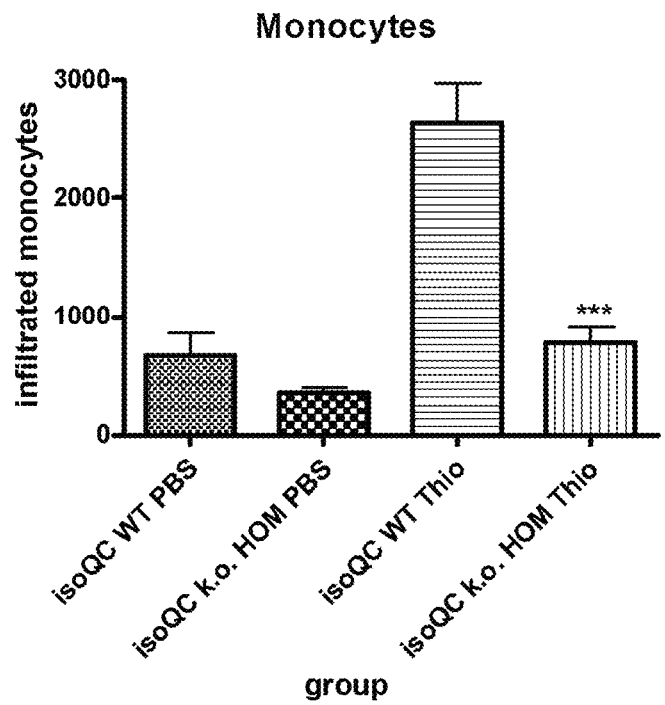
(b)
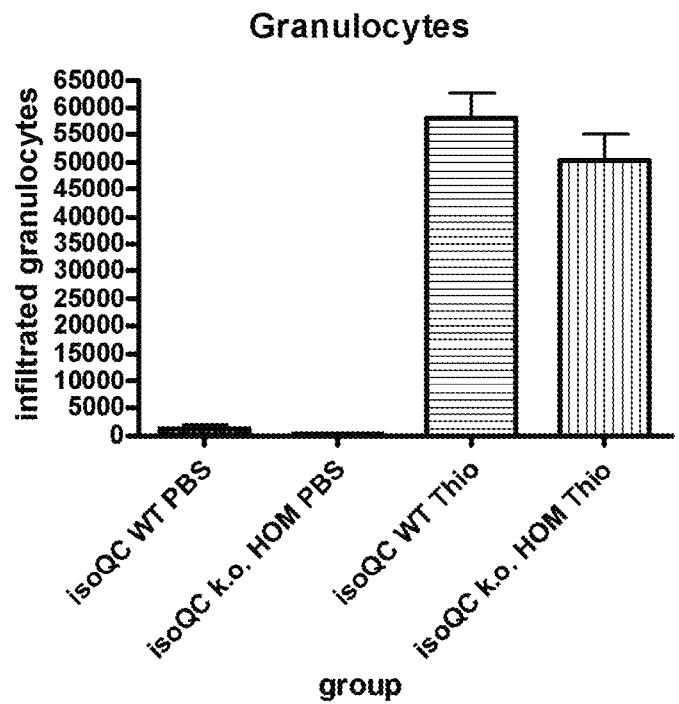

Figure 22
(a)
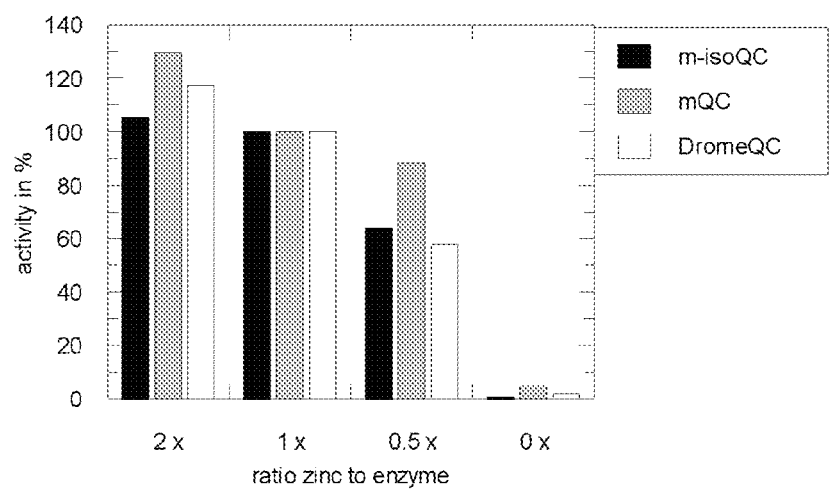
(b)
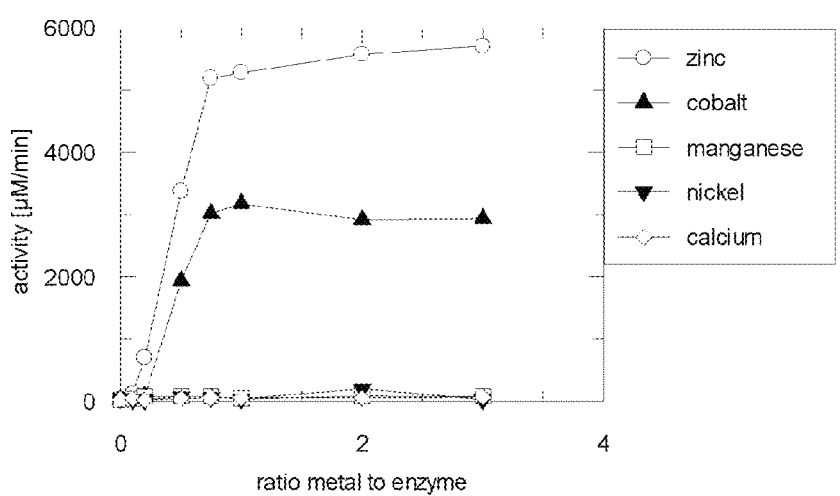

Figure 26
(a)
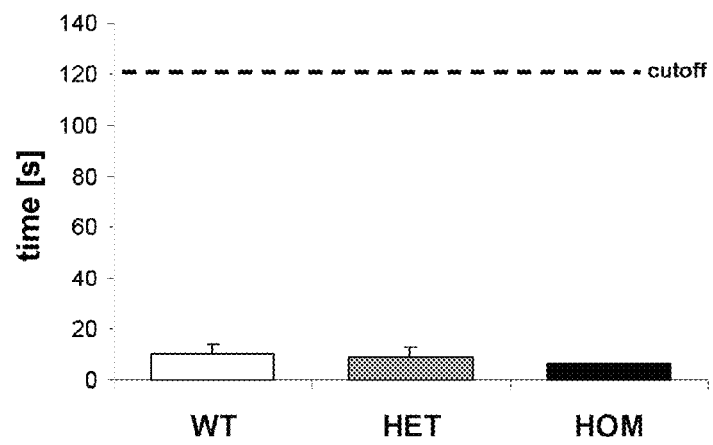
(b)
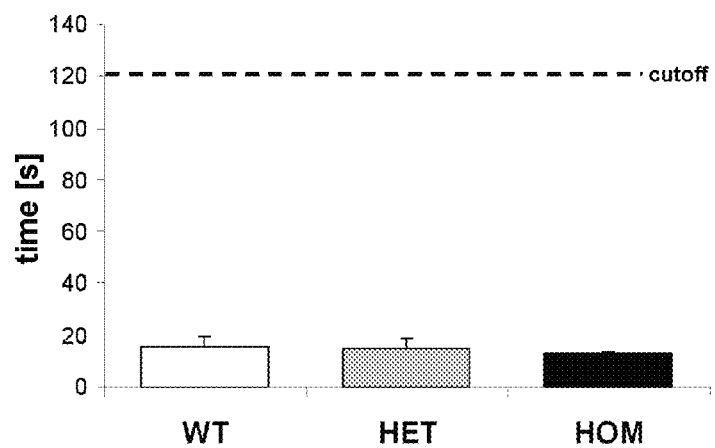

Figure 27
(a)
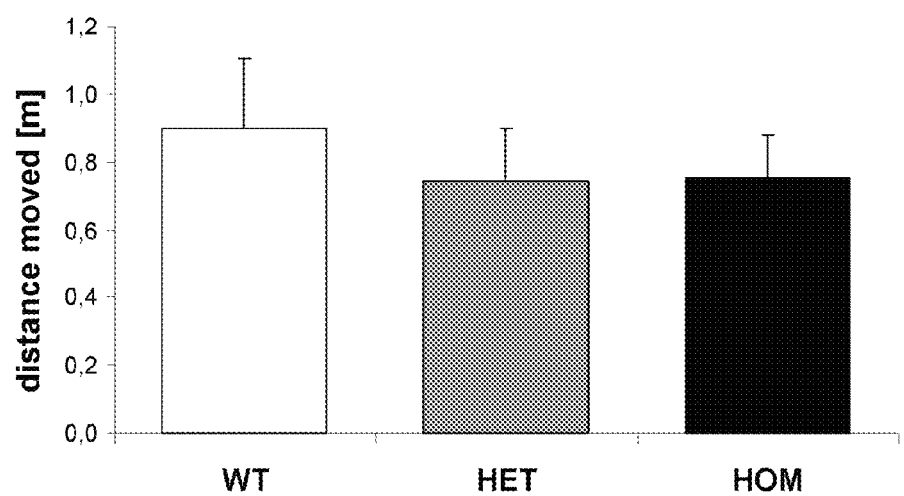
(b)
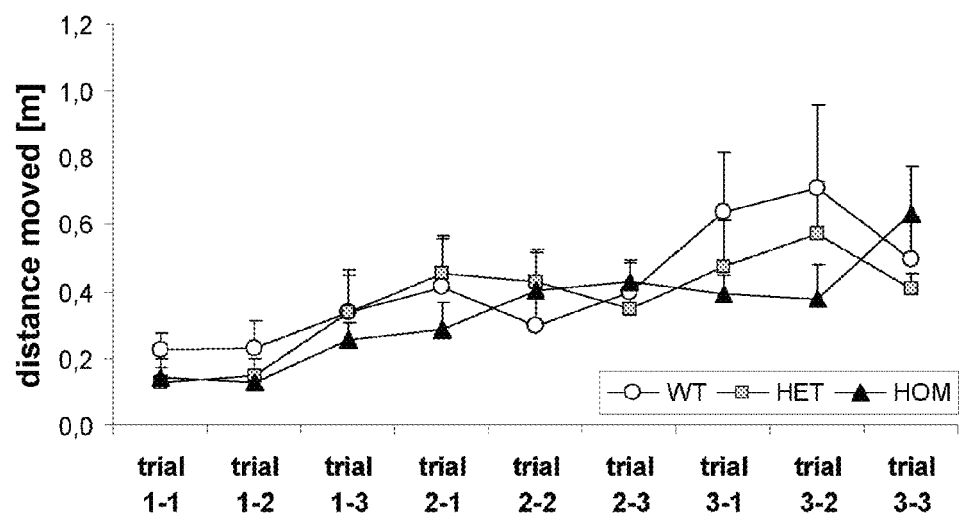

MOUSE MODELS CARRYING A KNOCK-OUT MUTATION OF THE QPCTL-GENE

RELATED APPLICATION DATA

This application is a Continuation-in-Part of U.S. application Ser. No. 13/325,015 filed Dec. 13, 2011 which is a Continuation of U.S. Non-provisional application Ser. No. 12/497,082, filed on Jul. 2, 2009, which is a Division of U.S. Non-provisional application Ser. No. 11/859,217 filed on Sep. 21, 2007, which claims benefit of U.S. Provisional Patent Application Ser. No. 60/846,244, filed on Sep. 21, 2006 and U.S. Provisional Patent Application Ser. No. 60/947,780, filed on Jul. 3, 2007, each of which is incorporated herein by reference in its entirety. This application is also a Continuation-in-Part of U.S. application Ser. No. 12/782,953 filed May 19, 2010 which is a Non-provisional of U.S. Provisional Patent Application Ser. No. 61/179,423, filed May 19, 2009, each of which is incorporated herein by reference in its entirety.

FIELD

The present invention relates generally to knock-out animals, in particular mouse models having a knock-out mutation of the QPCTL gene.

SEQUENCE LISTING

The Sequence Listing, which is a part of the present disclosure, includes a computer readable form comprising nucleotide and/or amino acid sequences of the present invention. The subject matter of the Sequence Listing is incorporated herein by reference in its entirety.

BACKGROUND OF THE INVENTION

QPCTL (i.e. glutaminyl peptide cyclotransferase like), also termed Iso-glutaminyl cyclase (isoQC) (see SEQ ID NO's: 2, 5 and 7 for the QPCTL's from mouse, rat and human, respectively and SEQ ID NO's: 1, 4 and 6 for the cDNA sequences of the QPCTL's from mouse, rat and human, respectively) catalyzes the intramolecular cyclization of N-terminal glutamine residues into pyroglutamic acid (5-oxo-proline, pGlu*) with liberation of ammonia and the intramolecular cyclization of N-terminal glutamate residues into pyroglutamic acid with liberation of water.

Glutaminyl cyclase (QC, EC 2.3.2.5) (or QPCT) catalyzes the intramolecular cyclization of N-terminal glutamine residues into pyroglutamic acid (pGlu*) liberating ammonia. A QC was first isolated by Messer from the Latex of the tropical plant *Carica papaya* in 1963 (Messer, M. (1963) Nature 4874, 1299). 24 years later, a corresponding enzymatic activity was discovered in animal pituitary (Busby, W. H. J. et al. (1987) J Biol. Chem. 262, 8532-8536; Fischer, W. H. and Spiess, J. (1987) Proc. Natl. Acad. Sci. U.S.A. 84, 3628-3632). For the mammalian QC, the conversion of Gln into pGlu by QC could be shown for the precursors of TRH and GnRH (Busby, W. H. J. et al. (1987) J Biol Chem 262, 8532-8536; Fischer, W. H. and Spiess, J. (1987) Proc Natl Acad Sci U.S.A. 84, 3628-3632). In addition, initial localization experiments of QC revealed a co-localization with its putative products of catalysis in bovine pituitary, further improving the suggested function in peptide hormone synthesis (Bockers, T. M. et al. (1995) J Neuroendocrinol. 7, 445-453). In contrast, the physiological function of the plant QC is less clear. In case of the enzyme from *C. papaya*, a role in the plant defence against pathogenic microorganisms was suggested (El Moussaoui, A. et al. (2001) Cell. Mol. Life. Sci. 58, 556-570). Putative QCs from other plants were identified by sequence comparisons (Dahl, S. W. et al. (2000) Protein Expr. Purif. 20, 27-36). The physiological function of these enzymes, however, is still ambiguous.

The QCs known from plants and animals show a strict specificity for L-glutamine in the N-terminal position of the substrates and their kinetic behavior was found to obey the Michaelis-Menten equation (Pohl, T. et al. (1991) Proc. Natl. Acad. Sci. U.S.A. 88, 10059-10063; Consalvo, A. P. et al. (1988) Anal. Biochem. 175, 131-138; Gololobov, M. Y. et al. (1996) Biol. Chem. Hoppe Seyler 377, 395-398). A comparison of the primary structures of the QCs from *C. papaya* and that of the highly conserved QC from mammals, however, did not reveal any sequence homology (Dahl, S. W. et al. (2000) Protein Expr. Purif. 20, 27-36). Whereas the plant QCs appear to belong to a new enzyme family (Dahl, S. W. et al. (2000) Protein Expr. Purif. 20, 27-36), the mammalian QCs were found to have a pronounced sequence homology to bacterial aminopeptidases (Bateman, R. C. et al. (2001) Biochemistry 40, 11246-11250), leading to the conclusion that the QCs from plants and animals have different evolutionary origins.

The subject matter of the present invention is particularly useful in the field of QPCT-related diseases, one example of those being Alzheimer's Disease, whereby these diseases are simultaneously QPCTL-related in view of the above-described similarly catalyzed reaction. Alzheimer's disease (AD) is characterized by abnormal accumulation of extracellular amyloidotic plaques closely associated with dystrophic neurones, reactive astrocytes and microglia (Terry, R. D. and Katzman, R. 1983 Ann. Neurol. 14, 497-506; Glenner, G. G. and Wong, C. W. (1984) Biochem. Biophys. Res. Comm. 120, 885-890; Intagaki, S. et al. (1989) J Neuroimmunol. 24, 173-182; Funato, H. et al. (1998) Am. J Pathol. 152, 983-992; Selkoe, D. J. (2001) Physiol. Rev. 81, 741-766). Amyloid-beta (abbreviated as Aβ) peptides are the primary components of senile plaques and are considered to be directly involved in the pathogenesis and progression of AD, a hypothesis supported by genetic studies (Glenner, G. G. and Wong, C. W. (1984) Biochem. Biophys. Res. Comm. 120, 885-890; Borchelt, D. R. et al. (1996) Neuron 17, 1005-1013; Lemere, C. A. et al. (1996) Nat. Med. 2, 1146-1150; Mann, D. M. and Iwatsubo, T. (1996) Neurodegeneration 5, 115-120; Citron, M. et al. (1997) Nat. Med. 3, 67-72; Selkoe, D. J. (2001) Physiol. Rev. 81, 741-766). Aβ is generated by proteolytic processing of the β-amyloid precursor protein (APP) (Kang, J. et al. (1987) Nature 325, 733-736; Selkoe, D. J. (1998) Trends Cell. Biol. 8, 447-453), which is sequentially cleaved by β-secretase at the N-terminus and by γ-secretase at the C-terminus of Aβ (Haass, C. and Selkoe, D. J. (1993) Cell 75, 1039-1042; Simons, M. et al. (1996) J Neurosci. 16 899-908). In addition to the dominant Aβ peptides starting with L-Asp at the N-terminus (Aβ1-42/40), a great heterogeneity of N-terminally truncated forms occurs in senile plaques. Such shortened peptides are reported to be more neurotoxic in vitro and to aggregate more rapidly than the full-length isoforms (Pike, C. J. et al. (1995) J Biol. Chem. 270, 23895-23898). N-truncated peptides are known to be overproduced in early onset familial AD (FAD) subjects (Saido, T. C. et al. (1995) Neuron 14, 457-466; Russo, C, et al. (2000) Nature 405, 531-532), to appear early and to increase with age in Down's syndrome (DS) brains (Russo, C. et al. (1997) FEBS Lett. 409, 411-416, Russo, C. et al. (2001) Neurobiol. Dis. 8, 173-180; Tekirian, T. L. et al. (1998) J Neuropathol. Exp. Neurol. 57, 76-94). Finally, their amount reflects the progressive severity of the disease (Russo, C. et al. (1997) FEBS Lett 409, 411-416; Güntert, A. et al. (2006) Neuroscience 143, 461-475). Additional post-translational processes may further modify the N-terminus by isomerization or racemization of the aspartate at position 1 and 7 and by cyclization of glutamate at residues 3 and 11. Pyroglutamate-containing isoforms at position 3 [pGlu$^3$Aβ3-40/42] represent the prominent forms—approximately 50% of the total Aβ amount—of the N-truncated species in senile plaques (Mori, H. et al. (1992) J Biol. Chem. 267, 17082-17086, Saido, T. C. et al. (1995) Neuron 14, 457-466; Russo, C. et al. (1997) FEBS Lett. 409, 411-416; Tekirian, T. L. et al. (1998) J Neuropathol Exp Neurol 57, 76-94; Geddes, J. W. et al. (1999) Neurobiol Aging 20, 75-79; Harigaya, Y. et al. (2000) Biochem. Biophys. Res. Commun. 276, 422-427) and they are also present in pre-amyloid lesions (Lalowski, M. et al. (1996) J Biol. Chem. 271, 33623-33631). The accumulation of AβN3 (pE) peptides is likely due to the structural modification that enhances aggregation and confers resistance to most amino-peptidases (Saido, T. C. et al. (1995) Neuron 14, 457-466; Tekirian, T. L. et al. (1999) J Neurochem 73, 1584-1589). This evidence provides clues for a pivotal rote of AβN3 (pE) peptides in AD pathogenesis. However, relatively little is known about their neurotoxicity and aggregation properties (He, W. and Barrow, C. J. (1999) Biochemistry 38, 10871-10877; Tekirian, T. L. et al. (1999) J Neurochem. 73, 1584-1589). Moreover, the action of these isoforms on glial cells and the glial response to these peptides are completely unknown, although activated glia is strictly associated with senile plaques and might actively contribute to the accumulation of amyloid deposits. In recent studies the toxicity, aggregation properties and catabolism of Aβ1-42, Aβ1-40, [pGlu$^3$]Aβ3-42, [pGlu$^3$]Aβ3-40, [pGlu$^{11}$]Aβ11-42 and [pGlu$^{11}$]Aβ11-40 peptides were investigated in neuronal and glial cell cultures, and it was shown that pyroglutamate modification exacerbates the toxic properties of Aβ-peptides and also inhibits their degradation by cultured astrocytes. Shirotani et al. investigated the generation of [pGlu$^3$]Aβ peptides in primary cortical neurons infected by recombinant Sindbis virus in vitro. They constructed amyloid precursor protein complementary DNAs, which encoded a potential precursor for [pGlu$^3$]Aβ by amino acid substitution and deletion. For one artificial precursor starting with an N-terminal glutamine residue instead of glutamate in the natural precursor, a spontaneous conversion or an enzymatic conversion by glutaminyl cyclase to pyroglutamate was suggested. The cyclization mechanism of N-terminal glutamate at position 3 in the natural precursor of [pGlu$^3$]Aβ was neither determined in vitro, in situ nor in vivo (Shirotani, K. et al. (2002) NeuroSci. Lett. 327, 25-28).

Thus, there is a clear need in the art for the provision of knock-out animals, in particular knock-out mice which carry a knock-out mutation in the QPCTL gene, to enable exact investigations as to the function, relevance and potential of the QPCTL gene as well as the QPCTL protein.

The aim of this invention was to develop knock-out animals, i.e. mouse models carrying a constitutive mutation of the QPCTL gene.

SUMMARY OF THE INVENTION

The present invention comprises methods and compositions for non-human knock-out, in particular mammalian, models for QPCTL-related diseases. Specifically, the present invention comprises non-human animal models that have a knock-out mutation in the QPCTL gene, resulting in the knock-out of QPCTL.

Another aspect of the present invention comprises methods and compositions for screening for QPCTL inhibitors/effectors.

A further aspect of the present invention comprises methods and compositions for screening for inhibitors/effectors, which are selective for gutaminyl cyclase (QC, QPCT).

A further aspect of the present invention comprises methods and compositions for screening for inhibitors/effectors, which are selective for QPCTL.

Preferred according to the aforementioned aspects of the present invention are methods and compositions for screening for inhibitors of QPCT and/or QPCTL.

Additionally, the present invention comprises methods and compositions for the treatment and/or prevention of QPCTL-related diseases, particularly methods and compositions that inhibit or promote QPCTL.

Accordingly, various embodiments provide an animal, which carries a QPCTL knock-out mutation.

It is a further object of the invention to provide a non-human animal model system, which carries a QPCTL knock-out mutation.

It is an additional object of the invention to provide a non-human animal model system to study the in vivo and in vitro regulation, function and effects of QPCTL in specific tissue types.

It is a further object of the invention to provide a non-human animal model system to study the function and concentrations of pyroglutamate-modified hormones, most preferably cytokine and chemokine function.

The present invention provides pharmaceutical compositions for parenteral, enteral or oral administration, comprising at least one effector of QPCTL optionally in combination with customary carriers and/or excipients, wherein said effector of QPCTL was identified by employing the screening methods and QPCTL knock-out animals of the present invention.

Moreover, the present invention provides pharmaceutical compositions for parenteral, enteral or oral administration, comprising at least one effector, which is selective for glutaminyl cyclase (QC, QPCT) or which is selective for QPCTL, optionally in combination with customary carriers and/or excipients, wherein said specific effector of glutaminyl cyclase or QPCTL was identified by employing the screening methods and QPCTL knock-out animals of the present invention.

Preferred are pharmaceutical compositions comprising at least one inhibitor, which is selective for glutaminyl cyclase (QC, QPCT) or which is selective for QPCTL, optionally in combination with customary carriers and/or excipients, wherein said specific inhibitor of glutaminyl cyclase or QPCTL was identified by employing the screening methods and QPCTL knock-out animals of the present invention.

BRIEF DESCRIPTION OF THE FIGURES

Further understanding of these and other aspects of the present invention will be gained by reference to the figures, which represent the following:

FIG. 7 shows the subcellular localization of mouse-isoQC (m-isoQC) in LN405 cells: (a) localization of m-isoQC-EGFP fusion proteins starting with one of the alternative start methionines MetI or MetII, and (b) localization of a fusion protein consisting of the N-terminal sequences of m-isoQC starting with MetI or MetII and ending at Ser 55 (numbering is based on MetI representing the N-terminal amino acid position 1, compare to FIG. 13), and a C-terminal EGFP fusion. The Golgi complex was stained using anti-mannosidase II antibody. Co-localization is shown by superimposition of EGFP fluorescence and Cy3 fluorescence (Merge).

FIG. 8 shows the subcellular localization of rat-isoQC (r-isoQC) in LN405 cells: (a) localization of r-isoQC-EGFP fusion proteins starting with one of the alternative start methionine MetI or with MetII and (b) localization of a fusion protein consisting of the N-terminal sequences of r-isoQC starting with MetI or MetII and ending at Ser 55 (numbering is based on MetI representing the N-terminal amino acid position 1, compare to FIG. 13), and a C-terminal EGFP fusion. The Golgi complex was stained using anti-mannosidase II antibody. Co-localization is shown by superimposition of EGFP fluorescence and Cy3 fluorescence (Merge).

FIG. 9 shows the subcellular localization of mouse-isoQC (m-isoQC) in SH-SY5Y cells: (a) localization of m-isoQC-EGFP fusion proteins starting with one of the alternative start methionines MetI or MetII, and (b) localization of a fusion protein consisting of the N-terminal sequences of m-isoQC starting with MetI or MetII and ending at Ser 55 (numbering is based on MetI representing the N-terminal amino acid position 1, compare to FIG. 13), and a C-terminal EGFP fusion. The Golgi complex was stained using anti-mannosidase II antibody. Co-localization is shown by superimposition of EGFP fluorescence and Cy3 fluorescence (Merge).

FIG. 10 shows the subcellular localization of rat-isoQC (r-isoQC) in SH-SYS5 cells: (a) localization of r-isoQC-EGFP fusion proteins starting with one of the alternative start methionine MetI or with MetII and (b) localization of a fusion protein consisting of the N-terminal sequences of r-isoQC starting with MetI or MetII and ending at Ser 55 (numbering is based on MetI representing the N-terminal amino acid position 1, compare to FIG. 13), and a C-terminal EGFP fusion. The Golgi complex was stained using anti-mannosidase II antibody. Co-localization is shown by superimposition of EGFP fluorescence and Cy3 fluorescence (Merge).

FIG. 11 shows the results of the quantitative PCR for characterization of mouse QC (mQPCT) and mouse-isoQC (mQPCTL) expression in RAW cells. (a) Analysis of PCR amplification products using agarose gel electrophoresis. M-100 bp ladder (Peqlab, Erlangen, Germany), Brain: products of RNA isolated from brain tissues, B16: products of RNA isolated from B16 melanoma cells, RAW: products of RNA isolated from RAW264.7 cells. (b) Amplification curves using primer pairs QPCT F5/R6, F3/R2 and F3/R20.

FIG. 12 shows quantitative PCR results for human QC (hQPCT) and human isoQC (hQPCTL) gene expression in THP1 cells after treatment with LPS (1 µg/ml) for 24 h.

FIG. 13 shows a sequence alignment of human, mouse and rat isoQC. The proteins share a sequence identity of 83%. The two different, potential start methionines are highlighted in bold.

Figure 1:
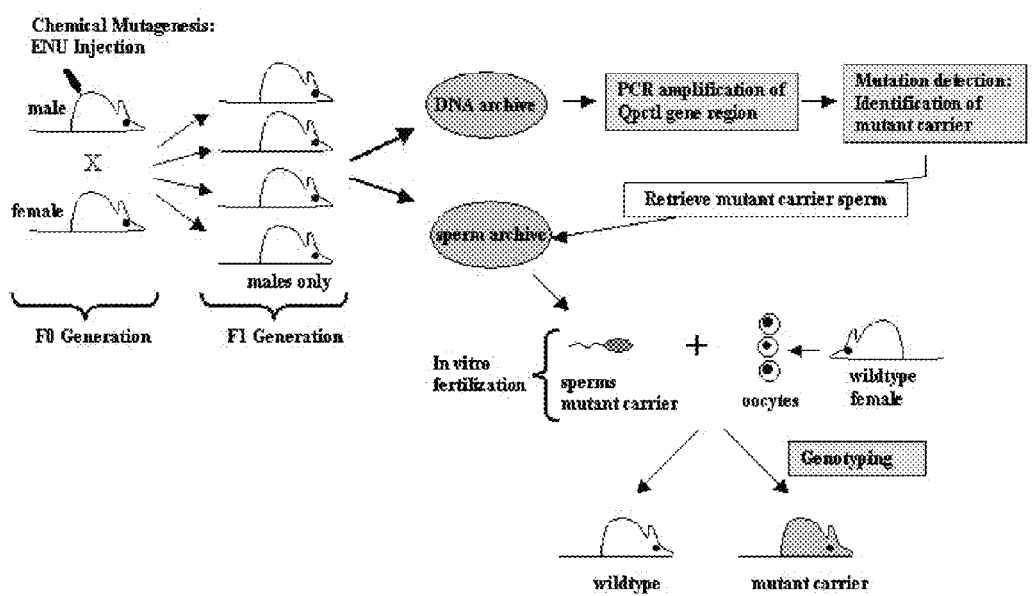
FIG. 1 shows the principle for the isolation of constitutive knock-out QPCTL mouse lines from a mutant mouse archive. The principal steps for the generation of a mutant mouse DNA and sperm archive, the isolation of gene-specific mutants from the archive and the generation of the mutant mouse line are shown.

(a) lane 1, purified human isoQC (500 ng); lane 2, cells transfected with human isoQC; lane 3, Media after human isoQC expression; lane 4, cells after transfection with human QC; lane 5, media after human QC expression; lane 6, cells after rat-isoQC expression; lane 7, media after rat-isoQC expression; lane 8, cells after rat QC expression; lane 9, media after rat QC expression. Protein detection using the specific human isoQC antibody pAb 3284.

(b) Development of the western blot after washing with Restore™ Western Blot Stripping Buffer (Thermo Scientific) with specific human QC antibody (pAb 8695)

Figure 17:
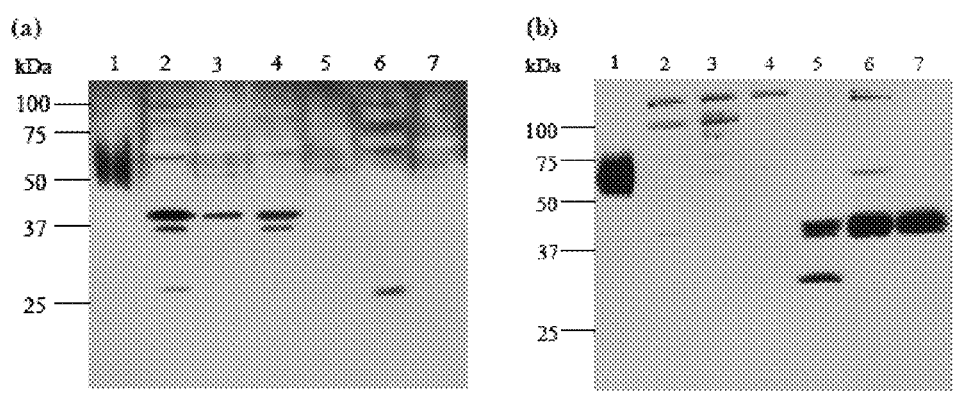

FIG. 17 shows the determination of basal expression levels of isoQC in cells from different mammalian species by western blot analysis. 120 µg protein from the disrupted cells was loaded to the SDS-Gel lane 1, purified human isoQC (10 ng); lane 2, HEK293 (human); lane 3, SH-SY5Y (human); lane 4, U343 (human); lane 5, RAW (mouse); lane 6, N2a (mouse); lane 7, PC12 (rat).

(a) Detection of the protein with human isoQC antibody pAb 3284.

(b) Detection of the proteins with rat-isoQC antibody pAb 3286

FIG. 18 (a) shows the effect of the QC/isoQC inhibitor (1-(1H-benzo[d]imidazol-5-yl)-5-(4-propoxyphenyl)imidazolidine-2,4-dione on monocyte infiltration in thioglycollate-induced peritonitis (mean±SEM, n>5 per group). Thioglycollate (TG) and inhibitor were applied by ip injection. Cells positive for surface marker 7/4 (7/4(high)) and possessing only a weak immunoreactivity for marker Ly6G (Ly6G(low)) represent the infiltrated monocyte population. The positive cell population was counted by cytofluorometry using true count beads (BD). (b) shows the determination of the MCP-1 N1pE concentration in the lavage fluid of the mice injected with thioglycollate and treated with different doses of isoQC-I compared to control animals and animals injected with thioglycollate alone.

FIG. 19 shows the infiltration of monocytes (a) and granulocytes (b) in mixed male/female homozygous (HOM) QPCTL knock out animals in comparison to mixed male/female wild type littermates (WT). Animals were injected with thioglycollate (Thio) or saline (PBS). (***, P<0.001; ANOVA followed by Tuckey post-hoc analysis).

Figure 20:
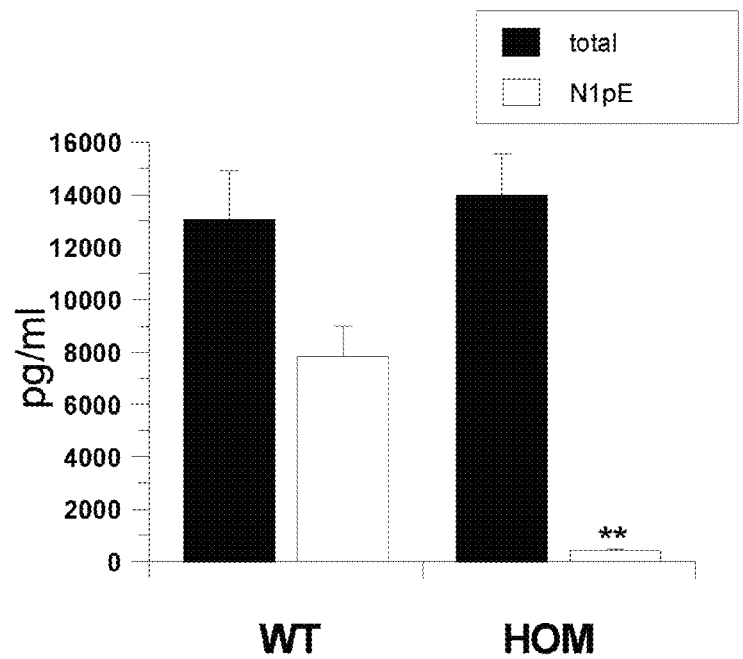

FIG. 20 shows the analysis of total MCP-1 (black bars) and pGlu-MCP-1 (open bars) using specific ELISAs in thioglycollate-injected mixed male/female homozygous (HOM) QPCTL k.o. animals compared to mixed male/female wild type littermates (WT). (**, P<0.01, Student's t-test).

Figure 21:
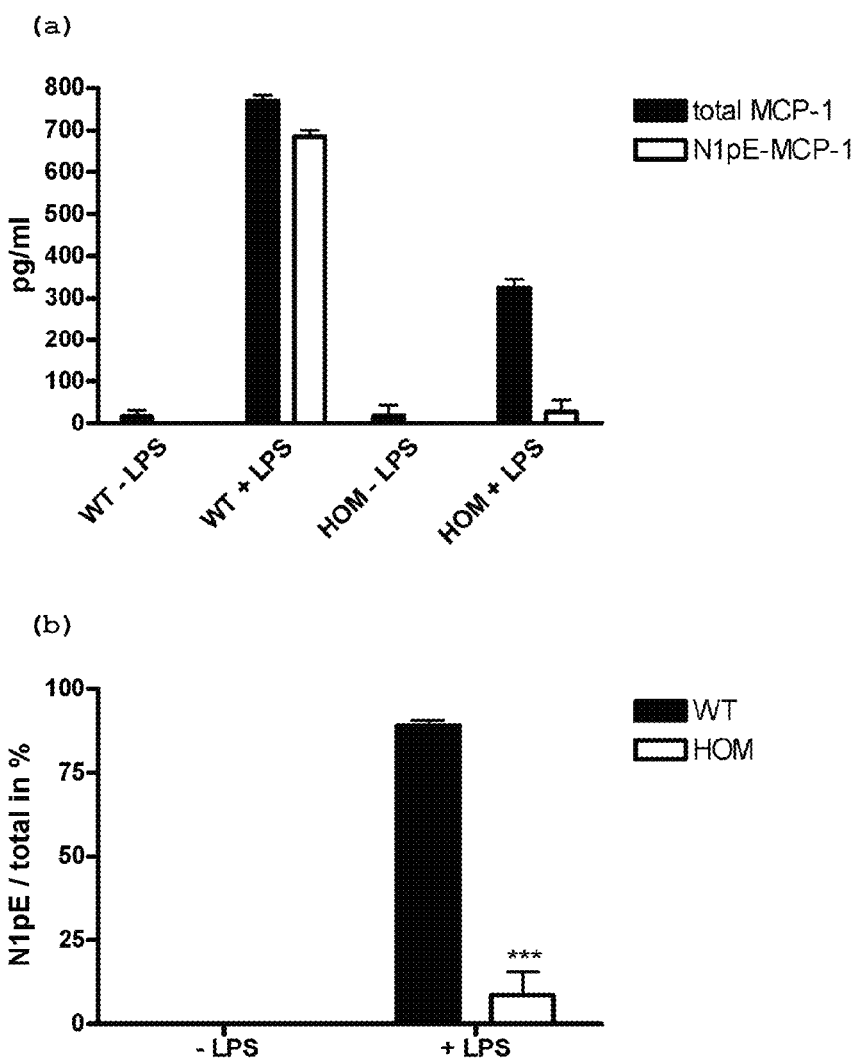

FIG. 21 (a) shows the analysis of total MCP-1 (black bars) and pGlu-MCP-1 (open bars) using specific ELISAs in LPS-stimulated PBMC (+LPS) compared to unstimulated PBMCs (−LPS) isolated from QPCTL k.o. animals (HOM) and wild type littermates (WT). (b) shows the ratio of pGlu-MCP-1 and total MCP-1 in % from QPCTL k.o. animals (open bars) and wild type littermates (black bars) in absence (−LPS) or presence (+LPS) of LPS-stimulus (***, P<0.001; 2-way ANOVA, followed by Bonferroni's post-hoc test).

FIG. 22 (a) shows the reactivation of mouse-isoQC, mouse QC and QC from *Drosophila melanogaster* (DromeQC) with different ratios of zinc to enzyme. Prior to reactivation, enzymes were inactivated with 1,10-phenantroline in 50 mM BisTris, pH 6.8 containing 500 mM NaCl to a residual activity under 1%. Subsequently, the enzyme was subjected to dialysis against 50 mM BisTris, pH 6.8 containing 500 mM NaCl and 50 g/l Chelex. Reactivation was carried out by addition of different concentrations of ZnSO$_4$ to the inactivated proteins. b) Reactivation of mouse-isoQC with zinc ions, the protein to zinc content was increasing in order to determine the zinc necessary to fully reactivate the enzyme. Inactivation was carried out with 1,10-phenantroline in 50 mM BisTris, pH 6.8 containing 500 mM NaCl.

Figure 23:
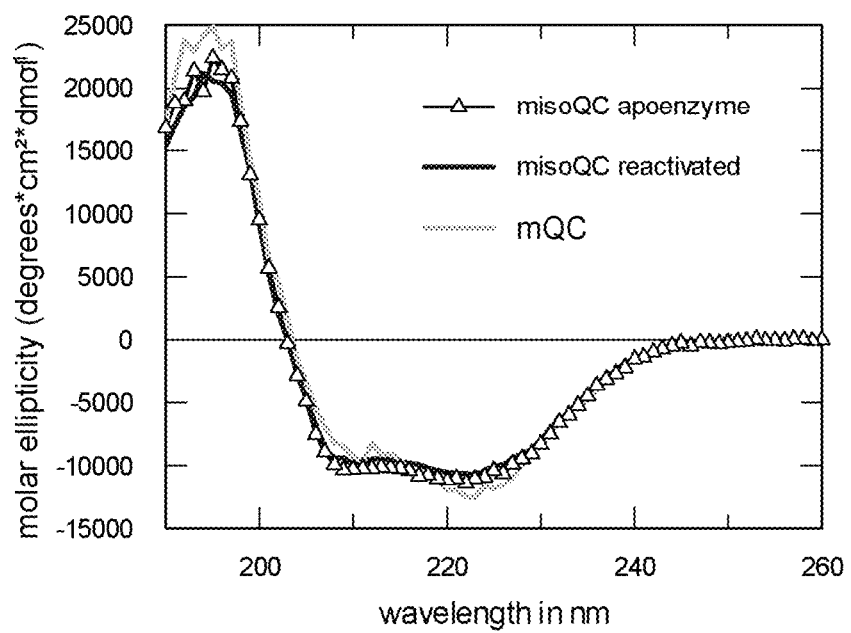

FIG. 23 shows a CD-spectroscopic analysis of the secondary structure of inactivated and reactivated mouse isoQC. The protein was dissolved in 10 mM potassium phosphate buffer, pH 6.8. An estimation of the secondary structure revealed 50% α-helix and 26% β-turn for both enzymes. The zinc ion does not exert an influence on the secondary structure.

Figure 24:
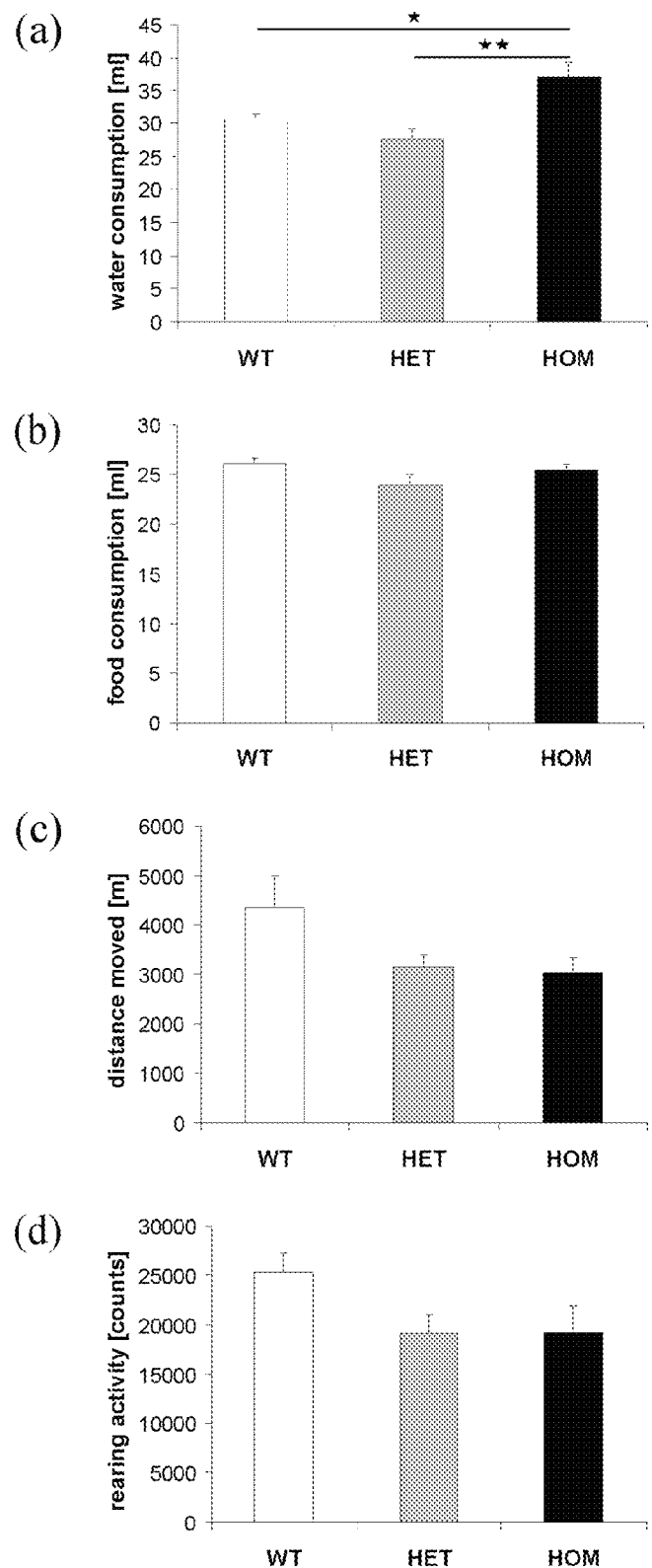

FIG. 24 shows the results of automated home cage behavior analysis using a PhenoMaster system. (a) Water and (b) food consumption, as well as (c) locomotor activity in the x/y-level and (d) rearing activity of wildtype, heterozygous and homozygous QPCTL knockout male mice aged 7 months are shown as means+SEM (*, p<0.05; **, p<0.01; One-way ANOVA followed by Newman-Keuls post-hoc analysis).

Figure 25:
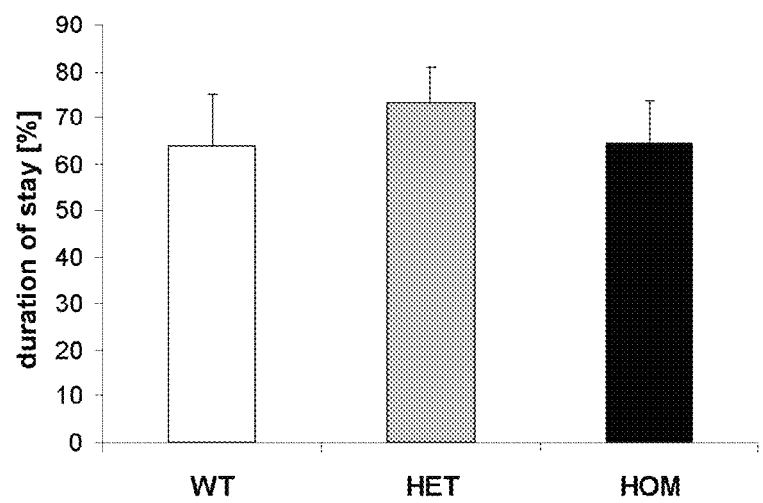

FIG. 25 shows the duration of stay (mean+SEM) in the light compartment in the dark-light box test of wildtype, heterozygous and homozygous QPCTL knockout male mice aged 7 months.

FIG. 26 shows the performance of wildtype, heterozygous and homozygous QPCTL knockout males aged 7 months on the pole as (a) t-turn (time to turn around) and (b) t-total (total time to climb down) latencies in the best out of five trials (mean+SEM).

FIG. 27 shows the performance of wildtype, heterozygous and homozygous QPCTL knockout males aged 7 months on the accelerating rotarod (4 to 40 rpm in 300 seconds) as total distance moved (mean+SEM): (a) best trial analysis out of nine trials, (b) trial progression.

Figure 28:
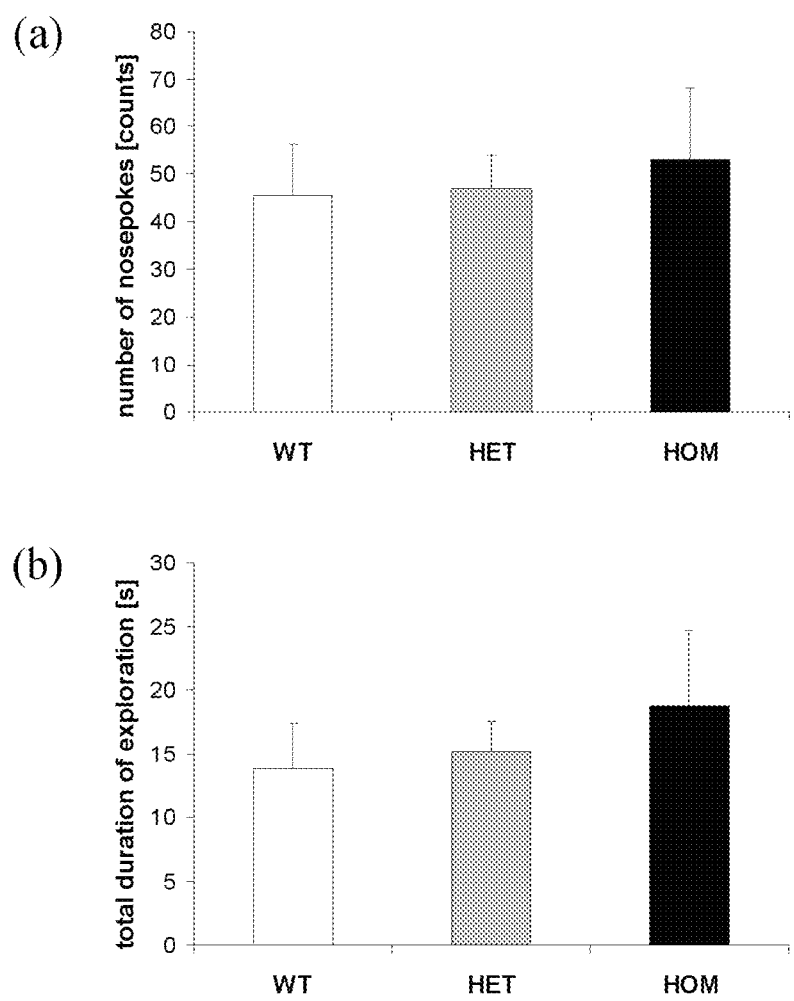

FIG. 28 shows the results of the holeboard test of wildtype, heterozygous and homozygous QPCTL knockout male mice aged 7 months. (a) Numbers of nosepokes and (b) total duration of hole explorations are shown as means+SEM.

Figure 29:
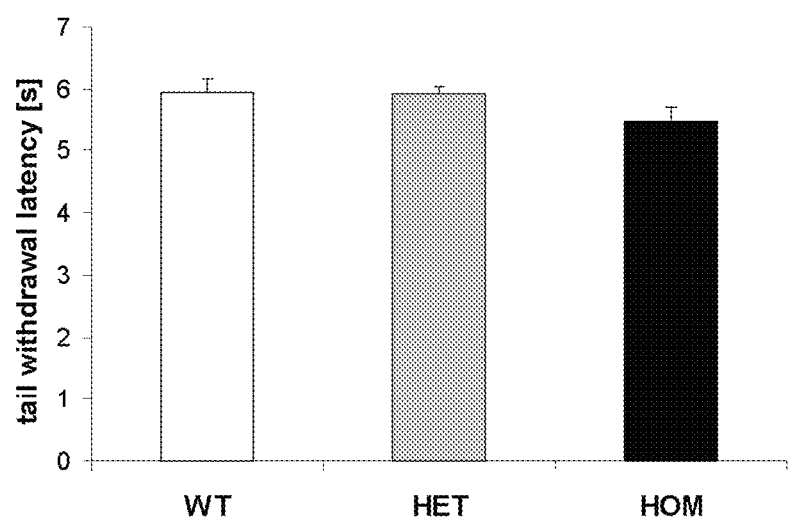

FIG. 29 shows the tail withdrawal latency (mean+SEM) in the tail flick test of wildtype, heterozygous and homozygous QPCTL knockout male mice aged 7 months.

Figure 30:
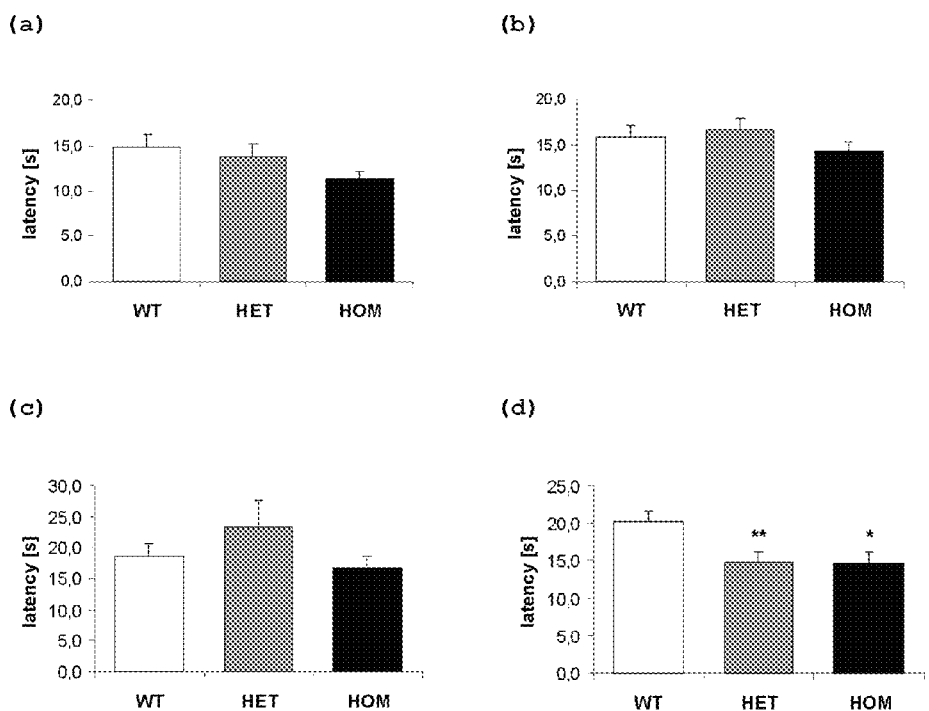

FIG. 30 shows the paw withdrawal latency of wildtype, heterozygous and homozygous QPCTL knockout animals on the constant hotplate (52.5° C.+/−0.2; cutoff 60 seconds) as mean+SEM: (a) non-adapted and (b) adapted trial of males aged 7 months, (c) non-adapted trial of young males aged 7 weeks and (d) non-adapted trial of young females aged 7 weeks (*, p<0.05; **, p<0.01; One-way ANOVA, followed by Newman-Keuls post-hoc test).

Figure 31:
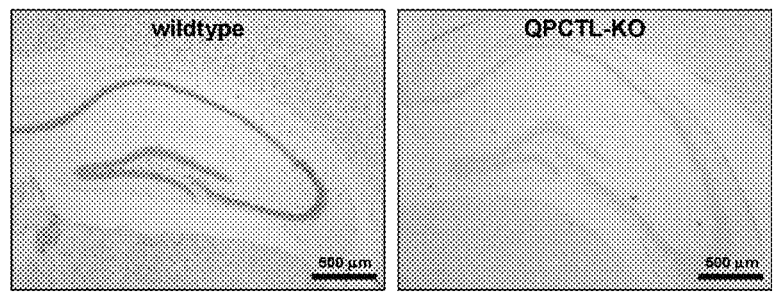

FIG. 31 shows immunohistochemical staining of coronal sections of the hippocampus of wildtype and QPCTL knock-out mice with QPCTL antibody (sclae bars: 500 µm).

Figure 32:
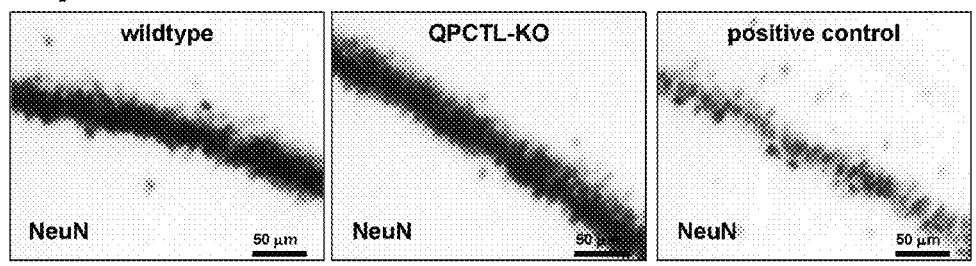

FIG. 32 shows immunohistochemical staining of coronal sections of the hippocampal CA1 region of wildtype, QPCTL knockout, and positive control mice with NeuN antibody (sclae bars: 50 µm).

Figure 33:
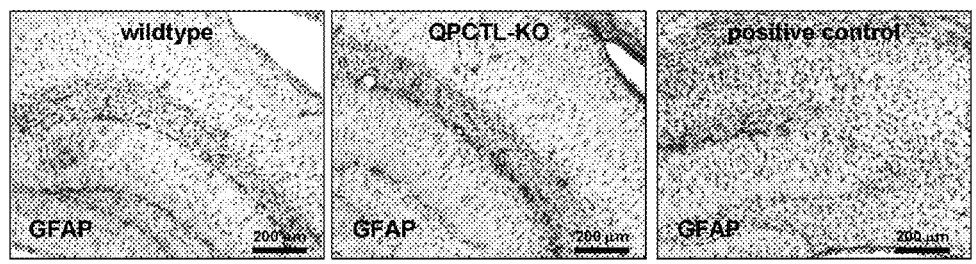

FIG. 33 shows immunohistochemical staining of coronal sections of the hippocampus of wildtype, QPCTL knockout, and positive control mice with GFAP antibody (sclae bars: 200 µm).

Figure 34:
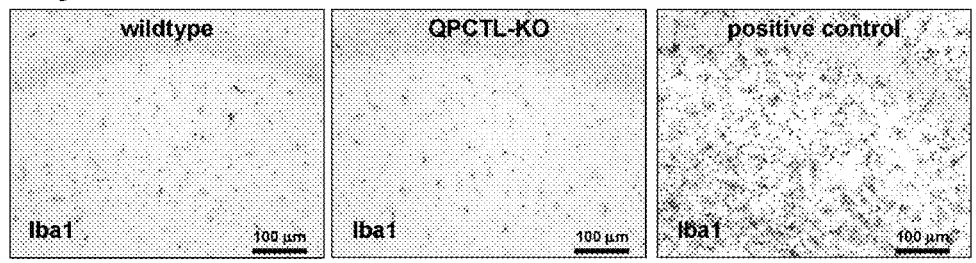

FIG. 34 shows immunohistochemical staining of coronal sections of the hippocampal CA1 region of wildtype, QPCTL knockout, and positive control mice with Iba1 antibody (sclae bars: 100 µm).

Figure 35:
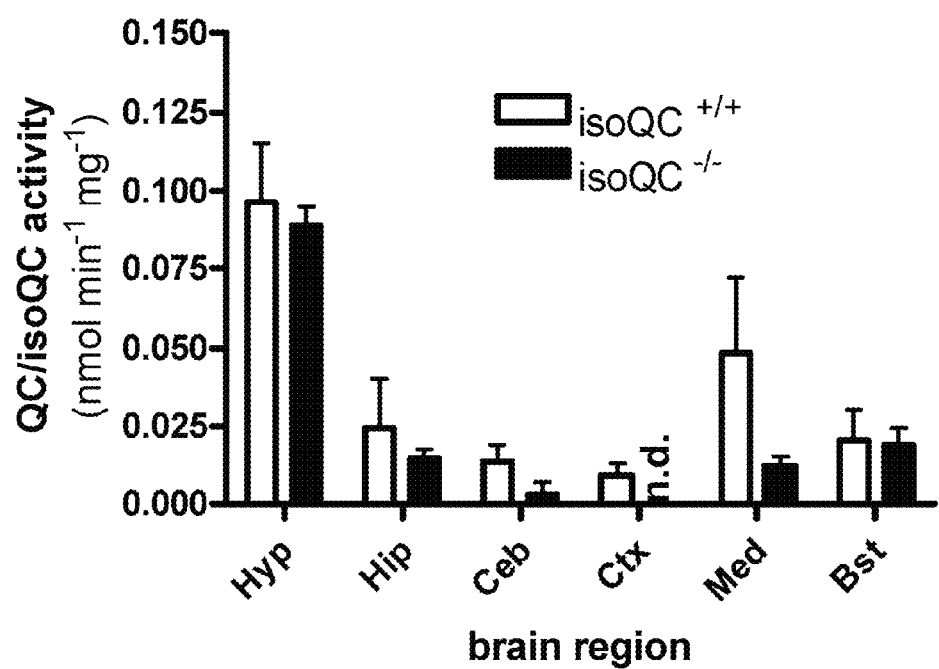

FIG. 35 shows the specific glutaminyl cyclase activity in brain different tissue of isoQC knock-out mice ($QC^{-/-}$) or wildtype ($QC^{+/+}$) littermates, which due to conversion of Gln-β-naphthylamine by QC and isoQC. Abbreviations are: Abbreviations are: Hyp, hypothalamus; Hip, Hippocampus; Ceb, Cerebellum; Ctx, Cortex; Med, Medulla; Bst, brainstem.

| List of Sequences | |
| --- | --- |
| SEQ ID NO | Description |
| 1 | Murine QPCTL, nucleic acid |
| 2 | Murine QPCTL, protein |
| 3 | Murine QPCTL, isoform, protein |
| 4 | Rat QPCTL, nucleic acid |
| 5 | Rat QPCTL, protein |
| 6 | Human QPCTL, nucleic acid |
| 7 | Human QPCTL, protein |
| 8 | QPCTL-7, PCR primer |
| 9 | QPCTL-8, PCR primer |
| 10 | Murine QPCTL knock-out, PCR fragment |
| 11 | Murine isoQC Met II, nucleic acid |
| 12 | Rat isoQC Met II, nucleic acid |

-continued

List of Sequences

| SEQ ID NO | Description |
|---|---|
| 13 | Murine isoQC Met II, protein |
| 14 | Rat isoQC Met II, protein |
| 15 | Sense primer for cloning of EGFP-tagged rat and mouse isoQC |
| 16 | Antisense primer for cloning of EGFP-tagged rat and mouse isoQC |
| 17 | Sense primer for amplification of mouse-isoQC cDNA starting with MetI |
| 18 | Antisense primer for amplification of mouse isoQC cDNA starting with MetI or Met II |
| 19 | Sense primer for amplification of mouse isoQC and rat isoQC cDNA starting with MetII |
| 20 | Sense primer for amplification of rat isoQC cDNA starting with MetI |
| 21 | Antisense primer for amplification of rat isoQC cDNA starting with MetI or Met II |
| 22 | Antisense primer for amplification of murine isoQC N-terminal sequence |
| 23 | Antisense primer for amplification of rat isoQC N-terminal sequence |
| 24 | forward primer for the amplification of murine QPCT |
| 25 | forward primer for the amplification of murine QPCT |
| 26 | forward primer for the amplification of murine QPCT |
| 27 | reverse primer for the amplification of murine QPCT |
| 28 | reverse primer for the amplification of murine QPCT |
| 29 | reverse primer for the amplification of murine QPCT |
| 30 | reverse primer for the amplification of murine QPCT |
| 30 | reverse primer for the amplification of murine QPCT |
| 32 | reverse primer for the amplification of murine QPCT |
| 33 | reverse primer for the amplification of murine QPCT |
| 34 | reverse primer for the amplification of murine QPCT |
| 35 | forward primer for the amplification of murine QPCTL |
| 36 | reverse primer for the amplification of murine QPCTL |
| 37 | Sense primer for amplification of murine isoQC starting with Glu 43 |
| 38 | antisense primer for amplification of murine isoQC for insertion into pPICZαA vector |
| 39 | sense primer for introduction of a Ile 56 to Asn mutation in murine isoQC |
| 40 | antisense primer for introduction of a Ile 56 to Asn mutation in murine isoQC |

Other objects, advantages and features of the invention will become apparent upon consideration of the following detailed description.

DETAILED DESCRIPTION OF THE PRESENTLY PREFERRED EMBODIMENTS

The present invention pertains to
1. A non-human animal comprising cells containing a DNA QPCTL gene carrying a knock-out mutation.
2. The non-human animal of item 1, wherein the QPCTL gene is of murine origin.
3. The non-human animal of items 1 or 2, wherein the animal is heterozygous for the knock-out mutation in the QPCTL gene.
4. The non-human animal of items 1 or 2, wherein the animal is homozygous for the knock-out mutation in the QPCTL gene.
5. The non-human animal of any of items 1 to 4, wherein the animal is a mouse.
6. The non-human animal of any of items 1 to 4, wherein the animal is a rat.
7. The non-human animal of any of items 1 to 4, wherein the QPCTL gene is of human origin.
8. The non-human animal of any of items 1 to 7, wherein the QPCTL gene is a recombinant gene.
9. The non-human animal of any of items 1 to 8, wherein the QPCTL gene carries a constitutive knock-out mutation.
10. The non-human animal of any of items 1 to 9, wherein the animal carries at least one QPCTL allele where the QPCTL gene carries a Thymidine to Adenosine (T->A) nucleotide substitution at nucleotide position 442 in the reference sequence NM_026111 of SEQ ID NO. 1, leading to the introduction of a stop codon into the QPCTL open reading frame.
11. The non-human animal of item 10, wherein the animal is a mouse of the mouse line QPCTL_L144X.
12. The non-human animal of any of items 1 to 9, wherein the QPCTL gene carries at least one mutation, which results in the mutation of at least one amino residue that is responsible for complexation of the catalytic active zinc ion.
13. The non-human animal of item 12, wherein the mutation in the QPCTL gene results in the mutation of at least one amino acid residue selected from of Asp187, Glu227 and His 352.
14. The non-human animal according to any of items 1 to 13, wherein the animal demonstrates a phenotype that can be reversed or ameliorated with a QPCTL inhibitor.
15. The non-human animal of any of items 1 to 14, for use in determining effects of target compounds on QPCTL-related disorders and/or diseases.
16. Use of the non-human animal model according to any one of items 1 to 14 for the analysis of the physiological function of QPCTL in vivo.
17. A screening method for biologically active agents that inhibit or promote QPCTL activity in vivo, comprising:
    i. administering a test agent to a non-human animal bearing a QPCTL gene which carries a knock-out mutation, and
    ii. determining the effect of the agent.
18. A screening method for biologically active agents that inhibit or promote QPCTL activity in vivo, comprising:
    i) administering a test agent to a disease-specific non-human animal model,
    ii) determining the effect of the test agent;
    iii) comparing the effect of the test agent with the effect of the QPCTL gene knock-out in the QPCTL knock-out animal models, and
    iv) selecting test agents that have an efficacy similar to the effect of the QPCTL gene knock-out on the specific disease.
19. The screening method of item 17 or 18, wherein the test agent is an inhibitor of QPCTL.
20. The screening method of item 18 or 19, wherein said disease specific non-human animal model is specific for a disease selected from the group consisting of Mild Cognitive Impairment, Alzheimer's disease, neurodegeneration in Down Syndrome, Familial Danish Dementia and Familial British Dementia.
21. The screening method of item 20, wherein said disease-specific non-human animal model is specific for Alzheimer's disease.
22. The screening method according to any one of items 18 to 21, wherein said Alzheimer's disease animal model is selected from the group consisting of PDAPP, Tg2576, APP23, TgCRND8, $PSEN_{1M146V}$ or $PSEN_{1M146L}$, PSAPP, $APP_{Dutch}$, BRI-Aβ40 and BRI-Aβ42, JNPL3, $Tau_{P301S}$, $Tau_{V337M}$, $Tau_{R406W}$, rTg4510, $H_{tau}$, TAPP and 3×TgAD and non-human transgenic animal models, wherein the transgene encodes at least one amyloid beta (Aβ) peptide selected from the group consisting of AβN3E-42, AβN3Q-42, AβN3E-40 and AβN3Q-40.
23. The screening method according to any one of items 18 to 22, wherein the effect of the test agents is the inhibition of the formation of [pGlu³]Aβ3-40/42/or [pGlu¹¹]Aβ11-40/42/peptides in at least one Alzheimer's disease animal model of item 20.
24. The screening method according to any one of items 18 to 23, wherein the effect of the test agents is the inhibition of the formation of [pGlu³]Aβ3-40 peptides in at least one Alzheimer's disease animal model of item 20.
25. The screening method according to any of items 18 to 23, wherein the effect of the test compounds is the inhibition of the formation of [pGlu³]Aβ3-42 peptides in at least one Alzheimer's disease animal model of item 20.
26. The screening method of item 18 or 19, wherein said disease-specific non-human animal model is specific for an inflammatory disease selected from the group consisting of:
    i) chronic and acute inflammations, e.g. rheumatoid arthritis, atherosclerosis, restenosis, pancreatitis,
    ii) other inflammatory diseases, e.g. neuropathic pain, graft rejection/graft failure/graft vasculopathy, HIV infections/AIDS, gestosis, tuberous sclerosis, Guillain-Barré syndrome, chronic inflammatory demyelinising polyradiculoneuropathy and multiple sclerosis, and
    iii) neuroinflammation.
27. The screening method of item 26, wherein said disease-specific non-human animal model is specific for rheumatoid arthritis.
28. The screening method of item 26, wherein said disease-specific non-human animal model is specific for atherosclerosis.
29. The screening method of item 26, wherein said disease-specific non-human animal model is specific for restenosis.
30. The screening method of item 26, wherein said disease-specific non-human animal model is specific for multiple sclerosis.
31. The screening method of item 26, wherein said disease-specific non-human animal model is specific for neuroinflammation.
32. The screening method according to any one of items 18 and 26 to 29, wherein said disease-specific animal model is selected from the group consisting of the apolipoprotein E knock-out mouse model, the thioglycollate-induced inflammation model in mice, the collagen-induced arthritis model in rat, the antibody induced arthritis model in rat and rat models of restenosis.
33. The screening method according to any one of items 18 and 26 to 30, wherein the effect of the test compounds is an inhibition of the chemotaxis of THP-1 cells.
34. The screening method according to any one of items 18 and 26 to 31, wherein the effect of the test compounds is an inhibition of the formation of at least one of pGlu-MCP-1, pGlu-MCP-2, pGlu-MCP-3 and pGlu-MCP-4.
35. A method for screening for biologically active agents that selectively inhibit or promote QC activity in vivo comprising:
    i) administering a test agent to a non-human animal model bearing a QPCTL gene which carries a knock-out mutation,
    ii) determining the effect of the test agent on the QC activity in vivo;
    iii) comparing the effect of the test agent on the in vivo QC activity with the in vivo QC activity in non-human QPCTL knock-out animals, which have received placebo, and
    iv) selecting test agents that have an inhibitory or promoting effect on QC activity in vivo.
36. The screening method of item 35, wherein the test agent is a selective inhibitor of QC.
37. The screening method according to any one of items 17 to 36, wherein the non-human animal is heterozygous for the QPCTL gene.
38. The screening method according to any one of items 17 to 36, wherein the non-human animal is homozygous for the QPCTL gene.
39. The screening method according to any one of items 17 to 38, wherein the animal is a mouse.
40. The screening method according to any one of items 17 to 38, wherein the animal is a rat.
41. The screening method according to any one of items 17 to 40, wherein the QPCTL gene is of murine origin.
42. The screening method according to any one of items 17 to 40, wherein the QPCTL gene is of human origin.
43. The screening method according to any one of items 17 to 42, wherein the QPCTL gene is a recombinant gene.
44. The screening method according to item 43, wherein the recombinant QPCTL gene carries a constitutive knock-out mutation.
45. The screening method according to any one of items 17 to 44, wherein the non-human animal carries at least one QPCTL allele where the QPCTL gene carries a Thymidine to Adenosine (T->A) nucleotide substitution at nucleotide position 442 in the reference sequence NM_026111 of SEQ ID NO. 1, leading to the introduction of a stop codon into the QPCTL open reading frame.
46. The screening method according to item 45, wherein the non-human animal is a mouse of the mouse line QPCTL_L144X.
47. The screening method according to any of items 17 to 44, wherein the non-human animal carries at least one mutation in the QPCTL gene, which results in the mutation of at least one amino residue that is responsible for complexation of the catalytic active zinc ion.
48. The screening method of item 47, wherein said mutation in the QPCTL gene results in the mtation of at least one amino acid residue selected from Asp187, Glu227 and His352.
49. The screening method according to any one of items 17 to 48, wherein the QPCTL gene is operably linked to a tissue-specific promoter.
50. The screening method according to any one of items 17 to 49, wherein the non-human animal model demonstrates a phenotype that can be reversed or ameliorated with a QPCTL inhibitor.
51. The screening method according to any one of items 17 to 50 for use in target drug discovery.
52. A cell or cell line containing a DNA QPCTL gene carrying a knock-out mutation, wherein said cell or cell line is derived from the non-human animal according to any of items 1 to 14.
53. A method of treatment or prevention of a QPCTL-related disease comprising
    i) administering a test agent as selected according to any of items 18 to 50 to a subject in need thereof; and
    ii) monitoring the subject for a decreased clinical index for QPCTL-related diseases.
54. Use of a test agent as selected according to any of items 18 to 50 for the preparation of a medicament for the treatment and/or prevention of a QPCTL-related disease.
55. The use or method of item 53 or 54, wherein said QPCTL-related disease is selected from the group consisting of Mild Cognitive Impairment, Alzheimer's disease, neurodegeneration in Down Syndrome, Familial Danish Dementia and Familial British Dementia.
56. The use or method of item 53 or 54, wherein said QPCTL-related disease is Alzheimer's disease.

57. The use or method of item 53 or 54, wherein said QPCTL-related disease is selected from the group consisting of:
   iv) chronic and acute inflammations, e.g. rheumatoid arthritis, atherosclerosis, restenosis, pancreatitis,
   v) other inflammatory diseases, e.g. neuropathic pain, graft rejection/graft failure/graft vasculopathy, HIV infections/AIDS, gestosis, tuberous sclerosis, Guillain-Barré syndrome, chronic inflammatory demyelinising polyradiculoneuropathy and multiple sclerosis, and
   vi) neuroinflammation.
58. The use or method of item 53 or 54, wherein said QPCTL-related disease is rheumatoid arthritis.
59. The use or method of item 53 or 54, wherein said QPCTL-related disease is atherosclerosis.
60. The use or method of item 53 or 54, wherein said QPCTL-related disease is restenosis.
61. The use or method of item 53 or 54, wherein said QPCTL-related disease is multiple sclerosis.
62. The use or method of item 53 or 54, wherein said QPCTL-related disease is neuroinflammation.
63. A method for analysing the disease-related physiological function of QPCTL catalysis with regard to pyroglutamate-peptide formation comprising
   i) evaluating the pyroglutamate-peptide amount in the non-human animal of any of items 1 to 14,
   ii) evaluating the pyroglutamate-peptide amount in the wild-type non-human animal, which does not bear the QPCTL gene disruption,
   iii) calculating differences in the pyroglutamate-peptide amount in the non-human animal of any of items 1 to 14 and the pyroglutamate-peptide amount in the wild-type non-human animal, and
   iv) evaluating the effects of an increased or decreased pyroglutamate-peptide amount on the phenotype of the non-human animal of any of items 1 to 14.
64. The method of item 63, wherein the pyroglutamate-peptide amount in the non-human animal of any of items 1 to 14 is decreased.
65. The method of item 63, wherein the amount of at least one of the [pGlu$^3$]Aβ3-40/42/or [pGlu$^{11}$]Aβ11-40/42/peptides is decreased in the non-human animal of any of items 1 to 14.
66. The method of item 63, wherein the amount of the [pGlu$^3$]Aβ3-40 peptide is decreased in the non-human animal of any of items 1 to 14.
67. The method of item 63, wherein the amount of the [pGlu$^3$]Aβ3-42 peptide is decreased in the non-human animal of any of items 1 to 14.
68. The method of item 63, wherein the amount of at least one of the pGlu-MCP-1, pGlu-MCP-2, pGlu-MCP-3 and pGlu-MCP-4 peptides is decreased in the non-human animal of any of items 1 to 14.
69. Use of the method of item 63 for the identification of a new medical target, which can be influenced by the administration of effectors that either promote or inhibit QPCTL activity.
70. The use of item 69, wherein the new medical target is influenced by inhibition of the QPCTL activity.
71. Use of the non-human animal according to any of items 1 to 14 or the cell according to item 52 for the provision of models with QPCTL expression in specific tissue and/or particular points in time only.
72. A pharmaceutical composition comprising the selected test agent according to any of items 17 to 50.

Definitions

The term "knock-out animal" means a non-human animal, usually a mammal, which carries one or more genetic manipulations leading to deactivation of one or more genes.

The term "construct" means a recombinant nucleic acid, generally recombinant DNA, that has been generated for the purpose of the expression of a specific nucleotide sequence(s), or is to be used in the construction of other recombinant nucleotide sequences. The recombinant nucleic acid can encode e.g. a chimeric or humanized polypeptide.

"Polypeptide" here pertains to all possible amino acid sequences comprising more than 10 amino acids.

The term "operably linked" means that a DNA sequence and (a) regulatory sequence(s) are connected in such a way as to permit gene expression when the appropriate molecules (e.g., transcriptional activator proteins) are bound to the regulatory sequence(s).

The term "operatively inserted" means that a nucleotide sequence of interest is positioned adjacent a nucleotide sequence that directs transcription and translation of the introduced nucleotide sequence of interest.

Knock-Out Genes

The QPCTL polynucleotides comprising the gene of the present invention include QPCTL (c)DNA and shall also include modified QPCTL (c)DNA. As used herein, a "modification" of a nucleic acid can include one or several nucleotide additions, deletions, or substitutions with respect to a reference sequence. A modification of a nucleic acid can include substitutions that do not change the encoded amino acid sequence due to the degeneracy of the genetic code, or which result in a conservative substitution. Such modifications can correspond to variations that are made deliberately, such as the addition of a Poly A tail, or variations which occur as mutations during nucleic acid replication.

As employed herein, the term "substantially the same nucleotide sequence" refers to DNA having sufficient identity to the reference polynucleotide, such that it will hybridize to the reference nucleotide under moderately stringent, or higher stringency, hybridization conditions. DNA having "substantially the same nucleotide sequence" as the reference nucleotide sequence can have an identity ranging from at least 60% to at least 95% with respect to the reference nucleotide sequence.

The phrase "moderately stringent hybridization" refers to conditions that permit a target-nucleic acid to bind a complementary nucleic acid. The hybridized nucleic acids will generally have an identity within a range of at least about 60% to at least about 95%. Moderately stringent conditions are conditions equivalent to hybridization in 50% formamide, 5×Denhart's solution, 5×saline sodium phosphate EDTA buffer (SSPE), 0.2% SDS (Aldrich) at about 42° C., followed by washing in 0.2×SSPE, 0.2% SDS (Aldrich), at about 42° C.

High stringency hybridization refers to conditions that permit hybridization of only those nucleic acid sequences that form stable hybrids in 0.018M NaCl at about 65° C.; for example, if a hybrid is not stable in 0.018M NaCl at about 65° C., it will not be stable under high stringency conditions, as contemplated herein. High stringency conditions can be provided, for example, by hybridization in 50% formamide, 5×Denhart's solution, 5×SSPE, 0.2% SDS at about 42° C., followed by washing in 0.1×SSPE, and 0.1% SDS at about 65° C.

Other suitable moderate stringency and high stringency hybridization buffers and conditions are well known to those of skill in the art and are described, for example, in Sambrook et al. Molecular Cloning: A Laboratory Manual, 2nd ed., Cold Spring Harbor Press, Plainview, N.Y. (1989); and Ausubel et al. (Current Protocols in Molecular Biology (Supplement 47), John Wiley & Sons, New York (1999)).

The amino acid sequence encoded by the knock-out gene of the present invention can be a QPCTL sequence from a human or the QPCTL homologue from any species, preferably from a murine species. The amino acid sequence encoded by the knock-out gene of the present invention can also be a fragment of the QPCTL amino acid sequence as long as the fragment retains some or all of the function of the full-length QPCTL sequence. The sequence may also be a modified QPCTL sequence, encompassing individual substitutions, deletions or additions, which alter, add or delete a single amino acid or a small percentage of amino acids (typically less than 10%, more typically less than 5%, and still more typically less than 1%.) A "modification" of the amino acid sequence encompasses conservative substitutions of the amino acid sequence. Conservative substitution tables providing functionally similar amino acids are well known in the art. The following six groups each contain amino acids that are conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

Other minor modifications are included within the sequence as long as the polypeptide retains some or all of the structural and/or functional characteristics of a QPCTL polypeptide. Exemplary structural or functional characteristics include sequence identity or substantial similarity, antibody reactivity, the presence of conserved structural domains such as RNA binding domains or acidic domains.

DNA Constructs and Vectors

The invention further provides a DNA construct comprising the Qpctl knock-out gene as described above. As used herein, the term "DNA construct" refers to a specific arrangement of genetic elements in a DNA molecule. In addition to human QPCTL, or mutant forms thereof, the invention also provides a DNA construct using polypeptides from other species as well as QPCTL mutant non-human mammals expressing QPCTL from non-human species.

If desired, the DNA constructs can be engineered to be operatively linked to appropriate expression elements such as promoters or enhancers to allow expression of a genetic element in the DNA construct in an appropriate cell or tissue. The use of the expression control mechanisms allows for the targeted delivery and expression of the gene of interest. For example, the constructs of the present invention may be constructed using an expression cassette which includes in the 5'-3' direction of transcription, a transcriptional and translational initiation region associated with gene expression in brain tissue, DNA encoding a mutant or wild-type QPCTL protein, and a transcriptional and translational termination region functional in the host animal. One or more introns also can be present. The transcriptional initiation region can be endogenous to the host animal or foreign or exogenous to the host animal.

The DNA constructs described herein may be incorporated into vectors for propagation or transfection into appropriate cells to generate QPCTL overexpressing mutant non-human mammals and are also comprised by the present invention. One skilled in the art can select a vector based on desired properties, for example, for production of a vector in a particular cell such as a mammalian cell or a bacterial cell.

Vectors can contain a regulatory element that provides tissue specific or inducible expression of an operatively linked nucleic acid. One skilled in the art can readily determine an appropriate tissue-specific promoter or enhancer that allows expression of QPCTL polypeptides in a desired tissue. It should be noted that tissue-specific expression as described herein does not require a complete absence of expression in tissues other than the preferred tissue. Instead, "cell-specific" or "tissue-specific" expression refers to a majority of the expression of a particular gene of interest in the preferred cell type or tissue.

Any of a variety of inducible promoters or enhancers can also be included in the vector for expression of a QPCTL polypeptide or nucleic acid that can be regulated. Such inducible systems, include, for example, tetracycline inducible System (Gossen & Bizard (1992) Proc. Natl. Acad. Sci. U.S.A. 89, 5547-5551; Gossen et al. Science (1995) 268, 17664769; Clontech, Palo Alto, Calif.); metallothionein promoter induced by heavy metals; insect steroid hormone responsive to ecdysone or related steroids such as muristerone (No et al. (1996) Proc. Natl. Acad. Sci. U.S.A. 93, 3346-3351; Yao et al. (1993) Nature 366, 476-479; Invitrogen, Carlsbad, Calif.); mouse mammary tumor virus (MMTV) induced by steroids such as glucocorticoid and estrogen (Lee et al. (1981) Nature 294, 228-232; and heat shock promoters inducible by temperature changes; the rat neuron specific enolase gene promoter (Forss-Petter, et al. (1990)) Neuron 5, 197-197; the human β-actin gene promoter (Ray, et al. (1991) Genes and Development 5, 2265-2273); the human platelet derived growth factor B (PDGF-B) chain gene promoter (Sasahara, et al. (1991) Cell 64, 217-227); the rat sodium channel gene promoter (Maue, et al. (1990) Neuron 4, 223-231); the human copper-zinc superoxide dismutase gene promoter (Ceballos-Picot, et al. (1991) Brain Res. 552, 198-214); and promoters for members of the mammalian POU-domain regulatory gene family (Xi et al. (1989) Nature 340, 35-42).

Regulatory elements, including promoters or enhancers, can be constitutive or regulated, depending upon the nature of the regulation, and can be regulated in a variety of tissues, or one or a few specific tissues. The regulatory sequences or regulatory elements are operatively linked to one of the polynucleotide sequences of the invention such that the physical and functional relationship between the polynucleotide sequence and the regulatory sequence allows transcription of the polynucleotide sequence. Vectors useful for expression in eukaryotic cells can include, for example, regulatory elements including the CAG promoter, the SV40 early promoter, the cytomegalovirus (CMV) promoter, the mouse mammary tumor virus (MMTV) steroid-inducible promoter, Pgtf, Moloney marine leukemia virus (MMLV) promoter, thy-1 promoter and the like.

If desired, the vector can contain a selectable marker. As used herein, a "selectable marker" refers to a genetic element that provides a selectable phenotype to a cell in which the selectable marker has been introduced. A selectable marker is generally a gene whose gene product provides resistance to an agent that inhibits cell growth or kills a cell. A variety of selectable markers can be used in the DNA constructs of the invention, including, for example, Neo, Hyg, hisD, Gpt and Ble genes, as described, for example in Ausubel et al. (Current Protocols in Molecular Biology (Supplement 47), John Wiley & Sons, New York (1999)) and U.S. Pat. No. 5,981,830. Drugs useful for selecting for the presence of a selectable marker include, for example, G418 for Neo, hygromycin for Hyg, histidinol for hisD, xanthine for Gpt, and bleomycin for Ble (see Ausubel et al, supra, (1999); U.S. Pat. No. 5,981,830). DNA constructs of the invention can incorporate a positive selectable marker, a negative selectable marker, or both (see, for example, U.S. Pat. No. 5,981,830).

Non-Human Knock-Out Animals

The invention primarily provides a non-human knock-out animal whose genome comprises a knock-out QPCTL gene. The mutation can be introduced by any methods known to those skilled in the art. The mutation can be introduced by mutagenesis with a super mutagen chemical like N-ethyl-N-nitrosourea (ENU). ENU is an intercalating substance leading to the introduction of point mutations into the genome (Russel et al. (1979) Proc Natl Acad Sci U.S.A. 76, 5818-9). Male mice founders (G0) are subjected to ENU mutagenesis (Russel et al. (1982) Proc Natl Acad Sci U.S.A. 79, 3592-3; Hitotsumachi et al. (1985) Proc Natl Acad Sci U.S.A. 82, 6619-21). For generation of the first offspring generation (G1) G0 males are mated with females. Sperm of G1 males is frozen in individual sperm straws (Marschall & Hrabe de Angelis (1999) Trends Genet. 15, 128-31; Marschall and Hrabe de Angelis (2003) Methods Mol. Biol. 209, 35-50) and deposited. In parallel, the kidney, liver and spleen serves as a primary source for the generation of a corresponding DNA archive. With a 99% probability an archive of 17.000 samples is sufficient to recover 5 functional mutations in any given average sized gene. To identify mutations in a target gene the DNA archive is amplified with gene specific primers flanking the region of interest. To detect the heterozygous mutations several methods are known like temperature gradient electrophoresis or HPLC separation. Using temperature gradient electrophoresis, PCR products carrying a mutation are identified and subsequently sequenced by direct dideoxy sequencing. Once an interesting mutation is identified the corresponding sperm is subjected to an in vitro fertilisation (IVF) (Marschall & Hrabe de Angelis (1999) Trends Genet. 15, 128-31; Marschall and Hrabe de Angelis (2003) Methods Mol. Biol. 209, 35-50) using wildtype oocytes as oocytes donors. After embryo transfer (Marschall & Hrabe de Angelis (1999) Trends Genet. 15, 128-31; Marschall and Hrabe de Angelis (2003) Methods Mol. Biol. 209, 35-50) in recipient foster females, pregnancy is induced. 50% of the resulting offsprings harbors the heterozygous mutation, which can be identified by genotyping of DNA recovered from the tail tip of the animal. To produce a colony of animals, heterozygous animals are intercrossed to produce homozygous animals for further phenotyping.

The (mutated) DNA fragment can be integrated into the genome of an animal by any method known to those skilled in the art. The DNA molecule containing the desired gene sequence can be introduced into pluripotent cells, such as ES cells, by any method that will permit the introduced molecule to undergo recombination at its regions of homology. Techniques that can be used include, but are not limited to, calcium phosphate/DNA co-precipitates, microinjection of DNA into the nucleus, electroporation, bacterial protoplast fusion with intact cells, transfection, and polycations, (e.g., polybrene, polyornithine, etc.) The DNA can be single or double stranded DNA, linear or circular. (See for example, Hogan et al. Manipulating the Mouse Embryo: A Laboratory Manual Cold Spring Harbor Laboratory (1986); Hogan et al. Manipulating the Mouse Embryo: A Laboratory Manual, second ed., Cold Spring Harbor Laboratory (1994), U.S. Pat. Nos. 5,602, 299; 5,175,384; 6,066,778; 4,873,191 and 6,037,521; retrovirus mediated gene transfer into germ lines (Van der Putten et al. (1985)) Proc. Natl. Acad. Sci. U.S.A. 82, 6148-6152; gene targeting in embryonic stem cells (Thompson et al. (1989) Cell 56, 313-321); electroporation of embryos (Lo (1983) Mol. Cell. Biol. 3, 1803-1814); and sperm-mediated gene transfer (Lavitrano et al. (1989) Cell 57, 717-723)).

For example, the zygote is a good target for microinjection, and methods of microinjecting zygotes are well known (see U.S. Pat. No. 4,873,191).

Embryonal cells at various developmental stages can also be used to introduce genes for the production of knock-out animals. Different methods are used depending on the stage of development of the embryonal cell. Such transfected embryonic stem (ES) cells can thereafter colonize an embryo following their introduction into the blastocoele of a blastocyst-stage embryo and contribute to the germ line of the resulting chimeric animal (reviewed in Jaenisch (1988) Science 240, 1468-1474). Prior to the introduction of transfected ES cells into the blastocoele, the transfected ES cells can be subjected to various selection protocols to enrich the proportion of ES cells that have integrated into knock-out gene if the knock-out gene provides a means for such selection. Alternatively, PCR can be used to screen for ES cells that have integrated the knock-out.

In addition, retroviral infection can also be used to introduce knock-out genes into a non-human animal. The developing non-human embryo can be cultured in vitro to the blastocyst stage. During this time, the blastomeres can be targets for retroviral infection (Jaenisch (1976) Proc. Natl. Acad. Sci. U.S.A. 73, 1260-1264). Efficient infection of the blastomeres is obtained by enzymatic treatment to remove the zona pellucida (Hogan et al. supra, 1986). The viral vector system used to introduce the knock-out is typically a replication-defective retrovirus carrying the knock-out (Jahner et al. (1985) Proc. Natl. Acad. Sci. U.S.A. 82, 6927-6931; Van der Putten et al. (1985) Proc. Natl. Acad. Sci. U.S.A. 82, 6148-6152). Transfection is easily and efficiently obtained by culturing the blastomeres on a monolayer of virus-producing cells (Van der Putten, supra, 1985; Stewart et al. (1987) EMBO J. 6, 383-388). Alternatively, infection can be performed at a later stage. Virus or virus-producing cells can be injected into the blastocoele (Jahner D. et al. (1982) Nature 298, 623-628). Most of the founders will be mosaic for the knock-out gene since incorporation occurs only in a subset of cells, which form the knock-out animal. Further, the founder can contain various retroviral insertions of the knock-out gene at different positions in the genome, which generally will segregate in the offspring. In addition, knock-out genes may be introduced into the germline by intrauterine retroviral infection of the mid-gestation embryo (Jahner et al. supra, 1982). Additional means of using retroviruses or retroviral vectors to create knock-out animals known to those of skill in the art involve the micro-injection of retroviral particles or mitomycin C-treated cells producing retrovirus into the perivitelline space of fertilized eggs or early embryos (WO 90/08832 (1990); Haskell and Bowen (1995) Mal. Reprod. Dev. 40, 386).

Any other technology to introduce knock-out genes into a non-human animal, e.g. the knock-in or the rescue technologies can also be used to create the non-human animal models of the present invention. The knock-in technology is well known in the art as described e.g. in Casas et al. (2004) Am. J. Pathol. 165, 1289-1300.

Once the founder animals are produced, they can be bred, inbred, outbred, or crossbred to produce colonies of the particular animal. Examples of such breeding strategies include, but are not limited to: outbreeding of founder animals with more than one integration site in order to establish separate lines; inbreeding of separate lines in order to produce compound transgenics that express the transgene at higher levels because of the effects of additive expression of each transgene; crossing of heterozygous transgenic mice to produce mice homozygous for a given integration site in order to both augment expression and eliminate the need for screening of animals by DNA analysis; crossing of separate homozygous lines to produce compound heterozygous or homozygous lines; breeding animals to different inbred genetic backgrounds so as to examine effects of modifying alleles on expression of the transgene and the effects of expression.

The knock-out animals are screened and evaluated to select those animals having the phenotype of interest. Initial screening can be performed using, for example, Southern blot analysis or PCR techniques to analyze animal tissues to verify that integration of the knock-out gene has taken place. The level of mRNA expression of the knock-out gene in the tissues of the knock-out animals can also be assessed using techniques which include, but are not limited to, Northern blot analysis of tissue samples obtained from the animal, in situ hybridization analysis, and reverse transcriptase-PCR (rt-PCR). Samples of the suitable tissues can be evaluated immunocytochemically using antibodies specific for QPCTL or with a tag such as EGFP. The knock-out non-human mammals can be further characterized to identify those animals having a phenotype useful in the invention. In particular, knock-out non-human mammals overexpressing QPCTL can be screened using the methods disclosed herein. For example, tissue sections can be viewed under a fluorescent microscope for the presence of fluorescence, indicating the presence of the reporter gene.

Another method to affect tissue specific expression is via the use of tissue-specific promoters. Non-limiting examples of suitable tissue-specific promoters include the albumin promoter (liver-specific; Pinkert et al. (1987) Genes Dev. 1, 268-277); lymphoid-specific promoters (Calame and Eaton (1988) Adv. Immunol. 43, 235-275), in particular promoters of T-cell receptors (Winoto and Baltimore (1989) EMBO J. 8, 729-733) and immunoglobulins (Banerji et al. (1983) Cell 33, 729-740; Queen and Baltimore (1983) Cell 33, 741-748), neuron-specific promoters (e.g., the neurofilament promoter, the Thy-1 promoter or the Bri-protein promoter; Sturchler-Pierrat et al. (1997) Proc. Natl. Acad. Sci. U.S.A. 94, 13287-13292, Byrne and Ruddle (1989) PNAS 86, 5473-5477), pancreas-specific promoters (Edlund et al. (1985) Science 230, 912-916), cardiac specific expression (alpha myosin heavy chain promoter, Subramaniam, A, Jones W K, Gulick J, Wert S, Neumann J, and Robbins J. Tissue-specific regulation of the alpha-myosin heavy chain gene promoter in transgenic mice. (1991) J Biol. Chem. 266, 24613-24620), and mammary gland-specific promoters (e.g., milk whey promoter; U.S. Pat. No. 4,873,316 and European Application Publication No. 264,166).

Preferred herein is a non-human animal, wherein the non-human animal carries at least one QPCTL allele. In a more preferred embodiment, said non-human animal is a mouse or rat. In an even more preferred embodiment, said non-human animal is a mouse. Most preferred is a non-human animal, either a mouse or a rat, where the QPCTL gene carries a T to A nucleotide substitution at nucleotide position 442 in the reference sequence NM_026111 (SEQ ID NO. 1) leading to the introduction of a stop codon into the QPCTL open reading frame. Particularly preferred is a mouse of mouse line QPCTL L144X.

The invention further provides an isolated cell containing a DNA construct of the invention. The DNA construct can be introduced into a cell by any of the well-known transfection methods (Sambrook et al. Molecular Cloning: A Laboratory Manual, 2nd ed., Cold Spring Harbor Press, Plainview, N.Y. (1989); Ausubel et al. supra, (1999)). Alternatively, the cell can be obtained by isolating a cell from a mutant non-human mammal created as described herein. Thus, the invention provides a cell isolated from a QPCTL mutant non-human mammal of the invention, in particular, a mouse which carries a knock-out mutation in the QPCTL gene. Accordingly, the present invention provides a cell, which is isolated from a non-human mammal, wherein said cell carries a knock-out mutation in the QPCTL gene The cells can be obtained from a homozygous QPCTL mutant non-human mammal such as a mouse or a heterozygous QPCTL mutant non-human mammal such as a mouse.

Effectors

Effectors, as that term is used herein, are defined as molecules that bind to enzymes and increase (i.e. promote) or decrease (i.e. inhibit) their activity in vitro and/or in vivo. Some enzymes have binding sites for molecules that affect their catalytic activity; a stimulator molecule is called an activator. Enzymes may even have multiple sites for recognizing more than one activator or inhibitor. Enzymes can detect concentrations of a variety of molecules and use that information to vary their own activities.

Effectors can modulate enzymatic activity because enzymes can assume both active and inactive conformations: activators are positive effectors, inhibitors are negative effectors. Effectors act not only at the active sites of enzymes, but also at regulatory sites, or allosteric sites, terms used to emphasize that the regulatory site is an element of the enzyme distinct from the catalytic site and to differentiate this form of regulation from competition between substrates and inhibitors at the catalytic site (Darnell, J., Lodish, H. and Baltimore, D. 1990, Molecular Cell Biology 2"d Edition, Scientific American Books, New York, page 63).

Peptides

If peptides or amino acids are mentioned in the present invention, each amino acid residue is represented by a one-letter or a three-letter designation, corresponding to the trivial name of the amino acid, in accordance with the following conventional list:

| Amino Acid | One-Letter Symbol | Three-Letter Symbol |
| --- | --- | --- |
| Alanine | A | Ala |
| Arginine | R | Arg |
| Asparagine | N | Asn |
| Aspartic acid | D | Asp |
| Cysteine | C | Cys |
| Glutamine | Q | Gln |
| Glutamic acid | E | Glu |
| Glycine | G | Gly |
| Histidine | H | His |
| Isoleucine | I | Ile |
| Leucine | L | Leu |
| Lysine | K | Lys |
| Methionine | M | Met |
| Phenylalanine | F | Phe |
| Proline | P | Pro |
| Serine | S | Ser |
| Threonine | T | Thr |
| Tryptophan | W | Trp |
| Tyrosine | Y | Tyr |
| Valine | V | Val |

IsoQC or QPCTL

The terms "isoQC" or "QPCTL" as used herein are both intended to refer to the same and comprise isoglutaminyl cyclase (IsoQC), i.e. isoglutaminyl-peptide cyclotransferase. Preferably, the QPCTL as used herein is a mammalian QPCTL, more preferably a non-human QPCTL, most preferably a murine QPCTL.

In a further preferred embodiment, the QPCTL as used herein is one of SEQ ID NO's: 2, 5 and 7 from mouse, rat and human, respectively. Most preferred is the QPCTL from mouse of SEQ ID NO: 2

The terms "QC activity" or "isoQC activity" or "QPCTL activity" as used herein is defined as intramolecular cyclization of N-terminal glutamine residues into pyroglutamic acid (pGlu*) or of N-terminal L-homoglutamine or L-β-homoglutamine to a cyclic pyro-homoglutamine derivative under liberation of ammonia. See schemes 1 and 2.

Scheme 1: Cyclization of glutamine by QC and QPCTL

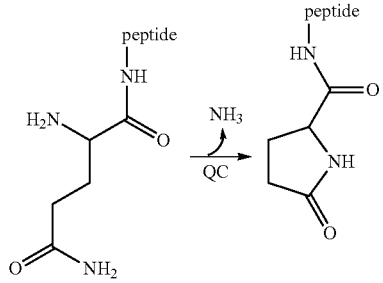

Scheme 2: Cyclization of L-homoglutamine by QC and QPCTL

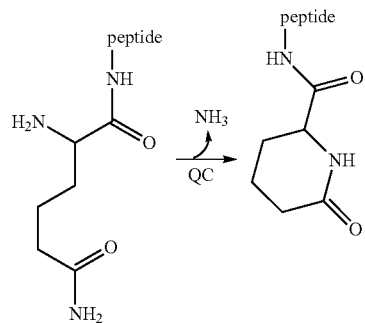

The term "EC" as used herein comprises the side activity of QPCTL as glutamate cyclase (EC), further defined as EC activity.

The term "EC activity" as used herein is defined as intramolecular cyclization of N-terminal glutamate residues into pyroglutamic acid (pGlu*) by QPCTL. See Scheme 3.

Scheme 3: N-terminal cyclization of glutamyl peptides by QC or QPCTL

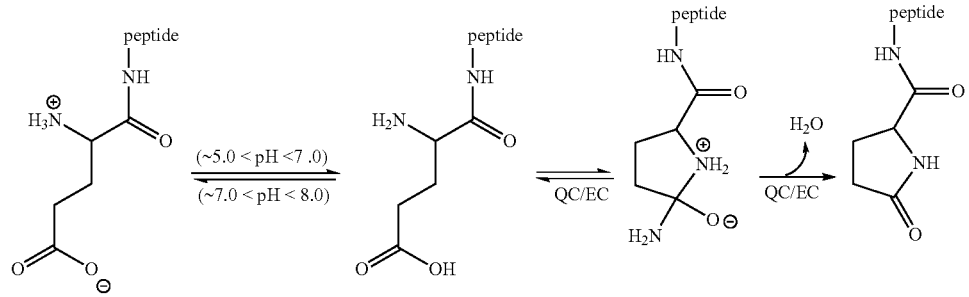

The term "metal-dependent enzyme" as used herein is defined as enzyme(s) that require a bound metal ion in order to fulfil their catalytic function and/or require a bound metal ion in order to form the catalytically active structure.

The term "(iso)QC-inhibitor" or "(iso)glutaminyl cyclase inhibitor" or "QPCT inhibitor" or "QPCTL inhibitor" is generally known to a person skilled in the art and means enzyme inhibitors, which inhibit the catalytic activity of glutaminyl cyclase (QPCT) or of the iso-glutaminyl cyclase enzymes (QPCTLs) or their glutamyl cyclase (EC) activity, preferably by direct interaction of the inhibitor with the respective enzyme.

The term "selective isoQC-inhibitor" as defined herein means enzyme inhibitors, which inhibit the catalytic activity of iso-glutaminyl cyclase (isoQC, QPCTL) but do not or with a lower potency inhibit the catalytic activity of glutaminyl cyclase (QC, QPCT). Preferred are selective isoQC-inhibitors, which inhibit iso-glutaminyl cyclase (isoQC) with a Ki-value, which is 10% lower than its Ki-value for the inhibition of glutaminyl cyclase (QC). More preferably, the Ki-value of said selective isoQC-inhibitor for the inhibition of iso-glutaminyl cyclase (isoQC, QPCTL) is 50% lower than its Ki-value for the inhibition of glutaminyl cyclase (QC). Even more preferred are selective isoQC-inhibitors, which inhibit iso-glutaminyl cyclase (isoQC) with a Ki-value, which is one order of magnitude lower than its Ki-value for the inhibition of gluaminyl cyclase (QC). More preferably, the Ki-value of said selective isoQC-inhibitor for the inhibition of iso-glutaminyl cyclase (isoQC, QPCTL) is two orders of magnitude lower than its Ki-value for the inhibition of gluaminyl cyclase (QC). Even more preferred are selective isoQC-inhibitors, wherein their Ki-value for the inhibition of iso-glutaminyl cyclase (isoQC, QPCTL) is three orders of magnitude lower than their Ki-value for the inhibition of gluaminyl cyclase (QC). Most preferred are selective isoQC-inhibitors, which do not inhibit glutaminyl cyclase (QC).

The term "selective QC-inhibitor" as defined herein means enzyme inhibitors, which inhibit the catalytic activity of glutaminyl cyclase but do not or with a lower potency inhibit the catalytic activity of iso-glutaminyl cyclase (isoQC, QPCTL). Preferred are selective QC-inhibitors, which inhibit glutaminyl cyclase (QC) with a Ki-value, which is 10% lower than its Ki-value for the inhibition of iso-glutaminyl cyclase (isoQC, QPCTL). More preferably, the Ki-value of said selective QC-inhibitor for the inhibition of glutaminyl cyclase (QC) is 50% lower than its Ki-value for the inhibition of iso-glutaminyl cyclase (isoQC, QPCTL). Even more preferred are selective QC-inhibitors, which inhibit glutaminyl cyclase (QC) with an Ki-value, which is one order of magnitude lower than its Ki-value for the inhibition of iso-glutaminyl cyclase (isoQC, QPCTL). More preferably, the Ki-value of said selective QC-inhibitor for the inhibition of glutaminyl cyclase (QC) is two orders of magnitude lower than its Ki-value for the inhibition of iso-glutaminyl cyclase (isoQC, QPCTL). Even more preferred are selective QC-inhibitors, wherein their Ki-value for the inhibition of glutaminyl cyclase (QC) is three orders of magnitude lower than their Ki-value for the inhibition of iso-glutaminyl cyclase (isoQC, QPCTL). Most preferred are selective QC-inhibitors, which do not inhibit iso-glutaminyl cyclase (isoQC, QPCTL).

The term "QPCTL-related disease" as used herein refers to all those diseases, disorders or conditions that are modulated by QPCTL.

Inhibitors of QC, which also could be useful as inhibitors of QC isoenzymes (e.g., QPCTL), are described in WO 2004/098625, WO 2004/098591, WO 2005/039548 and WO 2005/075436, which are incorporated herein in their entirety, especially with regard to the structure of the inhibitors, their use and their production. Potential QPCTL-inhibitors, which are suitable for uses and methods according to the present invention are disclosed in WO 2005/075436, which is incorporated herein in its entirety with regard to the structure, synthesis and methods of use of the QC-inhibitors.

Assays and Identification of Therapeutic Agents

The methods and compositions of the present invention are particularly useful in the evaluation of effectors of QPCTL, in particular inhibitors of QPCTL, and for the development of drugs and therapeutic agents for the treatment and/or prevention of amyloid-associated diseases such as Mild Cognitive Impairment, Alzheimer's disease, neurodegeneration in Down Syndrome, Familial Danish Dementia and Familial British Dementia.

Moreover, the methods and compositions of the present invention are also useful in the evaluation of effectors of QPCTL, in particular inhibitors of QPCTL, and for the development of drugs and therapeutic agents for the treatment and/or prevention of an inflammatory disease or condition, selected from the group of inflammatory diseases, in particular
 a. chronic and acute inflammations, e.g. rheumatoid arthritis, atherosclerosis, restenosis, pancreatitis,
 b. other inflammatory diseases, e.g. neuropathic pain, graft rejection/graft failure/graft vasculopathy, HIV infections/AIDS, gestosis, tuberous sclerosis, Guillain-Barré syndrome, chronic inflammatory demyelinising polyradiculoneuropathy and multiple sclerosis, and
 c. neuroinflammation.

In this regard, neurodegenerative diseases, e.g. mild cognitive impairment (MCI), Alzheimer's disease, neurodegeneration in Down Syndrome, Familial British Dementia and Familial Danish Dementia may also be the result of neuroinflammation.

The knock-out animal or the cells of the knock-out animal of the invention can be used in a variety of screening assays. For example, any of a variety of potential agents suspected of affecting QPCTL, as well as the appropriate antagonists and blocking therapeutic agents, can be screened by administration to the knock-out animal and assessing the effect of these agents upon the function and phenotype of the cells and on the phenotype, i.e. the neurological phenotype, of the knock-out animals.

Other assays to discover antagonists that will inhibit QPCTL are apparent from the disclosures of WO 2004/098625, WO 2004/098591 and WO 2005/075436, which describe inhibitors of QC and which are incorporated herein in their entirety.

Behavioral studies may also be used to test potential therapeutic agents, such as those studies designed to assess motor skills, learning and memory deficits. An example of such a test is the Morris Water maze (Morris (1981) Learn Motivat 12, 239-260). Additionally, behavioral studies may include evaluations of locomotor activity such as with the rotarod test (see for instance as described in Carter et al. (1999) J Neurosci. 19, 3248-57) and the open field (see for instance as described in von Hörsten et al. (1998) Pharmacology Biochemistry and Behavior 60, 71-76).

A preferred embodiment of the present invention is directed to an in vivo animal model for examining the phenotypic consequences resulting from heterozygous or homozygous deficiency of the QPCTL gene, wherein the animal model is a mammal, e.g. a mouse or rat, having a heterozygous or homozygous knock-out of the QPCTL gene. Since QPCTL is involved in a variety of biological, medical or physiological processes or phenomena, including, but not limited to neurodegenerative diseases, e.g. Mild Cognitive Impairment, Alzheimer's disease, neurodegeneration in Down Syndrome, Familial Danish Dementia and Familial British Dementia; and inflammatory diseases or conditions, selected from the group of inflammatory diseases, in particular
 a. chronic and acute inflammations, e.g. rheumatoid arthritis, atherosclerosis, restenosis, pancreatitis,
 b. other inflammatory diseases, e.g. neuropathic pain, graft rejection/graft failure/graft vasculopathy, HIV infections/AIDS, gestosis, tuberous sclerosis, Guillain-Barré syndrome, chronic inflammatory demyelinising polyradiculoneuropathy and multiple sclerosis, and
 c. neuroinflammation, the animal model having heterozygous or homozygous deficiency of the QPCTL gene is useful for studying mechanisms and/or etiology of the above-mentioned processes/phenomena. In a particular embodiment, the animal model of the present invention having heterozygous or homozygous deficiency of the QPCTL gene will be useful as a mammalian in vivo screening model for studying these and other processes/phenomena.

By "animal model" is meant that an animal that is sufficiently like humans in its anatomy, physiology, or response to a pathogen to be used in medical research, is used to investigate the physio- or pathological circumstances in question. According to the present invention, an animal model can be an exploratory model, aiming to understand a biological mechanism, e.g., amyloid beta peptide formation or maturation of chemokines and/or hormones, or an explanatory model, aiming to understand a more or less complex biological problem.

The analysis of the physiological function of QPCTL in vivo for the development of neurodegenerative diseases, e.g. Mild Cognitive Impairment, Alzheimer's disease, neurodegeneration in Down Syndrome, Familial Danish Dementia and Familial British Dementia; and inflammatory diseases or conditions, selected from the group of inflammatory diseases, in particular
 a. chronic and acute inflammations, e.g. rheumatoid arthritis, atherosclerosis, restenosis, pancreatitis,
 b. other inflammatory diseases, e.g. neuropathic pain, graft rejection/graft failure/graft vasculopathy, HIV infections/AIDS, gestosis, tuberous sclerosis, Guillain-Barré syndrome, chronic inflammatory demyelinising polyradiculoneuropathy and multiple sclerosis, and
 c. neuroinflammation, can be performed employing the heterozygous or homozygous QPCTL knock-out animals of the present invention. An effective screening for QPCTL inhibitors, which are useful in the treatment of the aforementioned diseases, could be performed by treating existing animal models for the specific diseases with test compounds and comparing the results of such treatment with the effects of the QPCTL gene knock-out in the QPCTL knock-out animals.

Preferred methods for screening for biologically active agents that inhibit or promote QPCTL activity in vivo thus comprise the following steps:

v) administering a test agent to a disease-specific non-human animal model, which is specific for the treatment of at least one disease selected from Mild Cognitive Impairment, Alzheimer's disease, neurodegeneration in Down Syndrome, Familial Danish Dementia, Familial British Dementia, or which is specific for an inflammatory disease, e.g. rheumatoid arthritis, atherosclerosis, restenosis, pancreatitis and neuroinflammation, vi) determining the effect of the test agent;

vii) comparing the effect of the test agent with the effect of the QPCTL gene knock-out in the QPCTL knock-out animal models, and viii) selecting test agents that have an efficacy similar to the effect of the QPCTL gene disruption on the specific disease.

A particular preferred embodiment is the use of this method for screening of QPCTL inhibitors.

In a further preferred embodiment, this method is used for the screening of QPCTL inhibitors for the treatment of Alzheimer's disease or neurodegeneration in Down syndrome.

In yet another preferred embodiment, this method is used for the screening of QPCTL inhibitors for the treatment of Familial British Dementia or Familial Danish Dementia.

Furthermore, this method is preferably used for the screening of QPCTL inhibitors for the treatment of a disease selected from rheumatoid arthritis, atherosclerosis, restenosis, and pancreatitis.

Moreover, this method is preferably used for the screening of QPCTL inhibitors for the treatment of other inflammatory diseases, e.g. neuropathic pain, graft rejection/graft failure/graft vasculopathy, HIV infections/AIDS, gestosis, tuberous sclerosis, Guillain-Barré syndrome, chronic inflammatory demyelinising polyradiculoneuropathy and multiple sclerosis.

In a most preferred embodiment, this method is used for the screening of QPCTL inhibitors for the treatment of neuroinflammation. As aforementioned, neurodegenerative diseases, e.g. mild cognitive impairment (MCI), Alzheimer's disease, neurodegeneration in Down Syndrome, Familial British Dementia and Familial Danish Dementia may also be a result of neuroinflammation.

Thus, this method is especially useful for the screening of QPCTL inhibitors for the treatment of both, neuroinflammation, and neurodegenerative diseases associated with neuroinflammation, e.g. mild cognitive impairment (MCI), Alzheimer's disease, neurodegeneration in Down Syndrome, Familial British Dementia and Familial Danish Dementia.

The efficacy of QPCTL-inhibitors for the treatment of Alzheimer's Disease, Familial British Dementia or Familial Danish Dementia and, e.g. neurodegeneration in Down Syndrome can be tested in existing animal models of Alzheimer's disease.

Suitable animal models of Alzheimer's Disease are reviewed in McGowan et al. TRENDS in Genetics, Vol. 22, No. May 2006, pp 281-289, and are selected from PDAPP, Tg2576, APP23, TgCRND8, $PSEN_{1M146V}$ or $PSEN_{1M146L}$, PSAPP, $APP_{Dutch}$, BRI-Aβ40 and BRI-Aβ42, JNPL3, $Tau_{P301S}$, $Tau_{V337M}$, $Tau_{R406W}$, rTg4510, $H_{tau}$, TAPP, 3×TgAD, as described below.

PDAPP: First mutant APP transgenic model with robust plaque pathology. Mice express a human APP cDNA with the Indiana mutation ($APP_{V717F}$). Plaque pathology begins between 6-9 months in hemizygous PDAPP mice. There is synapse loss but no overt cell loss and not NFT pathology is observed. This model has been used widely in vaccination therapy strategies.

Tg2576: Mice express mutant $APP_{SWE}$ under control of the hamster prion promoter. Plaque pathology is observed from 9 months of age. These mice have cognitive deficits but no cell loss or NFT pathology. This model is one of the most widely used transgenic models in the field of Alzheimer's disease.

APP23: Mice express mutant $APP_{SWE}$ under control of the Thy1 promoter. Prominent cerebrovascular amyloid, amyloid deposits are observed from 6 months of age and some hippocampal neuronal loss is associated with amyloid plaque formation.

TgCRND8: Mice express multiple APP mutations (Swedish plus Indiana). Cognitive deficits coincide with rapid extracellular plaque development at ~3 months of age. The cognitive deficits can be reversed by Aβ vaccination therapy.

$PSEN_{1M146V}$ or $PSEN_{1M146L}$ (lines 6.2 and 8.9, respectively): These models where the first demonstration in vivo that mutant PSEN1 selectively elevates Aβ42. No overt plaque pathology is observed.

PSAPP (Tg2576×$PSEN_{1M146L}$, PSEN1-A246E+$APP_{SWE}$): Bigenic transgenic mice, with the addition of the mutant PSEN1 transgene which markedly accelerated amyloid pathology compared with singly transgenic mutant APP mice, demonstrating that the PSEN1-driven elevation of Aβ42 enhances plaque pathology.

$APP_{Dutch}$: Mice express APP with the Dutch mutation that causes hereditary cerebral hemorrhage with amyloidosis-Dutch type in humans. $APP_{Dutch}$ mice develop severe congophilic amyloid angiopathy. The addition of a mutant PSEN1 transgene redistributes the amyloid pathology to the parenchyma indicating differing roles for Aβ40 and Aβ42 in vascular and parenchymal amyloid pathology.

BRI-Aβ40 and BRI-Aβ42: Mice express individual Aβ isoforms without APP over-expression. Only mice expressing Aβ42 develop senile plaques and CAA, whereas BRI-Aβ40 mice do not develop plaques, suggesting that Aβ42 is essential for plaque formation.

JNPL3: Mice express 4R0N MAPT with the P301L mutation. This is the first transgenic model, with marked tangle pathology and cell loss, demonstrating that MAPT alone can cause cellular damage and loss. JNPL3 mice develop motor impairments with age owing to servere pathology and motor neutron loss in the spinal cord.

$Tau_{P301S}$: Tansgenic mice expressing the shortest isoform of 4R MAPT with the P301S mutation. Homozygous mice develop severe paraparesis at 5-6 months of age with widespread neurofibrillary pathology in the brain and spinal cord and neuronal loss in the spinal cord.

$Tau_{V337M}$: Low level synthesis of 4R MAPT with the V337M mutation (1/10 endogenous MAPT) driven by the promoter of platelet-derived growth factor (PDGF). The development of neurofibrillary pathology in these mice suggests the nature of the MAPT rather than absolute MAPT intracellular concentration drives pathology.

$Tau_{R406W}$: Mice expressing 4R human MAPT with the R406W mutation under control of the CAMKII promoter. Mice develop MAPT inclusions in the forebrain from 18 months of age and have impaired associative memory.

rTg4510: Inducible MAPT transgenic mice using the TET-off system. Abnormal MAPT pathology occurs from one month of age. Mice have progressive NFT pathology and severe cell loss. Cognitive deficits are evident from 2.5 months of age. Turning off the transgene improves cognitive performance but NT pathology worsens.

H$_{tau}$: Transgenic mice expressing human genomic MAPT only (mouse MAPT knocked-out). Htau mice accumulate hyperphosphorylated MAPT from 6 months and develop Thio-S-positive NFT by the time they are 15 months old.

TAPP (Tg2576xJNPL3): Increased MAPT forebrain pathology in TAPP mice compared with JNPL3 suggesting mutant APP and/or Aβ can affect downstream MAPT pathology.

3xTgAD: Triple transgenic model expressing mutant APP$_{SWE}$, MAPT$_{P301L}$, on a PSEN1$_{M146V}$ 'knock-in' background (PSNE1-KI). Mice develop plaques from 6 months and MAPT pathology from the time they are 12 months old, strengthening the hypothesis that APP or Aβ can directly influence neurofibrillary pathology.

Moreover, WO 2009/034158 discloses non-human transgenic animal models, wherein the transgene encodes at least one amyloid beta (Aβ) peptide selected from the group consisting of AβN3E-42, AβN3Q-42, AβN3E-40 and AβN3Q-40. These Aβ peptides are substrates of QC and QPCTL, resulting in the cyclization of the N-terminal glutamine (Q) or glutamate (N) to pyroglutamate (pGlu). Thus, these transgenic animal models provide a model system for the investigation of the effect of pGlu-Aβ peptides on the course of the development of neurodegenration.

Cross-breeding of the above-mentioned animal models as with the inventive model is a useful strategy to characterize and isolate new target enzymes for a treatment of Alzheimer's disease. Non-human transgenic animals that overexpress glutaminyl cyclase (QC, QPCT), and which are useful in the screening method described above, are disclosed in WO 2008/087197.

The non-human animal models of the present invention are characterized in that they bear a QPCTL gene disruption and thus do not produce the QPCTL protein. However, these animal models still bear the intact glutaminyl cyclase (QC, QPCT) gene and produce the enzymatically active QC protein. Thus, the present QPCTL knock-out animals are especially useful for screening of effectors, in particular inhibitors, which are selective for QC.

Preferred methods for screening for biologically active agents that selectively inhibit or promote QC activity in vivo thus comprise the following steps:
  i. administering a test agent to the non-human animal model bearing a QPCTL gene disruption,
  ii. determining the effect of the test agent on the QC activity in vivo;
  iii. comparing the effect of the test agent on the in vivo QC activity with the in vivo QC activity in non-human QPCTL knock-out animals, which have received placebo, and
  iv. selecting test agents that have an inhibitory or promoting effect on QC activity in vivo.

A particular preferred embodiment is the use of this method for screening of selective QC inhibitors.

In a further preferred embodiment, this method is used for the screening of selective QC inhibitors for the treatment of Alzheimer's disease or neurodegeneration in Down syndrome.

In yet another preferred embodiment, this method is used for the screening of selective QC inhibitors for the treatment of Familial British Dementia or Familial Danish Dementia.

Furthermore, this method is preferably used for the screening of selective QC inhibitors for the treatment of a chronic or acute inflammatory disease selected from rheumatoid arthritis, atherosclerosis, restenosis, and pancreatitis.

Moreover, this method is preferably used for the screening of selective QC inhibitors for the treatment of other inflammatory diseases, e.g. neuropathic pain, graft rejection/graft failure/graft vasculopathy, HIV infections/AIDS, gestosis, tuberous sclerosis, Guillain-Barré syndrome, chronic inflammatory demyelinising polyradiculoneuropathy and multiple sclerosis.

In a most preferred embodiment, this method is used for the screening of QC inhibitors for the treatment of neuroinflammation. As aforementioned, neurodegenerative diseases, e.g. mild cognitive impairment (MCI), Alzheimer's disease, neurodegeneration in Down Syndrome, Familial British Dementia and Familial Danish Dementia may also be a result of neuroinflammation.

Thus, this method is especially useful for the screening of QC inhibitors for the treatment of both, neuroinflammation, and neurodegenerative diseases associated with neuroinflammation, e.g. mild cognitive impairment (MCI), Alzheimer's disease, neurodegeneration in Down Syndrome, Familial British Dementia and Familial Danish Dementia.

Suitable study designs could be as outlined in Table 1 below. isoQC or QC inhibitors inhibitors could be applied via the drinking solution or chow, or any other conventional route of administration, e.g. orally, intravenously or subcutaneously.

TABLE 1

Animal groups for the treatment of animal models of Alzheimer's disease with QPCTL-inhibitors

| Group | Treatment | Mode |
|---|---|---|
| 1.) negative control | vehicle | 10 months old (41-45 weeks) |
| 2.) positive control | Ibuprofen | treatment for 6 months (25-26 weeks) starting at the age of 4 months (15-20 weeks) |
| 3.) Qpct-inhibitor | low dose | treatment for 6 months (25-26 weeks) starting at the age of 4 months (15-20 weeks) |
| 4.) Qpct-inhibitor | high dose | treatment for 6 months (25-26 weeks) starting at the age of 4 months (15-20 weeks) |

With regard to Alzheimer's disease, the efficacy of the QPCTL inhibitors can be assayed by sequential extraction of Aβ using SDS and formic acid. Initially, the SDS and formic acid fractions containing the highest Aβ concentrations can be analyzed using an ELISA quantifying total Aβ(x-42) or Aβ(x-40) as well as [pGlu$^3$]Aβ3-40/42/43 or [pGlu$^{11}$]Aβ11-40/42/43. Test compounds that are identified employing the screening method above and which are suitable for further pharmaceutical development should reduce the formation of [pGlu$^3$]Aβ3-40/42/43 or [pGlu$^{11}$]Aβ11-40/42/43. In particular, suitable test compounds are capable to reduce the formation of [pGlu$^3$]Aβ3-40 and/or [pGlu$^3$]Aβ3-42.

An ELISA kit for the quantification of [pGlu$^3$]Aβ3-42 is commercially available from IBL, Cat-no. JP27716.

An ELISA for the quantification of [pGlu3]Aβ3-40 is described by Schilling et al. 2008 (Schilling S, Appl T, Hoffmann T, Cynis H, Schulz K, Jagla W, Friedrich D, Wermann M, Buchholz M, Heiser U, von Hörsten S, Demuth H U. Inhibition of glutaminyl cyclase prevents pGlu-Abeta formation after intracortical/hippocampal microinjection in vivo/in situ. J Neurochem. 2008 August; 106(3):1225-36.)

An alternative treatment regime is shown in Table 2 below.

TABLE 2

Animal groups involved, examination of the effect of inhibitors of QPCTL on the progression of plaque formation in animal models of AD

| Group | Treatment | Mode |
|---|---|---|
| 1) negative control | Vehicle | 16 months old (67-70 weeks) |
| 2) positive control | Ibuprofen (0.2 mg/ml) | treatment for 5 months (21-22 weeks) starting at the age 11 months (46-49 weeks) |
| 3) QPCTL-inhibitor | low dose | treatment for 5 months (21-22 weeks) starting at the age of 11 months (46-49 weeks) |
| 4) QPCTL-inhibitor | high dose | treatment for 5 months (21-22 weeks) starting at the age of 11 months (46-49 weeks) |

Following QPCTL-inhibitor treatment, the AD animal can be tested regarding behavioral changes. Suitable behavioral test paradigms are, e.g. those, which address different aspects of hippocampus-dependent learning. Examples for such neurological tests are the "Morris Water Maze Test" and the "Fear Conditioning Test" looking at contextual memory changes (Comery, T A et al, (2005), J Neurosci 25:8898-8902; Jacobsen J S et al, (2006), Proc Natl. Acad. Sci. USA 103:5161-5166).

The animal model of inflammatory diseases, e.g. atherosclerosis contemplated by the present invention can be an existing atherosclerosis animal model, e.g., apoE deficient mouse, or can be prepared, for example, by preparing a transgenic mouse having QPCTL gene overexpression or gene deficiency with apoE deficient background. The apolipoprotein E knock-out mouse model has become one of the primary models for atherosclerosis (Arterioscler Thromb Vase Biol., 24: 1006-1014, 2004; Trends Cardiovasc Med, 14: 187-190, 2004). The studies may be performed as described by Johnson et al. in Circulation, 111: 1422-1430, 2005, or using modifications thereof. Apolipoprotein E (apoE) is a component of several plasma lipoproteins, including chylomicrons, VLDL, and HDL. Receptor-mediated catabolism of these lipoprotein particles is mediated through the interaction of apoE with the LDL receptor (LDLR) or with LDLR-related protein (LRP). ApoE-deficient mice exhibit hypercholesterolemia and develop complex atheromatous lesions similar to those seen in humans. The efficacy of the compounds of the present invention was also evaluated using this animal model. The aforementioned method is further suitable for transgenic mice overexpressing a mutant form of ApoE, e.g. ApoE*3 Leiden mice (J. Biol. Chem. 268, 14: 10540-10545).

Other animal models for inflammatory diseases, which are suitable for use in the aforementioned screening method, are the thioglycollate-induced inflammation model in mice as described by Melnicoff et al. (1989) Cell. Immunol. 18, 178-191, the collagen-induced arthritis model in rat as described in Ogata et al. (1997) J. Pathol. 182, 106-114, the antibody induced arthritis model in rat and rat models of restenosis (e.g. the effects of the test compounds on rat carotid artery responses to the balloon catheter injury) as described for instance in Langeveld et al. (2004) J Vasc. Res. 41, 377-86.

A particular preferred embodiment of the present invention is the use of the animal model for screening and characterization of new medical targets.

The presented inventive animal model is suitable to be crossbred with one of the following models of restenosis or atherosclerosis for the purpose of identification of novel targets for treatment of the mentioned disorders.

Such animal models are:
  ApoE knock out mice
  ApoB overexpressing mice
  ApoE2 expressing mice
  ApoE2 expressing knock-in mice
  ApoE3*Leiden expressing mice
  LDL receptor knock out mice ApoE knock out mice were generated by gene targeting and develop spontaneous hypercholesterolemia and arterial lesions (Zhang et al. Science 1992 Oct. 16;258(5081):468-71).

ApoB overexpressing mice were generated by microinjecting a 79.5 kb genomic DNA fragment containing the ApoB gene into fertilized mouse eggs and represent a model for studying ApoB metabolism and the role of ApoB in atherosclerosis (Linton et al. J. Clin. Invest. 1993 December;92(6):3029-37).

ApoE*2 expressing mice were generated by microinjection of the complete ApoE*2 gene including 5 kb of its 5' flanking sequences and 1.7 kb of its 3' sequences. The expression of the transgene is mainly found in the liver. Plasma levels of lipids depend on the expression of the transgene (Huang et al. J. Biol. Chem. 1996 Nov. 15;271(46):29146-51)

ApoE*2 expressing knock-in mice are generated by replacing mouse ApoE*2 gene by the human ApoE*2 gene in mouse embryonic stem cells. These mice develop type III hyperlipoproteinemia with plasma cholesterol and trigylceride levels twice to three times higher than in wt mice. ApoE*2 knock in mice are defective in clearing VLDL particles and develop atherosclerosis spontaneously or upon high fat diet (Sullivan et al. J. Clin. Invest. 1998 Jul. 1;102(1):130-5).

ApoE3*Leiden expressing mice were generated by microinjection of 27 kb of a human DNA fragment containing the mutated ApoE3*Leiden gene, the gene for ApoC1 and the ApoC1 pseudogene. The mice develop hyperlipoproteinemia with significantly elevated levels of total plasma cholesterol and triglycerides. Upon high fat chow, these levels are even higher (van den Maagdenberg et al. J Biol. Chem. 1993 May 15;268(14):10540-5).

LDL receptor knock out mice are generated by homologous recombination using mouse embryonic stem cells. $LDLR^{-/-}$ mice exhibit twofold higher levels of plasma cholesterol and a seven-to ninefold increase in intermediate density lipoproteins (IDL) and LDL. Plasma triglycerides and HDL are normal. Application of high fat diet increases the cholesterol content of IDL and LDL. (Ishibashi et al. J. Clin. Invest. 1993 August;92(2):883-93).

Cross-breeding of the above-mentioned animal models as with the inventive model is a useful strategy to characterize the role of QPCT inhibitors to treat atherosclerosis or restenosis.

With regard to inflammatory diseases, the efficacy of the QPCTL inhibitors can be assayed by measuring the inhibition of the chemotaxis of monocytic cell lines (e.g. THP-1) or peripheral mononuclear cells derived from transgenic or non-transgenic animals induced by MCP-1 or lavage fluids from transgenic mice in vitro. The assay is described in example 11 (no such example present) in the Example section hereinafter. An inhibitory effect has also been observed in vivo. Effective test compounds should show a reduced monocyte infiltration in a thioglycollate-induced inflammation model in mice.

Furthermore, the inhibition of the formation of pGlu-MCP-1 can be tested in vitro and in vivo. Such assays are described in examples 5, 7, 8 and 9. The methods of the invention can advantageously use cells isolated from a homozygous or heterozygous QPCTL mutant non-human mammal, to study amyloid accumulation as well as to test potential therapeutic compounds. The methods of the invention can also be used with cells expressing QPCTL such as a transfected cell line.

A QPCTL knock-out cell can be used in an in vitro method to identify potential new treatment strategies for diseases, which are associated or caused by with pGlu-peptide formation, like for instance, but not limited to, Alzheimers disease, familial British Dementia or atherosclerosis.

A QPCTL knock-out cell can be used in an in vitro method to screen compounds as potential therapeutic agents for treating Aβ associated diseases. In such a method, a compound is contacted with a QPCTL knock-out cell, a transfected cell or a cell derived from a QPCTL mutant non-human animal, and screened for alterations in a phenotype associated with expression of QPCTL. The changes in Aβ production in the cellular assay and the knock-out animal can be assessed by methods well known to those skilled in the art.

A QPCTL fusion polypeptide such as QPCTL-EGFP can be particularly useful for such screening methods since the expression of QPCTL can be monitored by fluorescence intensity. Other exemplary fusion polypeptides include other fluorescent proteins, or modifications thereof, glutathione-S-transferase (GST), maltose binding protein, poly His, and the like, or any type of epitope tag. Such fusion polypeptides can be detected, for example, using antibodies specific to the fusion polypeptides. The fusion polypeptides can be an entire polypeptide or a functional portion thereof so long as the functional portion retains desired properties, for example, antibody binding activity or fluorescence activity.

The invention further provides a method of identifying a potential therapeutic agent for use in treating the diseases as mentioned above. The method includes the steps of contacting a cell containing the above DNA construct with a compound and screening the cell for the results to be observed, thereby identifying a potential therapeutic agent for use in treating QPCTL-related diseases. The cell can be isolated from a knock-out non-human mammal having nucleated cells containing the QPCTL DNA construct. Alternatively, the cell can contain a DNA construct comprising a nucleic acid encoding a green fluorescent protein fusion, or other fusion polypeptide, with a QPCTL polypeptide.

Additionally, QPCTL knock-out cells expressing a QPCTL polypeptide can be used in a preliminary screen to identify compounds as potential therapeutic agents having an activity that alters a phenotype associated with QPCTL expression. As with in vivo screens using QPCTL knock-out non-human mammals, an appropriate control cell can be used to compare the results of the screen. The effectiveness of compounds identified by an initial in vitro screen using QPCTL knock-out cells can be further tested in vivo using the inventive QPCTL knock-out non-human mammals, if desired. Thus, the invention provides methods of screening a large number of compounds using a cell-based assay, for example, using high throughput screening, as well as methods of further testing compounds as therapeutic agents in an animal model of Aβ-related disorders.

In a further embodiment, the present invention provides a method of preventing or treating a condition mediated by modulation of the QPCTL enzyme activity in a subject in need thereof which comprises administering any of the compounds of the present invention or pharmaceutical compositions thereof in a quantity and dosing regimen therapeutically effective to treat the condition. Additionally, the present invention includes the use of the compounds of this invention, and their corresponding pharmaceutically acceptable acid addition salt forms, for the preparation of a medicament for the prevention or treatment of a condition mediated by modulation of the QPCTL activity in a subject. The compound may be administered to a patient by any conventional route of administration, including, but not limited to, intravenous, oral, subcutaneous, intramuscular, intradermal, parenteral and combinations thereof.

For instance, the present invention provides a new method for the treatment of Mild Cognitive Impairment (MCI), Alzheimer's disease, Familial Danish Dementia, Familial British Dementia and neurodegeneration in Down syndrome. The N-termini of the amyloid β-peptides deposited in the Alzheimer's disease and Down syndrome brain, in particular Aβ(3-40), Aβ(3-42), Aβ(11-40) and Aβ(11-42), and the amyloid peptides ADan and ABri deposited in Familial Danish Dementia and Familial British Dementia as well, bear pyroglutamic acid. The pGlu formation is an important event in the development and progression of the disease, since the modified amyloid β-peptides, ADan and ABri show an enhanced tendency to amyloid aggregation and toxicity, likely worsening the onset and progression of the disease. (Russo, C. et al. (2002) J Neurochem. 82, 1480-1489; Ghiso, J. et al. (2001) Amyloid 8, 277-284).

In contrast, in the natural Aβ-peptides (3-40/42), glutamic acid is present as an N-terminal amino acid.

QPCTL is involved in the formation of pyroglutamic acid that favors the aggregation of amyloid β-peptides. Thus, an inhibition of QPCTL leads to a prevention of the precipitation of the plaque-forming [pGlu$^3$]Aβ3-40/42/or [pGlu$^{11}$]Aβ11-40/42/, causing the onset and progression of Alzheimer's disease and Down Syndrome.

Glutamate is found in positions 3, 11 and 22 of the amyloid β-peptide. Among them the mutation from glutamic acid (E) to glutamine (Q) in position 22 (corresponds to amino acid 693 of the amyloid precursor protein APP770, Swissprot entry: P05067) has been described as the so-called Dutch type cerebroarterial amyloidosis mutation.

The β-amyloid peptides with a pyroglutamic acid residue in position 3, 11 and/or 22 have been described to be more cytotoxic and more hydrophobic than Aβ1-40/4243 (Saido, T. C. (2000) Medical Hypotheses 54, 427-429).

There had been no experimental evidence supporting the enzymatic conversion of Glu$^1$-peptides into pGlu-peptides by an unknown glutamyl cyclase (EC) (Garden, R. W., Moroz, T. P., Gleeson, J. M., Floyd, P. D., Li, L. J., Rubakhin, S. S., and Sweedler, J. V. (1999) J Neurochem. 72, 676-681; Hosoda R. et al. (1998) J Neuropathol. Exp. Neurol. 57, 1089-1095). No such enzyme activity had been identified, capable of cyclizing Glu$^1$-peptides, which are protonated N-terminally and possess a negatively charged Glu$^1$ γ-carboxylate moiety under mildly alkaline or neutral pH-conditions.

QC-activity against Gln$^1$-substrates is dramatically reduced below pH 7.0. In contrast, it appears that Glu$^1$-conversion can occur at acidic reaction conditions (e.g. Iwatsubo, T., Saido, T. C., Mann, D. M., Lee, V. M., and Trojanowski, J. Q. (1996) Am. J. Pathol. 149, 1823-1830).

Earlier, it was investigated whether QC (QPCT) is able to recognize and to turnover amyloid-β derived peptides under mildly acidic conditions (WO 2004/098625). Therefore, the peptides [Gln$^3$]Aβ1-11a, Aβ3-11a, [Gln$^3$]Aβ3-11a, Aβ3-21a, [Gln$^3$]Aβ3-21a and [Gln$^3$]Aβ3-40 as potential substrates of the enzyme were synthesized and investigated. These sequences were chosen for mimicking natural N-terminally and C-terminally truncated [Glu$^3$]Aβ peptides and [Gln$^3$]Aβ peptides which could occur due to post-translational Glu-amidation.

It was shown that papaya and human Qpct catalyze both glutaminyl and glutamyl cyclization. Apparently, the primary physiological function of Qpct is to finish hormone maturation in endocrine cells by glutamine cyclization prior to or during the hormone secretion process. Such secretory vesicles are known to be acidic in pH. Thus, a side activity of the enzyme in the narrow pH-range from 5.0 to 7.0 could be its newly discovered glutamyl cyclase activity cyclizing also Glu-Aβ peptides. However, due to the much slower occurring Glu-cyclization compared to Gln-conversion, it is questionable whether the glutamyl cyclization plays a significant physiological role. In the pathology of neurodegenerative disorders, however, the glutamyl cyclization is of relevance.

In summary, it was shown that human QC (QPCT), which is highly abundant in the brain, is likely a catalyst of the formation of the amyloidogenic pGlu-Aβ peptides from Glu-Aβ and Gln-Aβ precursors, which make up more than 50% of the plaque deposits found in Alzheimer's disease. These findings identify QC as a player in senile plaque formation and thus as a novel drug target in the treatment of Alzheimer's disease, neurodegeneration in Down Syndrome, Familial Danish Dementia and Familial British Dementia. See, e.g. WO 2004/098625 and WO 2005/039548.

It has been shown that QPCTL and QPCT are partially co-localized in the cells and that QPCTL catalyzes the formation of pGlu-Aβ related peptides (WO2008/034891; US2008-0249083). Therefore, QPCTL is a target for diminishing the pGlu-Aβ formation.

In a preferred embodiment, the present invention provides the use of activity-decreasing effectors of QPCTL, as selected with use of the present inventive animal model and the screening methods described herein, for the suppression of pGlu-Amyloid peptide formation in Mild Cognitive Impairment, Alzheimer's disease, Down Syndrome, Familial Danish Dementia and Familial British Dementia.

In a further preferred embodiment, the present invention provides the use of inhibitors of QPCTL, as selected with use of the present inventive animal model and the screening methods described herein, for the suppression of the pGlu formation at the N-terminus of cytokines and thereby suppressing chemokine function and leading to diminished inflammatory responses.

Chemotactic cytokines (chemokines) are proteins that attract and activate leukocytes and are thought to play a fundamental role in inflammation. Chemokines are divided into four groups categorized by the appearance of N-terminal cysteine residues ("C"-; "CC"-; "CXC"- and "CX3C"-chemokines). "CXC"-chemokines preferentially act on neutrophils. In contrast, "CC"-chemokines attract preferentially monocytes to sites of inflammation. Monocyte infiltration is considered to be a key event in a number of disease conditions (Gerard, C. and Rollins, B. J. (2001) *Nat. Immunol.* 2, 108-115; Bhatia, M., et al. (2005) *Pancreatology.* 5, 132-144; Kitamoto, S., Egashira, K., and Takeshita, A. (2003) *J Pharmacol. Sci.* 91, 192-196). The MCP family, as one family of chemokines, consists of four members (MCP-1 to 4), displaying a preference for attracting monocytes but showing differences in their potential (Luini, W., et al. (1994) *Cytokine* 6, 28-31; Uguccioni, M., et al. (1995) *Eur. J Immunol.* 25, 64-68).

A number of studies have underlined in particular the crucial role of MCP-1 for the development of atherosclerosis (Gu, L., et al. (1998) *Mol. Cell.* 2, 275-281; Gosling, J., et al. (1999) *J Clin. Invest.* 103, 773-778); rheumatoid arthritis (Gong, J. H., et al. (1997) *J Exp. Med.* 186, 131-137; Ogata, H., et al. (1997) *J Pathol.* 182, 106-114); pancreatitis (Bhatia, M., et al. (2005) *Am. J Physiol. Gastrointest. Liver Physiol.* 288, G1259-G1265); Alzheimer's disease (Yamamoto, M., et al. (2005) *Am. J Pathol.* 166, 1475-1485); lung fibrosis (Inoshima, I., et al. (2004) *Am. J Physiol. Lung Cell. Mol. Physiol.* 286, L1038-L1044); renal fibrosis (Wada, T., et al. (2004) *J Am. Soc. Nephrol.* 15, 940-948), and graft rejection (Saiura, A., et al. (2004) *Arterioscler. Thromb. Vasc. Biol.* 24, 1886-1890). Furthermore, MCP-1 might also play a role in gestosis (Katabuchi, H., et al. (2003) *Med Electron Microsc.* 36, 253-262), as a paracrine factor in tumor development (Ohta, M., et al. (2003) *Int. J Oncol.* 22, 773-778; Li, S., et al. (2005) *J Exp. Med.* 202, 617-624), neuropathic pain (White, F. A., et al. (2005) *Proc. Natl. Acad. Sci. U.S.A*) and AIDS (Park, I. W., Wang, J. F., and Groopman, J. E. (2001) *Blood* 97, 352-358; Coll, B., et al. (2006) *Cytokine* 34, 51-55).

The mature form of human and rodent MCP-1 is post-translationally modified by Glutaminyl Cyclase (QPCTL) and/or QPCTL to possess an N-terminal pyroglutamyl (pGlu) residue. The N-terminal pGlu modification makes the protein resistant against N-terminal degradation by aminopeptidases, which is of importance, since chemotactic potency of MCP-1 is mediated by its N-terminus (Van Damme, J., et al. (1999) *Chem Immunol* 72, 42-56). Artificial elongation or degradation leads to a loss of function although MCP-1 still binds to its receptor (CCR2) (Proost, P., et al. (1998) *J Immunol.* 160, 4034-4041; Zhang, Y. J., et al. (1994) *J Biol. Chem.* 269, 15918-15924; Masure, S., et al. (1995) *J Interferon Cytokine Res.* 15, 955-963; Hemmerich, S., et al. (1999) *Biochemistry* 38, 13013-13025).

Due to the major role of MCP-1 in a number of disease conditions, an anti-MCP-1 strategy is required. Therefore, small orally available compounds inhibiting the action of MCP-1 are promising candidates for a drug development. Inhibitors of Iso Glutaminyl Cyclase are small orally available compounds, which target the important step of pGlu-formation at the N-terminus of MCP-1 (Cynis, H., et al. (2006) *Biochim. Biophys. Acta* 1764, 1618-1625; Buchholz, M., et al. (2006) *J Med. Chem.* 49, 664-677). As a consequence, caused by QPCTL-inhibition, the N-terminus of MCP-1 is not protected by a pGlu-residue. Instead, the N-terminus possesses a glutamine-proline motif, which is prone to cleavage by dipeptidylpeptidases, e.g. dipeptidylpeptidase 4 and fibroblast activating protein (FAP, Seprase), which are abundant on the endothelium and within the blood circulation. This cleavage results in the formation of N-terminal truncated MCP-1. These molecules unfold, in turn, an antagonistic action at the CCR2 and therefore, monocyte-related disease conditions are inhibited efficiently. A proof for the involvement of QPCTL in the maturation of MCP-1—generated with the inventive animal model or cells isolated from the inventive model—is provided in examples 7, 8 and 9.

Accordingly, the present invention provides the use of inhibitors of QPCTL, as selected with use of the present inventive animal model and the screening methods described herein, for the treatment of a disease selected from rheumatoid arthritis, atherosclerosis, restenosis, and pancreatitis.

In a further preferred embodiment, the present invention provides the use of inhibitors of QPCTL, as selected with use of the present inventive animal model and the screening methods described herein, for the treatment of other inflammatory diseases, e.g. neuropathic pain, graft rejection/graft failure/graft vasculopathy, HIV infections/AIDS, gestosis, tuberous sclerosis, Guillain-Barré syndrome, chronic inflammatory demyelinising polyradiculoneuropathy and multiple sclerosis.

In a most preferred embodiment, the present invention provides the use of inhibitors of QPCTL, as selected with use of the present inventive animal model and the screening methods described herein, for the treatment of neuroinflammation. As aforementioned, neurodegenerative diseases, e.g. mild cognitive impairment (MCI), Alzheimer's disease, neurodegeneration in Down Syndrome, Familial British Dementia and Familial Danish Dementia may also be a result of neuroinflammation.

Thus, the QPCTL inhibitors selected with use of the present inventive animal model and the screening methods described herein are in particular useful for the treatment of both, neuroinflammation, and neurodegenerative diseases associated with neuroinflammation, e.g. mild cognitive impairment (MCI), Alzheimer's disease, neurodegeneration in Down Syndrome, Familial British Dementia and Familial Danish Dementia.

Polyglutamine expansions in several proteins lead to neurodegenerative disorders, such as Chorea Huntington, Parkinson disease and Kennedy's disease. The mechanism therefore remains largely unknown. The biochemical properties of polyglutamine repeats suggest one possible explanation: endolytic cleavage at a glutaminyl-glutaminyl bond followed by pyroglutamate formation may contribute to the pathogenesis through augmenting the catabolic stability, hydrophobicity, amyloidogenicity, and neurotoxicity of the polyglutaminyl proteins (Saido, T. C.; Med Hypotheses (2000) March; 54(3):427-9).

In a further embodiment, the present invention therefore provides the use of inhibitors of QPCTL, as selected with the present inventive animal model and the screening methods described herein, for the preparation of a medicament for the treatment of Parkinson disease and Huntington's disease.

As aforementioned, the non-human animal model of the present invention is particularly useful for the screening for and identification of selective inhibitors of glutaminyl cyclase (QC, QPCT).

Accordingly, the present invention in a further embodiment provides the use of selective inhibitors of QC, as selected with the present inventive animal model and the screening methods described herein, for the treatment of a disease or disorder selected from the group consisting of
  a. chronic and acute inflammations, e.g. rheumatoid arthritis, atherosclerosis, restenosis, pancreatitis,
  b. other inflammatory diseases, e.g. neuropathic pain, graft rejection/graft failure/graft vasculopathy, HIV infections/AIDS, gestosis, tuberous sclerosis, Guillain-Barré syndrome, chronic inflammatory demyelinising polyradiculoneuropathy and multiple sclerosis,
  c. neuroinflammation,
  d. neurodegenerative diseases, e.g. mild cognitive impairment (MCI), Alzheimer's disease, neurodegeneration in Down Syndrome, Familial British Dementia, Familial Danish Dementia, multiple sclerosis, which may result from neuroinflammation, and
  e. Parkinson disease and Huntington's disease.

In an especially preferred embodiment, the present invention provides the use of selective inhibitors of QC, as selected with the present inventive animal model and the screening methods described herein, for the treatment of both, neuroinflammation, and neurodegenerative diseases associated with neuroinflammation, e.g. mild cognitive impairment (MCI), Alzheimer's disease, neurodegeneration in Down Syndrome, Familial British Dementia and Familial Danish Dementia.

In another embodiment, the present invention provides a general way to reduce or inhibit the enzymatic activity of QPCTL by using a QPCTL inhibitor selected above.

Inhibition of a mammalian QC (QPCT) was only detected initially for 1,10-phenanthroline and reduced 6-methylpterin (Busby, W. H. J. et al. (1987) J Biol. Chem. 262, 8532-8536). EDTA did not inhibit QC, thus it was concluded that QC is not a metal-dependent enzyme (Busby, W. H. J. et al. (1987) J Biol. Chem. 262, 8532-8536, Bateman, R. C. J. et al. (2001) Biochemistry 40, 11246-11250, Booth, R. E. et al. (2004) BMC Biology February 10;2:2). However, it was shown, that human QC and other animal QC's are metal-dependent enzymes, as revealed by the inhibition characteristics of QC by 1,10-phenanthroline, dipicolinic acid, 8-hydroxy-quinoline and other chelators and by the reactivation of QC by transition metal ions. Finally, the metal dependence is outlined by a sequence comparison to other metal-dependent enzymes, showing a conservation of the chelating amino acid residues also in human QPCTL. The interaction of compounds with the active-site bound metal ion represents a general way to reduce or inhibit QPCTL activity. The metal dependency of QPCTL is further characterized in the present invention by TXRF spectroscopy, isolation of the QPCTL apoenzyme and reactivation by transition metal ions (example 10).

The effectors identified with the use of the non-human animal model of the present invention and the screening methods described herein can be converted into acid addition salts, especially pharmaceutically acceptable acid addition salts.

The salts of the compounds of the invention may be in the form of inorganic or organic salts.

The compounds of the present invention can be converted into and used as acid addition salts, especially pharmaceutically acceptable acid addition salts. The pharmaceutically acceptable salt generally takes a form in which a basic side chain is protonated with an inorganic or organic acid. Representative organic or inorganic acids include hydrochloric, hydrobromic, perchloric, sulfuric, nitric, phosphoric, acetic, propionic, glycolic, lactic, succinic, maleic, fumaric, malic, tartaric, citric, benzoic, mandelic, methanesulfonic, hydroxyethanesulfonic, benzenesulfonic, oxalic, pamoic, 2-naphthalenesulfonic, p-toluenesulfonic, cyclohexanesulfamic, salicylic, saccharinic or triflu-oroacetic acid. All pharmaceutically acceptable acid addition salt forms of the compounds of the present invention are intended to be embraced by the scope of this invention.

In view of the close relationship between the free compounds and the compounds in the form of their salts, whenever a compound is referred to in this context, a corresponding salt is also intended, provided such is possible or appropriate under the circumstances.

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Furthermore, some of the crystalline forms of the compounds may exist as polymorphs and as such are intended to be included in the present invention. In addition, some of the compounds may form solvates with water (i.e. hydrates) or common organic solvents, and such solvates are also intended to be encompassed within the scope of this invention.

The compounds, including their salts, can also be obtained in the form of their hydrates, or include other solvents used for their crystallization.

In a further preferred form of implementation, the invention relates to pharmaceutical compositions, that is to say, medicaments, that contain at least one compound of the invention or salts thereof, optionally in combination with one or more pharmaceutically acceptable carriers and/or solvents.

The pharmaceutical compositions may, for example, be in the form of parenteral or enteral formulations and contain appropriate carriers, or they may be in the form of oral formulations that may contain appropriate carriers suitable for oral administration. Preferably, they are in the form of oral formulations.

The effectors of QPCTL activity administered according to the invention may be employed in pharmaceutically administrable formulations or formulation complexes as inhibitors or in combination with inhibitors, substrates, pseudosubstrates, inhibitors of QPCTL expression, binding proteins or antibodies of those enzyme proteins that reduce the QPCTL protein concentration in mammals. The compounds of the invention make it possible to adjust treatment individually to patients and diseases, it being possible, in particular, to avoid individual intolerances, allergies and side-effects.

The compounds also exhibit differing degrees of activity as a function of time. The physician providing treatment is thereby given the opportunity to respond differently to the individual situation of patients: he is able to adjust precisely, on the one hand, the speed of the onset of action and, on the other hand, the duration of action and especially the intensity of action.

A preferred treatment method according to the invention represents a new approach for the prevention or treatment of a condition mediated by modulation of the QPCTL enzyme activity in mammals. It is advantageously simple, susceptible of commercial application and suitable for use, especially in the treatment of diseases that are based on unbalanced concentration of physiological active QPCTL substrates in mammals and especially in human medicine.

The compounds may be advantageously administered, for example, in the form of pharmaceutical preparations that contain the active ingredient in combination with customary additives like diluents, excipients and/or carriers known from the prior art. For example, they can be administered parenterally (for example i.v. in physiological saline solution) or enterally (for example orally, formulated with customary carriers).

Depending on their endogenous stability and their bioavailability, one or more doses of the compounds can be given per day in order to achieve the desired normalisation of the blood glucose values. For example, such a dosage range in humans may be in the range of from about 0.01 mg to 250.0 mg per day, preferably in the range of about 0.01 to 100 mg of compound per kilogram of body weight.

The compounds used according to the invention can accordingly be incorporated in a manner known per se into conventional formulations, such as, for example, tablets, capsules, dragées, pills, suppositories, granules, aerosols, syrups, liquid, solid and cream-like emulsions and suspensions and solutions, using inert, non-toxic, pharmaceutically suitable carriers and additives or solvents. In each of those formulations, the therapeutically effective compounds are preferably present in a concentration of approximately from 0.1 to 80% by weight, more preferably from 1 to 50% by weight, of the total mixture, that is to say, in amounts sufficient for the mentioned dosage latitude to be obtained.

The formulations may be advantageously prepared, for example, by extending the active ingredient with solvents and/or carriers, optionally with the use of emulsifiers and/or dispersants, it being possible, for example, in the case where water is used as diluent, for organic solvents to be optionally used as auxiliary solvents.

Examples of excipients useful in connection with the present invention include: water, non-toxic organic solvents, such as paraffins (for example natural oil fractions), vegetable oils (for example rapeseed oil, groundnut oil, sesame oil), alcohols (for example ethyl alcohol, glycerol), glycols (for example propylene glycol, polyethylene glycol); solid carriers, such as, for example, natural powdered minerals (for example highly dispersed silica, silicates), sugars (for example raw sugar, lactose and dextrose); emulsifiers, such as non-ionic and anionic emulsifiers (for example polyoxyethylene fatty acid esters, polyoxyethylene fatty alcohol ethers, alkylsulphonates and arylsulphonates), dispersants (for example lignin, sulphite liquors, methylcellulose, starch and polyvinylpyrrolidone) and lubricants (for example magnesium stearate, talcum, stearic acid and sodium lauryl sulphate) and optionally flavourings.

Administration may be carried out in the usual manner, preferably enterally or parenterally, especially orally. In the case of enteral administration, tablets may contain in addition to the above-mentioned carriers further additives such as sodium citrate, calcium carbonate and calcium phosphate, together with various additives, such as starch, preferably potato starch, gelatin and the like. Furthermore, lubricants, such as magnesium stearate, sodium lauryl sulphate and talcum, can be used concomitantly for tabletting. In the case of aqueous suspensions and/or elixirs intended for oral administration, various taste correctives or colourings can be added to the active ingredients in addition to the above-mentioned excipients.

In the case of parenteral administration, solutions of the active ingredients using suitable liquid carriers can be employed. In general, it has been found advantageous to administer, in the case of intravenous administration, amounts of approximately from 0.01 to 2.0 mg/kg, preferably approximately from 0.01 to 1.0 mg/kg, of body weight per day to obtain effective results and, in the case of enteral administration, the dosage is approximately from 0.01 to 2 mg/kg, preferably approximately from 0.01 to 1 mg/kg, of body weight per day.

It may nevertheless be necessary in some cases to deviate from the stated amounts, depending upon the body weight of the experimental animal or the patient or upon the type of administration route, but also on the basis of the species of animal and its individual response to the medicament or the interval at which administration is carried out. Accordingly, it may be sufficient in some cases to use less than the above-mentioned minimum amount, while, in other cases, the mentioned upper limit will have to be exceeded. In cases where relatively large amounts are being administered, it may be advisable to divide those amounts into several single doses over the day. For administration in human medicine, the same dosage latitude is provided. The above remarks apply analogously in that case.

For examples of pharmaceutical formulations, specific reference is made to the examples of WO 2004/098625, pages 50-52, which are incorporated herein by reference in their entirety.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience or patentability. When any such inclusion or deletion occurs, the specification is herein deemed to contain the group as modified thus fulfilling the written description of all Markush groups used in the appended claims.

All publications, patents, patent applications, and other references cited in this application are incorporated herein by reference in their entirety for all purposes to the same extent as if each individual publication, patent, patent application or other reference was specifically and individually indicated to be incorporated by reference in its entirety for all purposes. Citation of a reference herein shall not be construed as an admission that such is prior art to the present invention.

The above disclosure describes the present invention in general. A more complete understanding can be obtained by reference to the following examples. These examples are described solely for purposes of illustration and are not intended to limit the scope of the invention. Although specific terms have been employed herein, such terms are intended in a descriptive sense and not for purposes of limitation.

EXAMPLES

Using the general strategy illustrated in FIG. 1, the development of the QPCTL constitutive Knock-out mouse lines according to the present invention comprised the following steps:
- Set up of a DNA and a concomitant sperm archive derived from male mice (F1 generation) which are progenies from matings involving a chemically mutagenized male and a wildtype female (F0 generation).
- Screening of the DNA archive for gene specific mutations using technologies which allow the detection of mutations within the target gene regions (FIG. 2).
- Characterization of the detected mutations and unequivocal identification of the mutant carrier animals.
- Reconstitution of the mutants by in vitro fertilization using sperms of the mutant carrier from the sperm archive and oocytes from wildtype females.
- Identification of the mutants using suitable genotyping assays.

Example 1

1. Mouse QPCTL Gene Characterisation

The murine QPCTL gene encodes for glutaminyl-peptide cyclotransferase-like protein, which is responsible for the presence of pyroglutamyl residues at the N-terminus of various proteins, hormones and neuroendocrine peptides.

1.1 Mouse QPCTL Locus

Figure 3:
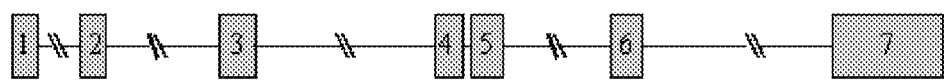
FIG. 3 shows a schematic representation of the QPCTL locus organization. The diagram is not depicted to scale. Exons are represented by grey boxes and are numbered. Solid lines represent intronic sequences.

The mouse QPCTL gene is located on chromosome 7 and extends over about 9 kbp. The C57BL/6 gene sequence is available in the Ensembl database (www.ensembl.org; ENSMUSG00000030407) and the database entry corresponds to the reference cDNA sequence NM_026111 (SEQ ID NO. 1). The exon/intron organization of the gene is also available in the Ensembl database (www.ensembl.org; ENSMUST00000032566). The QPCTL gene consists of 7 exons interrupted by 6 introns (FIG. 3). The translation initiation site is located in exon 1 and the stop codon is located in exon 7.

1.2 Mouse QPCTL Protein

The QPCTL cDNA of murine origin (SEQ ID NO. 1) encodes a protein of 383 amino acids (SEQ ID No. 2) (382 amino acids in an isoform, SEQ ID No. 3). The proteins of human, murine and rat origin share a sequence identity of approximately 80% (see also examples 3 and 6). The protein has been shown to possess an N-terminal membrane anchor, which apparently mediates retention of the protein in the Golgi apparatus. Two potential initiation codons of translation could be deduced from the primary structure. Expression of the full length cDNA and expression of an N-terminally shortened protein in cells (starting with Methionine19, the alternative initiation) did not result in changes of subcellular localization (see also examples 3 and 6), i.e the starting point of translation does not influence the subcellular localization. Moreover, the complete deletion of the N-terminal signal anchor, which was performed for expression of murine isoQC (QPCTL) in yeast, did result in secretion of enzymatically active protein. This, in fact, proves that the N-terminus is not crucial for the formation of an enzymatically active protein. The isoQC protein represents a single zinc metalloenzyme which can be inactivated by heterocyclic chelators and inhibited by imidazole, cysteamine or benzimidazole derivatives.

2. Strategy for the Development of QPCTL Knock-Out Models

The aim of the present invention—the generation of a constitutive QPCTL Knock-out model—has been achieved by chemical mutagenesis and identification of the mutant carrier using a conventional method for mutation detection. In vitro fertilization techniques involving oocytes from donor animals allowed the reconstitution of the mouse line QPCTL_L144X, which expresses a non-functional QPCTL protein fragment from cryoconserved mutant carrier sperms.

2.1 Description of Resultant Mutation

The mouse mutant QPCTL_L144X as obtained as a preferred knock-out model in the present invention carries at least one QPCTL allele where QPCTL exon 3 carries a Thymidine to Adenine (T->A) nucleotide substitution at nucleotide position 77, which corresponds to position 442 in the reference sequence NM_026111 (SEQ ID NO. 1), leading to the introduction of a stop codon into the QPCTL open reading frame. Introduction of this stop codon into the QPCTL reading frame results in a termination of polypeptide synthesis during translation at amino acid residue position 144 of the QPCTL polypeptide.

Figure 4:
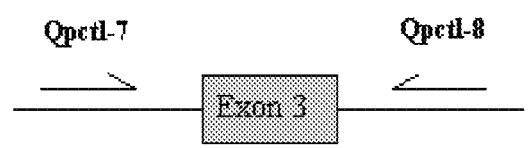
FIG. 4 shows a schematic representation of the primer binding sites used for the PCR-based identification of the QPCTL knock-out mouse mutant. The diagram is not depicted to scale. QPCTL exon 3 is represented by a grey box and the solid lines represent flanking intronic sequences. The binding sites of the primers QPCTL-7 and QPCTL-8 are indicated by arrows.

3. Method 3.1. Detection of the QPCTL L144X Mutant in the Mouse Mutant Archive 3.1.1. PCR Amplification of the Target Gene Region The first step in screening of the mutant mouse DNA archive for mutations in QPCTL exon 3 is the PCR amplification of the target gene region. For the amplification of QPCTL exon 3 a pair of primers, QPCTL-7 and QPCTL-8, was designed, which allow the PCR amplification of QPCTL exon 3 including the flanking intronic regions (FIG. 4).

3.1.2. Primer Sequences

```
                                            (SEQ ID NO: 8)
QPCTL-7: CGTGGCTCCAGTCACAAG (SEQ ID NO: 9)
QPCTL-8: TCAAGGCTAGCTTGGGCTAC
```

With each sample of the mutant mouse DNA archive, a PCR reaction was set up using primers QPCTL-7 and QPCTL-8, which results in the generation of a 473 bp DNA fragment containing the QPCTL exon 3 sequence including the flanking intronic sequences. The PCR reaction details are as follows:

Reagents:
10×PCR-Buffer.: 160 mM $(NH_4)_2SO_4$
  670 mM Tris-HCl pH 9.0
  15 mM $MgCl_2$
  0.1% Tween 20
dNTP-Mix: 25 mM each dNTP (dNTP-Mix, PCR Grade; Qiagen)
Taq-Polymerase: 5 U/µl (Taq-DNA-Polymerase; Qiagen)
Primer: 10 pmol/µl PCR-Reaction:
Template DNA: 30 ng
10×PCR-Buffer: 2.5 µl
dNTP-Mix: 0.2 µl
Primer QPCTL-7: 0.5 µl
Primer QPCTL-8: 0.5 µl
Taq-Polymerase: 0.2 µl
H$_2$O: ad 25 µl
PCR Cycling Details:

| 94.0° C.; 3 min | | | |
|---|---|---|---|
| 94.0° C.; 30 sek | 61.0° C.; 30 sek; | 72.0° C.; 90 sek | 2X |
| 94.0° C.; 30 sek | 59.0° C.; 30 sek; | 72.0° C.; 90 sek | 2X |
| 94.0° C.; 30 sek | 57.0° C.; 30 sek; | 72.0° C.; 90 sek | 2X |
| 94.0° C.; 30 sek | 55.0° C.; 30 sek; | 72.0° C.; 90 sek | 28X |
| 94.0° C.; 30 sek | 55.0° C.; 30 sek; | 72.0° C.; 10 min | |

3.1.3. Generation of Homo- and Heteroduplex Fragments

Figure 2:
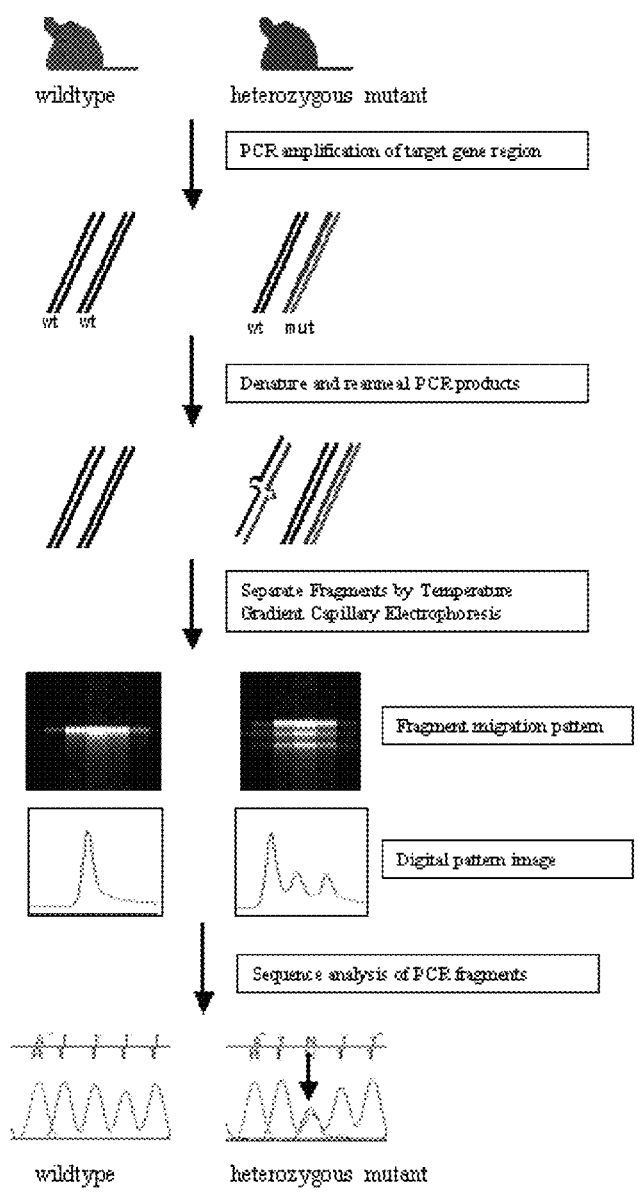
FIG. 2 shows an example for a mutation detection method for the isolation of gene-specific mutants from the mutant mouse archive. For the identification of target gene mutants from the mutant mouse archive the chromosomal target gene region of the samples is amplified by PCR. The resulting fragments are denatured, reannealed and separated by capillary electrophoresis using a spatial temperature gradient. Mismatch containing fragments from heterozygous mutants (heteroduplex fragments) exhibit a migration pattern different to wildtype fragments (homoduplex fragments). PCR products from the putative mutants are sequenced to characterize the nature of the mutation.

The basis for the electrophoretical detection of heterozygote mutants within the amplified target gene fragments as used is the presence of heteroduplex fragments (FIG. 2). PCR amplification of a heterozygous genetic locus from an ENU-derived mutant carrier results in the generation of two different types of PCR fragments, where one type is derived from the wildtype allele and the other is derived from the mutant allele. Both types of fragments may differ by one or more nucleotides in sequence. If the DNA strands of such a fragment mixture are separated by heating and allowed to re-anneal by slow cooling, the original wild type allele fragments and mutant allele fragments are reconstituted. These fragments are named homoduplex fragments because base pairing is correct throughout the fragments. However, denaturing and re-annealing generates a new type of double-stranded fragments, named heteroduplex fragments, wherein one DNA strand is derived from the wildtype allele and the other is derived from the mutant allele. Heteroduplex fragments contain base pair mismatches due to sequence differences between the wildtype and the mutant allele. Heteroduplex fragments display a melting behaviour different from homoduplex fragments due to the presence of mismatches; their differing melting behaviour can be used to discriminate homo- and heteroduplex fragments in a capillary electrophoresis with a spatial temperature gradient along the capillaries (Temperature Gradient Capillary Electrophoresis; TGCE).

Denaturing and Re-annealing Protocol:
  heat PCR reaction (see 1.1) to 95° C.
  hold 3 minutes at 95° C.
  decrease temperature from 95 to 80° C. at 3° C./minute
  decrease temperature from 80 to 55° C. at 1° C./minute
  hold 20 minutes at 55° C.
  decrease temperature from 55 to 45° C. at 1° C./minute
  decrease temperature from 45 to 25° C. at 2° C./minute 3.1.4. Detection of Heteroduplex Fragments by Temperature Gradient Capillary Electrophoresis (TGCE)

The denatured and reannealed PCR reactions (see 1.1 and 1.2 above) are diluted 1:10 with TE (10 mM Tris-HCl pH 8.0; 1 mM EDTA) and electrophoresed on a Temperature Gradient Capillary Electrophoresis unit (SCE9611 Genetic Analysis System; Transgenomic). All operating solutions for the electrophoresis unit are proprietary and not disclosed by the manufacturer. Run conditions are as follows:
Pre-Run: 10 kV for 5 min.
Sample Injection: 5 kV for 40 sec.
Run: 6.5 kV for 75 min.
Temperature gradient: 50-60° C. in 20 min. (ramp time)

The migration patterns of the fragments were recorded by camera in the SCE9611 unit and analyzed with the "Mutation Surveyor" software package (Transgenomic). Migration patterns which differ from those of a wild type control where indicative for the presence of heteroduplex fragments and hence for the presence of mutations. Heteroduplex fragments are imperfectly base paired and the mismatches lead to a retarded electrophoretical mobility especially when temperature is raised during electrophoresis (see FIG. 2). PCR fragments showing such abnormal migration patterns were selected as mutant candidate PCR fragments and further characterized by sequence analysis.

3.1.5. Sequence Analysis

Mutant candidate PCR fragments were purified by affinity chromatography (QIAquick PCR purification column; Qiagen) and the nucleotide sequences of the fragments were determined by Taq-polymerase catalyzed cycle sequencing using fluorescent-labeled dye terminator reactions. The sequencing reactions were set up as follows:
  Mutant candidate PCR fragment: 20 pg
  Terminator Ready Reaction Mix*: 4 µl
  Primer QPCTL-7 or QPCTL-8: 5 pmol
  H$_2$O: ad 25 µl
*(BigDye® Terminator v3.1 Cycle Sequencing Kit; Applied Biosystems)

The cycle sequencing reaction is carried out as follows:

| 95.0° C.; 3 min | | |
|---|---|---|
| 95.0° C.; 30 sek | 60.0° C.; 4 min; | 30X |

Prior to capillary electrophoresis the reaction mixture has to be cleaned up to remove excess dye terminator. Cleanup is done on a 96-well filter plate ((MultiScreen PCR; Millipore) as follows:
  Hydrate Sephadex G50 (Sigma) in H$_2$O
  Add 400 ul of Sephadex G-50 slurry to each well of a microtiter filter plate
  Place microtiter filter plate on top of a microtiter plate
  Spin at 1500 rpm for 2 minutes and discard flow-through
  Add 200 µl H$_2$O to each well
  Spin at 1500 rpm for 2 minutes and discard flow-through.
  Place the microtiter filter plate on top of a collection plate
  Add 10 ul terminator reaction to each Sephadex G-50 containing wells
  Spin at 1500 rpm for 2 minutes The collected effluent was electrophoresed on an ABI Prism 3700 DNA Analyzer and the resulting sequence files were inspected using the "Sequencher" DNA assembly software (version 4.0.5; Gene Codes Corporation). Using this method, heterozygous mutations were visible as overlaid peaks in the sequence chromatograms. Sequence comparison to the wild type control sequence allowed the identification of the respective nucleotide exchange in the mutant, here the T to A nucleotide exchange at position 156 of the generated PCR fragment (SEQ ID NO: 10) in the mouse mutant QPCTL_L144X (see 1.1 above) resulting in the introduction of a stop codon into the QPCTL open reading frame. The so identified mutation can be easily linked to a sperm sample in the sperm archive via the DNA identification number of the mutation, which corresponds to the same sperm identification number in the sperm archive.

3.2. Superovulation of Oocyte Donors and Oocyte Preparation

Three days before IVF 15-20 C3HFeJ female mice aged 5 weeks were intraperitoneally injected with 5 I.E. (between 4:00-5:00 pm) Intergonan to induce ovulation. Two days before the IVF the same females were mated with vasectomized male mice to induce pseudo-pregnancy. One day before IVF, the females were injected with 5 I.E. Ovogest at 6:00 pm. On day 0, 14-15 hours after the last injection the oocyte donor females are sacrificed by cervical disclosure. The mouse is put on its back and the belly disinfected with 70% alcohol. The abdomen is opened from caudal to cranial with surgical scissors. The upper end of one uterine horn is fixed with the fine forceps and the uterus, oviduct, ovary and the fad pad are pulled out. A hole is poked in the membrane close to the oviduct with the tip of the Dumont#5 forceps, to disconnect the whole reproductive tract from the body wall. The whole reproductive tract is stretched and a cut between the oviduct and the ovary is made. The oviduct is removed by cutting a small piece of the uterus with fine scissors. This step is repeated with the other uterine horn. The oviduct and the attached segment of the uterus is transferred to a prepared Petri dish (filled only with oil). Oviducts from all the female mice of the same strain are collected in one Petri dish. After dissection of all female mice from one strain, the oviducts are transferred into the Petri dish filled with 400 ml HTF medium and covered with oil. In the oil, the swollen ampullae is opened up with a closed tip of the Dumont#5 forceps, the oocyte-cumulus-complex is expelled in the oil. With the closed tip of the Dumont#5 forceps, the cumulus-complexes are pushed into the medium drop (all tissue residue or substances that could be detrimental for the spermatozoa remain outside the medium) and the Petri dish is stored in the incubator at 37° C. until the start of the fertilization.

TABLE 3

HTF Medium

| Component | mg/100 ml | source | Cat. no. |
|---|---|---|---|
| NaCl | 593.75 | Sigma | S-9888 |
| KCl | 34.96 | Sigma | P-5405 |
| $KH_2PO_4$ | 5.04 | Sigma | P-5655 |
| $MgSO_4 \cdot 7H_2O$ | 4.93 | Sigma | M-9397 |
| Sodium lactate 60% | 342 µl | Sigma | L-7900 |
| Glucose | 50.0 | Sigma | G-6152 |
| EDTA | 0.38 | Sigma | E-5134 |
| $NaHCO_3$ | 210.0 | Sigma | S-5761 |
| Glutamine | 14.5 | Sigma | G-5763 |
| Sodium pyruvate | 3.65 | Sigma | P-4562 |
| Penicillin G | 7.5 | Sigma | P-4687 |
| Streptomycin | 5.0 | Sigma | S-1277 |
| $CaCl_2 \cdot 2H_2O$ | 60.0 | Sigma | C-7902 |
| BSA | 400.0 | Sigma | A-4378 |

Preparation
All components are dissolved in 75 ml of pure water (except $CaCl_2$ and BSA)
60 mg $CaCl_2.2H_2O$ are dissolved in 25 ml water and added into the solution
BSA is sterilized by filtering through a sterile 0.22 µm Filter and added into the solution.
The solution is stored at 37° C. in the incubator with open lid in order to allow gas exchange
The osmolarity according to the manufacturer's instructions is between 270-285 mOsm.
The final working medium can be stored at 37° C. for one week 3.3.

Thawing of the Spermatozoa
The desired sperm sample corresponding to the DNA identification number of the identified mutation is taken out of the liquid nitrogen tank, and is placed in the Dewar. The thawing is performed according to Nakagata (Nakagata et al. (1993) Journal of Reproduction and Fertility 99, 77-80). The frozen straw is placed for 5 to 10 minutes in the water bath at 37° C. The straw is dried with a tissue towel and both ends are cut with scissors. One end of the straw is sealed with one finger tip and by releasing the finger the straw is emptied in a 35 cm Petri dish containing one drop HTF medium. 2 µl of the sperm suspension is given into the HTF medium drop to facilitate the sperm capacitation for one hour.

3.3. In vitro Fertilization
Under microscope inspection the washed oocyte-cumulus-complexes are transferred (with the help of a Gilson pipette and a 20 µl E-ART-tip) into the fertilization dishes containing the capacitated spermatozoa. Oocytes and spermatozoa are incubated for 4-6 hours in the incubator (37° C., 5% $CO_2$). The oocytes of each fertilization dish are washed 3 times (with the help of a silicon tube, mouth piece and drawn glass pipettes) in separate 50 µl drops of KSOM medium. The oocytes are transferred into the first drop of KSOM medium to remove all dead sperm and the residue of the cumulus complex and the washing is repeated consecutively in the other 2 drops. The oocytes are transferred into a new Petri dish filled with 200 µl KSOM medium covered with equilibrated oil and incubated overnight at 37° C. in an incubator.

The next day, the number of 2-cell embryos is evaluated under the microscope with the help of a silicon tube and glass pipettes. Only embryos which have two symmetrical blastomeres are used for embryonic transfer.

TABLE 4

KSOM Medium

| component | mg/100 ml | source | Cat. no. |
|---|---|---|---|
| NaCl | 559.5 | Sigma | S-9888 |
| KCl | 18.5 | Sigma | P-5405 |
| $KH_2PO_4$ | 4.75 | Sigma | P-5655 |
| $MgSO_4 \cdot 7H_2O$ | 4.95 | Sigma | M-9397 |
| Sodium Lactate 60% | 174 µl | Sigma | L-7900 |
| Glucose | 3.6 | Sigma | G-6152 |
| EDTA | 0.38 | Sigma | E-5134 |
| $NaHCO_3$ | 210.0 | Sigma | S-5761 |
| Glutamine | 14.5 | Sigma | G-5763 |
| Sodium pyruvate | 2.2 | Sigma | P-4562 |
| Penicillin G | 6.3 | Sigma | P-4687 |
| Streptomycin | 5.0 | Sigma | S-1277 |
| Phenol red | 0.1 | Sigma | P-3532 |
| Ess. amino acids (50x) | 1000 µl | Gibco | 11130-036 |
| Non ess. Amino acids | 500 µl | Gibco | 11140-035 |
| $CaCL_2$ | 25.0 | Sigma | C-7902 |
| BSA | 100.0 | Sigma | A-4378 |

Preparation
All components are dissolved in 70 ml of pure water (except $CaCl_2$, amino acids, and BSA)
The ess. and non ess. amino acids are added and the volume filled up to 75 ml
$CaCl_2 x 2H_2O$ is dissolved in 25 ml water and added into the solution
BSA is sterilized by filtering through a sterile 0.22 µm Filter and added into the solution.
The solution is stored at 37° C. in the incubator with open lid in order to allow gas exchange
The osmolarity according to the manufacturer's instructions is between 250-270 mOsm.
The final working medium can be stored at 37° C. for two weeks 3.4. The Embryo Transfer
The transfer should be made into the oviduct of a plug positive Foster Female at the same day of plug appearance. For the oviduct transfer the female is anaesthetized by intraperitoneal injection of 0.25 ml anaesthetic (Rompun 2% and Ketamine 10%). After 5 minutes the mouse is unconscious. During this time the embryo is prepared: The petri dish with the embryos is placed under the microscope. 1 ml mineral oil is sucked into the transfer pipette followed by a small air bubble 100 µl HTF medium/containing the embryos and another air bubble is sucked in, too.

The female pseudo-pregnant mouse is put on its stomach onto the lid of the 140 mm petri dish, and its back is wiped with 70% alcohol. A small transverse incision is made with the surgical scissors in the skin (approx. 1 cm to the left side of the spinal cord, at the level of the last rib). The peritoneum is opened up with the fine scissors. With fine forceps the fad pad is fixed and the ovary, oviduct and the uterus horn pulled out. The complex is fixed on the fad pad with the help of a bullock clamp, and layed on the back of the mouse. The mouse is placed on the stage of the microscope (head on the left side, tail to the right side). The bursa is taken with the Dumont #5 forceps and opened up with the spring scissors. The body is arranged under the microscope so that the pipette can enter easily into the infundibulum. The infundibulum is exposed and fixed with a sterile adsorption pad. The capillary already containing the embryos is carefully introduced into the infundibulum and the embryos expelled until the second air bubble has entered the ampullae. The ovary and oviduct are carefully returned into the abdomen. With one stitch the body wall is closed and the wound sealed by a wound clip. The procedure is repeated with the other side of the mouse. After surgery the mouse is placed on a warming plate for approximately 10 min and monitored afterwards in the home cage.

3.5. Breeding of IsoQC-founders

Offspring from the embryo transfer are genotyped at the age of 4 weeks and breeding initiates with heterozygous animals at a sexually mature age. To produce homozygous animals, intercross matings are initiated and the next generation subsequently genotyped. The colony is maintained by heterozygous intercross breedings.

3.7. Genotyping Assay for Mouse Line IsoQC-KO (QPCTL L144X)

For PCR and sequencing-based assessment of the QPCTL genotypes of line QPCTL-L144X the following oligonucleotide primers were designed (see FIG. 4 and Table 5):

TABLE 5

Primers useful for Genotyping of mouse line QPCTL_L144X

| Primer name | Sequence | binding region | SEQ ID No. |
|---|---|---|---|
| QPCTL-7 | CGTGGCTCCAGTCACAAG | intron 2 | 8 |
| QPCTL-8 | TCAAGGCTAGCTTGGGCTAC | intron 3 | 9 |

Figure 5:
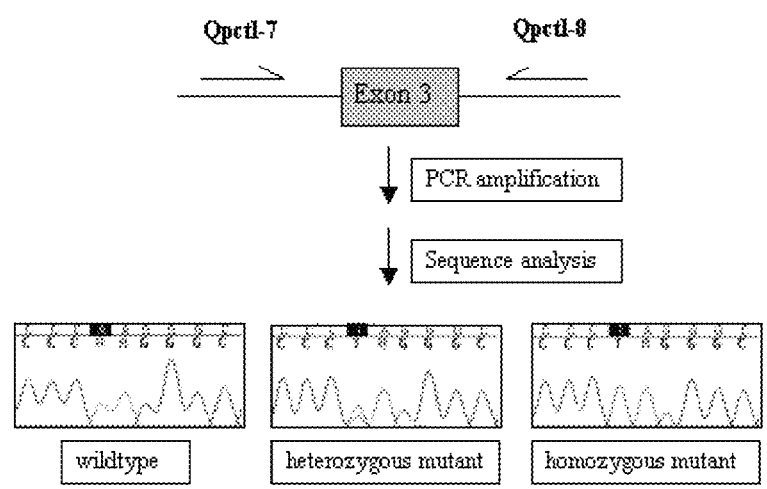
FIG. 5 shows the results of a genotyping assay for the QPCTL locus in mouse line QPCTL_L144X. The genotypes of animals from the QPCTL_L144X mouse line are determined by PCR-amplification of QPCTL exon 3 using primers QPCTL-7 and QPCTL-8 followed by sequence analysis of the generated PCR fragments. Mutants are characterized by the presence of a stop codon in the QPCTL reading frame.

In a standard PCR reaction on 100 ng chromosomal DNA containing primers QPCTL-7 and QPCTL-8, exon 3 of the QPCTL gene including the flanking regions is amplified as a 473 base pair fragment. The nucleotide sequence of the generated PCR fragment is determined in a standard sequencing reaction using either primer QPCTL-7 or QPCTL-8 and the nucleotide at position 77 in QPCTL exon 3 is identified (see FIG. 5).

Example 2

Characterization of Mice Carrying a Constitutive Knock-out Mutation in the QPCTL Gene QPCTL is not inevitable necessary for development of viable pups and development of animals, which proves that the pharmacological inhibition of QPCTL does not have obvious deleterious side effects. 98 litters resulting in 454 weaned pubs derived from heterozygous×heterozygous mating have been investigated. 430 pubs were successfully genotyped: 24.6% were wild types for the qpctl locus 57% showed heterozygous and 18.4 homozygous mutant genotypes. The 18.4% homozygous genotypes are slightly below the expected 25%. However the huge majority of homozygous animals survive into adulthood.

For behavioral characterization a phenotyping set was generated consisting of 35 males (9 wildtype, 18 heterozygous, 8 homozygous mice), which were examined in an early primary screen at about 3 months of age. At 7 months of age a selection of these mice (24 animals, n=8 for each genotype group) was investigated in a battery of 9 consecutive tests (only in 3 of these assays the whole testing group could be used).

A. Primary Screen

Methods:

The primary screen was used to prompt animals' general health, neurological reflexes and sensory functions (muscle and lower motor neuron functions, spinocerebellar, sensory, neuropsychiatric and autonomic functions) that could interfere with further behavioral assays. It was based on the guidelines of the SHIRPA protocol, which provides a behavioral and functional profile by observational assessment. The investigation started with observing social behavior in the home cage ("home cage observation") and subsequently undisturbed behavior of single animals in a clear Plexiglas arena for 90 seconds ("individual observation"). This monitoring of mouse behavior was followed by a battery of short tests for further characterization: acoustic startle reflex, hanging behavior, visual placing, falling behavior, righting reflex, postural reflex, negative geotaxis, hanging wire, ear twitch, whiskers twitch and eye blink. At last to complete the assessment animals were examined for dysmorphological and weight abnormalities.

Results:

Neither at 3 nor at 7 months of age a specific phenotype could be found in these animals, which could be correlated with a specific genotype.

B. Automated Home Cage Behavior Analysis

Methods:

Circadian patterns of locomotor activity and ingestion behavior were assessed using a PhenoMaster system (TSE Systems, Bad Homburg, Germany). Two horizontally staked infrared-sensor frames detected locomotion in the x/y-level and rearing events in the z-level, while water and food consumption were measured by two balances. All four parameters were automatically recorded as sum over 1 minute intervals for 140 hours (6.5 days). Experiments took place under a 12 hour light/dark-cycle (lights on 06:00 h, lights off 18:00 h) and animals received water and food ad libitum in individual observation units (standard type III cages with grid lid).

Results:

Compared to wildtype and heterozygous animals homozygous QPCTL knockout mice showed an increase of water consumption of about 35% over the 140 hour investigation period (FIG. 24 (*a*)). In contrast food intake was nearly identical (FIG. 24 (*b*)). In addition overall locomotor and rearing activity were slightly decreased in homozygous and heterozygous animals compared to wildtypes, but circadian patters were not altered (FIGS. 24 (*c*) and (*d*)).

C. Dark-light Box Test

Methods:

Investigation of anxiety behavior was performed using the dark-light box test, which utilizes the naturalistic conflict of mice to explore novel environments and the tendency to avoid aversive open fields. A dark-light box module (TSE Systems, Bad Homburg, Germany) consists of a Plexiglas chamber unequally divided into two compartments, a large (34×28 cm), open and brightly illuminated (700-1000 lux) compartment and a small (16×28 cm), closed and dark (1-2 lux) compartment, which are connected by a small alleyway. Animals were placed individually in the brightly lit compartment and were allowed to freely explore both compartments for 10 minutes. The duration of stay in the light compartment served as index for the level of anxiety.

Results:

No distinct differences between the three genotype groups could be demonstrated in the dark-light box test (FIG. 25).

D. Pole Assay

Methods:

The pole was used as a simple test for motor-coordinative deficits. It consisted of a metal pole (diameter: 1.5 cm; length: 50 cm) wrapped with an antislip tape, with a plastic ball on the top, and vertically installed on a heavy platform. For testing, animals were placed head-up directly under the ball and time to orient themselves down and descend the length of the pole was measured (cut-off time: 120 s). Aberrant activities (e.g. falling, jumping, sliding) were recorded as 120 s. The best performance over five trials was used for analysis.

Results:

Performance on the pole was comparable between the three genotype groups, i.e. no significant differences could be found (FIG. 26).

E. Rotarod

Methods:

The rotarod is a standard test widely used to investigate neuro-motor performance in rodents. It provides a quantitative assessment of coordination and balance, since animals must continuously walk forward on a horizontal, rotating cylinder to avoid falling off the rod. Testing was performed on two consecutive days, using a computer controlled RotaRod System (TSE Systems, Bad Homburg, Germany). In the first morning session mice were trained on a constantly rotating rod (10 revolutions per minute (rpm)) until they were able to stay on the drum for at least 60 seconds. In the afternoon and on the following day, 3 test sessions were conducted, each consisting of 3 trials. The rod-speed was accelerated from 4 to 40 rpm over a five-minute period. The total distance moved until the animal fell off was calculated automatically by the system. Performance was examined for each testing trial (motor learning), and using best trial analysis (motor coordination).

Results:

There was no clear difference in motor balance or motor learning between wildtype, heterozygous and homozygous QPCTL knockout males at an age of 7 months (FIG. 27).

F. Holeboard Test

Methods:

Mice tend to poke their noses into holes in the wall or floor. The holeboard test takes advantage of this intrinsic behavior to assess the status of exploratory behavior. Mice were placed individually into a quadratic (24×24 cm) Holeboard module (TSE Systems, Bad Homburg, Germany) with 9 equally distributed holes (1.5 cm diameter) in the floor. The number of nosepokes and the total duration of hole explorations were automatically monitored for 10 minutes.

Results:

None of the two parameters indicates an altered exploratory behavior neither in homozygous nor in heterozygous QPCTL knockout mice compared to wildtype animals (FIG. 28).

G. Tail Flick Test

Methods:

The tail flick is a spinal reflex in which the mouse moves its tail out of the path of a noxious cutaneous thermal stimulus. To assess nociception animals are tested on a TailFlick 60200 Analgesia System (TSE Systems, Bad Homburg, Germany) and tail withdrawal latency to a strong beam of focused light (circa 51° C.) was measured three times.

Results:

Neither homozygous nor heterozygous animals displayed a clearly altered nociception compared to wildtype littermates (FIG. 29).

H. Constant Hotplate

Methods:

Tests for acute thermal pain sensitivity were performed on a constant hotplate (TSE Systems, Bad Homburg, Germany). Mice were placed in a Plexiglas cylinder on the 52.5° C. warm surface of the hotplate, and hind paw withdrawal latency (or shaking/licking of the hind paw) was measured two times (non-habituated vs. habituated). First measurements took place without former habituation. After habituation on a 32.0° C. hot plate animals were retested. Cutoff-time was 60 seconds.

Results:

In QPCTL knockout males aged 7 months no statistically significant differences could be found in the hotplate performance between homozygous, heterozygous and wildtype animals—neither in the non-adapted nor in the adapted trial. Only a weak tendency of homozygous animals for lower reaction latencies was detected (FIG. 30 *a*).

In addition to the male phenotyping set, different animal groups were tested in single assays: the investigation of very young QPCTL knockout mice (7 weeks of age) on the constant hotplate (only non-adapted trial) revealed no significant differences in males but significantly decreased latencies in homozygous and heterozygous females compared to wildtyp littermates (FIG. 30 *b*).

A female set consisting of 10 homozygous and 10 wildtype animals was examined in the primary screen at about 4 and 6 months of age and, like the males, displayed no genotype-specific differences in all measured parameters.

Example 3

Immunohistochemical Analysis of QPCTL Knock-out

Methods

Two months-old mice (QPCTL knock-out and wildtype) were euthanized with carbon dioxide and perfused transcardially with washing buffer, consisting of 137 mM NaCl, 22 mM Dextrose, 23 mM Sucrose, 0.2 mM $CaCl_2$, and 0.2 mM Sodium Cacodylate, pH 7.3. The brains were perfused and postfixed with fixation buffer, consisting of 1.3M Paraformaldehyde, 0.2M Sucrose, and 104 mM Sodium Cacodylate. The brains were dissected, postfixed, and embedded together in a gelatine multibrain matrix. The brains were freeze-sectioned (30 µm) using a sliding microtome. All stainings were made free floating using the two step DAB method. For QPCTL staining as primary antibody the affinity purified polyclonal isoQC3285 (Probiodrug) made in rabbit was used 1:1.000. For NeuN staining as primary antibody the monoclonal b-NeuN (AbCam) made in mouse was used 1:1.500. For GFAP staining as primary antibody the polyclonal GFAP (Dako) made in rabbit was used 1:50.000. For Iba1 staining as primary antibody the polyclonal Iba-1 (Wako) made in rabbit was used 1:10.000. For each staining the appropriate biotinylated secondary antibody was used at a delution of 1:250.
Results:

Wild-type animals showed an ubiquitous neuronal signal in the whole brain, while the staining was clearly diminished in QPCTL-KO animals (FIG. 31, Coronal section of the hippocampus).

The immunohistochemical signal in the brains of QPCTL knockout mice showed no difference compared to wildtype littermates stained with NeuN, Iba1, and GFAP. NeuN staining, a marker for neuronal loss in the hippocampal CA1 region shows no evidence for Neurodegeneration (FIG. 32). As both Gliosis marker, Iba1 for Microglia (FIG. 34) and GFAP for Astroliga (FIG. 33), show no increased signals in the hippocampal CA1 Region of QPCTL knockout mice, there is no evidence for Neuroinflammation in these mice. As positive control the brains of two months-old mice overexpressing AβN3Q-42 (see WO 2009/034158) were used (FIGS. 32-34).

Example 4

Effect of QPCTL Knock-out on the QC-activity in Brain

Figure 6:
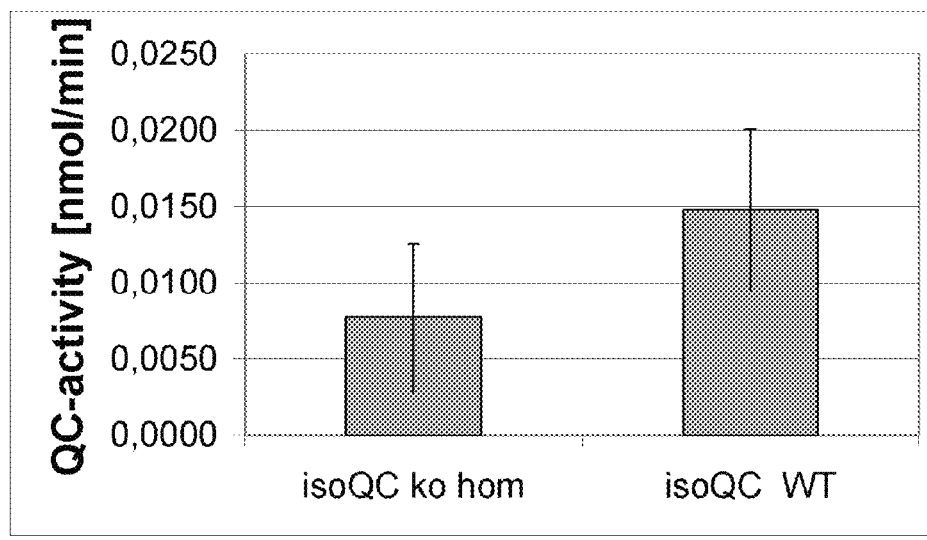
FIG. 6 shows the QC-activity, which was determined in hemibrains of QPCTL wild-type and knock-out mice. A lower activity was determined in the knock-out animals, implying a succesfull isoQC knock-out generation.

The effect of QPCTL depletion on the QC-activity in brain has been assessed by QC activity analysis in brain homogenates.
Methods:
Tissue Preparation Frozen hemibrains were thawed and 500 µl of sample buffer, consisting of 10 mM Tris, pH 7.5, 100 mM NaCl, 5 mM EDTA, 0.5% Triton, 10% Glycerol added. The tissue was homogenized using a bead mill (precellys 24) at 6500 rpm for two times, 30 s each. Afterwards, the samples were centrifuged at 7.000 rpm for 6 min. The beads were washed with 500 µl of sample buffer and the samples subjected to sonication for 10 s. The homogenate was finally centrifuged at 13.000×g for 30 min. The protein concentration in the supernatant was determined and adjusted to 2.5 to 5 mg/ml.
HPLC Assay The assay is based on conversion of H-Gln-βNA to pGlu-βNA. The sample consisted of 50 µM H-Gln-βNA in 25 mM MOPS, pH 7.0, 0.1 mM N-ethylmaleinimide (NEM) and enzyme solution in a final volume of 1 ml. Samples were incubated at 30° C. and constantly shaken at 300 rpm in a thermomixer (Eppendorf). Test samples were removed, and the reaction stopped by boiling for 5 min followed by centrifugation at 16.000×g for 10 min. All HPLC measurements were performed using a RP18 LiChroCART HPLC Cartridge and the HPLC system D-7000 (Merck-Hitachi). Briefly, 10 µl of the sample were injected and separated by an increasing concentration of solvent A (acetonitrile containing 0.1% TFA) from 8% to 20% in solvent B (H$_2$O containing 0.1% TFA). QC activity was quantified from a standard curve of pGlu-βNA (Bachem) determined under assay conditions.
Results:

The QC-activity in brains of homozygous QPCTL-L144X knock out mice and wild-type littermates was determined and compared. The QC-activity in the brains of the homozygous k.o. animals was approximately half of the activity of the wild-type animals, efficiently proving that QPCTL activity was depleted (FIG. 6). The remaining QC activity is caused by the enzyme QPCT.

Example 5

Subcellular Localization of Rat and Mouse IsoQC

A. Cloning procedures

For the cloning for EGFP-tagged rat and mouse isoQC, the EGFP sequence of vector pEGFP-N3 (Invitrogen) was introduced into vector pcDNA 3.1 (Invitrogen) using primers 1 (sense) (SEQ ID NO: 15) and 2 (antisense) (SEQ ID NO: 16) (see Table 6 below) for amplification. The fragment was introduced into the XhoI site of pcDNA 3.1. The generated vector was termed pcDNA-EGFP. The cDNA of the native mouse-isoQC starting either at MetI (SEQ ID NO: 1) or MetII (SEQ ID NO: 11) and rat-isoQC starting either at MetI (SEQ ID NO: 4) or MetII (SEQ ID NO: 12) was fused C-terminally in frame with EGFP in vector pcDNA-EGFP. The primers 3 (sense) (SEQ ID NO: 17) and 4 (antisense) (SEQ ID NO: 18) (Table 6) were used for amplification of mouse-isoQC cDNA starting with MetI (SEQ ID NO: 1) and primers 5 (sense) (SEQ ID NO: 19) and 4 (antisense) (SEQ ID NO: 18) (Table 6) were used for amplification of mouse-isoQC cDNA starting with MetII (SEQ ID NO: 11). Primers 6 (sense) (SEQ ID NO: 20), 7 (antisense) (SEQ ID NO: 21) and 5 (sense) (SEQ ID NO: 19) and 7 (antisense) (SEQ ID NO: 21) (Table 6) were used for amplification of rat-isoQC DNA starting with MetI (SEQ ID NO: 4) and MetII (SEQ ID NO: 12), respectively. The fragments were inserted into vector pcDNA-EGFP employing the restriction sites of EcoRI and NotI and correct insertion of the fragments was confirmed by sequencing. The N-terminal sequences of mouse-isoQC beginning at MetI and MetII each ending at serine 55 (counting from MetI) (of both SEQ ID NO's: 2 and 13) and rat-isoQC beginning at MetI and MetII each ending at serine 55 (counting from MetI) (of both SEQ ID NO's: 5 and 14) were also fused C-terminally with EGFP in vector pcDNA-EGFP using primer 3 (sense) (SEQ ID NO: 17) and primer 8 (antisense) (SEQ ID NO: 22) (Table 6) for the N-terminal fragment of mouse-isoQC beginning with MetI and primer 5 (sense) (SEQ ID NO: 19) and primer 8 (antisense) (SEQ ID NO: 22) (Table 6) for the fragment starting with MetII. The N-terminal fragments of rat-isoQC were amplified using primer 6 (sense) (SEQ ID NO: 20) and primer 9 (antisense) (SEQ ID NO: 23) (Table 6) for starting with MetI, and primer 5 (sense) (SEQ ID NO: 19) and primer 9 (antisense) (SEQ ID NO: 23) (Table 6) for starting with MetII. Subsequently, all vectors were isolated for cell culture purposes using the EndoFree Maxi Kit (Qiagen.

TABLE 6

Oligonucleotide primers used for cloning of m-isoQC and r-isoQC into vector pcDNA 3.1

| Primer | Sequence (5'→3'), restriction sites (underlined) | Purpose | SEQ ID NO: |
|---|---|---|---|
| 1 | ATAT<u>CTCGAG</u>TCCATCGCCACCATGGTGAGC | Amplification of EGFP | 15 |
| 2 | ATAT<u>CTCGAG</u>TTACTTGTACAGCTCGTCCAT | Amplification of EGFP | 16 |

TABLE 6-continued

Oligonucleotide primers used for cloning of m-isoQC and r-isoQC into vector pcDNA 3.1

| Primer | Sequence (5'→3'), restriction sites (underlined) | Purpose | SEQ ID NO: |
|---|---|---|---|
| 3 | ATAT<u>GAATTC</u>ATGAGTCCCGGGAGCCGC | Amplification of m-isoQC starting with MetI | 17 |
| 4 | ATAT<u>GCGGCCGC</u>ATGAGTCCCAGGTACTCGGCCAG | Amplification of m-isoQC lacking the stop codon | 18 |
| 5 | ATAT<u>GAATTC</u>ATGAAACCACCCTCACTT | Amplification of m-isoQC and r-isoQC starting with MetII | 19 |
| 6 | ATAT<u>GAATTC</u>ATGAGTCCGGCCAGCCGC | Amplification r-isoQC starting with MetI | 20 |
| 7 | ATAT<u>GCGGCCGC</u>ATGAGACCCAGGTACTCAGCCAG | Amplification of r-isoQC lacking the stop codon | 21 |
| 8 | ATAT<u>GCGGCCGC</u>ATGCTGTTCCAGACGATATAGAAAGC | Amplification of m-isoQC N-terminal sequence | 22 |
| 9 | ATAT<u>GCGGCCGC</u>ATGCTATTCCAGACGATATAAAAAGC | Amplification of r-isoQC N-terminal sequence | 23 |

B. Cultivation and Transfection of Mammalian Cells

The human astrocytoma cell line LN405 and the human neuroblastoma cell line SH-SY5Y were cultured in appropriate cell culture media (Dulbecco's modified Eagle medium, 10% fetal bovine serum), in a humidified atmosphere of 10% $CO_2$ at 37° C. For transfection, LN405 and SH-SY5Y cells were cultured in 2-well chamber slides (BD Falcon), grown until 80% confluency and transfected by incubation in a solution containing Lipofectamin2000 (Invitrogen) and the respective plasmids (as obtained above in Step A) according to the manufacturer's manual. The solution was replaced with appropriate growth media after 5 h and cells were grown overnight.

C. Histochemical Analysis

For histochemical analysis LN405 and SH-SY5Y cells were washed twice with D-PBS (Invitrogen), one day after transfection and fixed using ice-cold methanol for 10 min at −20° C., followed by three washing steps of D-PBS for 5 min at room temperature. For the staining of the Golgi complex, LN405 and SH-SY5Y cells were incubated with anti-mannosidase II polyclonal antibody (Chemicon) in a 1:100 dilution of antibody in D-PBS for 3 h at room temperature. Subsequently, the cells were washed three times with D-PBS for 5 min. The cells were incubated with goat anti-rabbit IgG secondary antibody conjugated with Cy3 at room temperature in the dark for 45 min. Afterwards, the samples were washed three times with D-PBS for 5 min and were incubated with 1 μg/ml 4',6-Diamidin-2'-Phenylindole-(DAPI) solution (Roche) for two minutes for staining of the nucleus and washed once with D-PBS. The coverslips were mounted on the microscope slide with Citifluor (Citiflour Ltd., Leicester, UK). Cells were observed with a confocal laser scanning microscope (Carl-Zeiss).

D. Results

In order to investigate the subcellular localization of mouse-isoQC and rat-isoQC in mammalian cells and the relevance of the putative start methionines, mouse-isoQC-EGFP and rat-isoQC-EGFP fusions beginning either at methionine I (MetI) or at methionine II (MetII) were generated. Human LN405 and SH-SY5Y cells were transiently transfected and the subcellular distribution was examined using confocal laser scanning microscopy. The expression of mouse-isoQC (MetI)-EGFP and rat-isoQC-(MetI)-EGFP fusion proteins resulted in a distinct staining close to the nucleus of virtually all cells expressing the transgene (FIGS. 7a, 8a, 9a and 10a). Counterstaining of cellular mannosidase II revealed the presence of mouse-isoQC (MetI)-EGFP and rat-isoQC (MetI)-EGFP within the Golgi complex in LN405 and SH-SY5Y. Expression of mouse-isoQC (MetII)-EGFP and rat-isoQC (MetII)-EGFP fusion proteins resulted in a very similar fluorescence staining, which matched well with the localization of mannosidase II (FIGS. 7a, 8a, 9a and 10a). Thus, the subcellular distribution of mouse-isoQC and rat-isoQC is independent of the N-terminal methionine.

In order to clarify whether the predicted N-terminal signal anchor is responsible for the retention of mouse-isoQC and rat-isoQC within the Golgi complex, the signal peptides starting at MetI and MetII, including the putative signal anchor sequences, were cloned in-frame with EGFP. The resulting vectors mouse-isoQC (MetI) signal sequence (SS) EGFP, mouse-isoQC (MetII) SS EGFP, rat-isoQC (MetI) SS EGFP and rat-isoQC (MetII) SS EGFP were expressed in LN405 and SH-SY5Y cells as described before and the expression was also analyzed by confocal laser scanning microscopy. The expression of the four vectors led to the same Golgi complex localization that was observed for the full length fusion proteins (FIGS. 7b, 8b, 9b and 10b). Consequently, the N-terminal sequence of isoQC leads to the co-translational translocation of the mouse-isoQC and rat-isoQC to the membrane of the endoplasmatic reticulum and to the retention within the Golgi complex. Furthermore, due to the expression of mouse-isoQC (MetII) SS EGFP and rat-isoQC (MetII) SS EGFP, the Golgi retention signal can be grossly mapped between residues methionine 19 and serine 55 of both, SEQ ID NO's: 2 and 5

The results provide evidence for an identical localization of isoQCs from different mammals, proving that the inventive animal model has predictive value for the human situtation.

Example 6

Gene Expression of QC (QPCT) and IsoQC (QPCTL) in RAW264.7 and THP-1 Cells

A. Characterization of RAW264.7 Cells

The murine monocyte/macrophage cell line RAW264.7 (in the following: RAW) was obtained from CLS (Eppelheim, Germany). RNA was isolated using the NucleoSpin RNA II kit (Macherey Nagel) according to the manufacturer's instructions. Constant 1000 ng of RNA were reversely transcribed to cDNA using random primers (Roche) and Superscript II (Invitrogen). Quantitative real-time PCR was performed in a Rotorgene3000 (Corbett Research) using the QuantiTect SYBR Green RT-PCR kit (Qiagen). Applied primers are depicted in table 7A.

An initial 15 min activation step at 95° C. was performed, followed by 45 cycles of 15 sec denaturation at 95° C., annealing for 20 sec at 60° C. (for Qiagen primers at 55° C.), and 20 sec extension at 72° C. Gene expression was determined with the Rotorgene software version 4.6 in quantitation mode. For verification of the PCR, product melting curves were generated and amplicons were confirmed by agarose gel electrophoresis.

B. Characterization of THP-1 Cells

THP1 (human acute monocytic leukemia) cells were obtained from CLS (Eppelheim, Germany). RNA isolation, cDNA synthesis and PCR were done as described for RAW cells. Primers used for quantification of human QPCT and human QPCTL are depicted in table 8.

C. Results

Using primer pairs, which are amplifying products within exon 1 of murine QPCT (mQPCT), PCR products could be obtained (FIG. 11(a), primer pairs F5/R6 (SEQ ID NO's: 24 and 27), F5/R14 (SEQ ID NO's: 24 and 28), F5/R16 (SEQ ID NO's: 24 and 29); see Table 7A). In contrast, primer pairs binding to the regions of exon 2 to exon 7 did not result in the detection of products with cDNA isolated from RAW cells (FIG. 11(a), primer pairs F5/R12 (SEQ ID NO's: 24 and 30), F5/R20 (SEQ ID NO's: 24 and 31), F3/R4 (SEQ ID NO's: 25 and 32), F3/R20 (SEQ ID NO's: 24 and 31), F3/R2 (SEQ ID NO's: 24 and 33), F11/R22 (SEQ ID NO's: 26 and 34), Table 7A, primers obtained from Qiagen). All primer pairs amplified products with cDNA isolated from B16 murine melanoma cells as well as from murine brain tissue. Consequently, RAW cells did not express full-length mQPCT mRNA. RAW cells, B16 cells as well as murine brain tissue expressed murine QPCTL (mQPCTL) (Table 7B, FIG. 11(a). RAW cells did not express full-length mQPCT RNA but expressed mQPCTL; therefore, this cell line is a useful tool for in vitro testing of inhibitors of the mQPCTL activity

TABLE 7A

Oligonucleotides for amplification of murine QPCT and murine QPCTL

| 5' Primer | Sequence | SEQ ID NO: | 3' Primer | Sequence | SEQ ID NO: |
|---|---|---|---|---|---|
| mQPCT NM_027455 *Mus musculus* glutaminyl-peptide cyclotransferase (glutaminyl cyclase) (QPCT), mRNA | | | | | |
| F5 | GGGAGGCAGACACAATCAAT | 24 | R6 | TCAGATTCCCAGCTGTCAGA | 27 |
| F5 | GGGAGGCAGACACAATCAAT | 24 | R14 | GCAGCGGAGACCAGACTCA | 28 |
| F5 | GGGAGGCAGACACAATCAAT | 24 | R16 | AGGCAGCGGAGACCAGA | 29 |
| F5 | GGGAGGCAGACACAATCAAT | 24 | R12 | GGTTGGTGGTGGTTCTTCTC | 30 |
| F5 | GGGAGGCAGACACAATCAAT | 24 | R20 | CTGAATTCGTTGCATGATGTG | 31 |
| F3 | TCTGACAGCTGGGAATCTGA | 25 | R4 | CCCACTCAGCCTGAAGTCTC | 32 |
| F3 | TGACAGCTGGGAATCTGAGT | 25 | R20 | CTGAATTCGTTGCATGATGTG | 31 |
| F3 | TGACAGCTGGGAATCTGAGT | 25 | R2 | CTTCCGGGTTAAGAGTGCTG | 33 |
| F11 | GGCATGGATCTGTTGGTCTT | 26 | R22 | GTGCCAGACTTCAGGGAAAG | 34 |

TABLE 7A-continued

Oligonucleotides for amplification of murine QPCT and murine QPCTL

| 5' Primer | Sequence | SEQ ID NO: | 3' Primer | Sequence | SEQ ID NO: |
|---|---|---|---|---|---|
| Qiagen QT01057056 mQPCT | | | | | |
| mQPCTL NM_026111 *Mus musculus* glutaminyl-peptide cyclotransferase-like (QPCTL), mRNA | | | | | |
| QPCTL-F | GCTATGGGCTTGGCTTTCTA | 35 | QPCTL-R | CAATAAGGGACGCAGGAAAG | 36 |

TABLE 7B

Results of the amplification of murine QPCT and murine QPCTL mQPCT NM_027455 Mus musculus glutaminyl-peptide cyclotransferase (glutaminyl cyclase) (Qpct), mRNA

| 5' Primer | 3' Primer | Product [bp] | Found in Brain tissue | Found in B16 cells | Found in RAW cells | Amplified exons |
|---|---|---|---|---|---|---|
| F5 | R6 | 211 | Yes | Yes | Yes | 1 |
| F5 | R14 | 227 | Yes | Yes | Yes | 1 |
| F5 | R16 | 229 | Yes | Yes | Yes | 1 |
| F5 | R12 | 257 | Yes | Yes | No | 1/2 |
| F5 | R20 | 410 | Yes | Yes | No | 1/3 |
| F3 | R4 | 239 | Yes | Yes | No | 1/2 |
| F3 | R20 | 218 | Yes | Yes | No | 1/3 |
| F3 | R2 | 218 | Yes | Yes | No | 1/3 |
| F11 | R22 | 273 | Yes | Yes | No | 4/7 |
| Qiagen | | 104 | Yes | Yes | No | 5/6 | mQPCTL NM_026111 Mus musculus glutaminyl-peptide cyclotransferase-like (QPCTL), mRNA

| 5' Primer | 3' Primer | Product [bp] | Found in Brain tissue | Found in B16 cells | Found in RAW cells | Amplified exons |
|---|---|---|---|---|---|---|
| QPCTL-F | QPCTL-R | 180 | Yes | Yes | Yes | 1/2 |

In addition, human THP1 cells expressed both human QPCT (hQPCT) mRNA as well as human QPCTL (hQPCTL) mRNA. Treatment of THP1 cells with LPS (1 µg/ml) for 24 h increased hQPCT mRNA levels, whereas hQPCTL RNA showed constant levels (FIG. 12). THP1 cells can be used as a human in vitro screening model for QPCT (QC) and QPCTL (isoQC) inhibitors.

TABLE 8

Oligonucleotides for amplification of human QPCT and human QPCTL

| Primer | Product [bp] | Amplified exons | Amplification THP-1 cells |
|---|---|---|---|
| NM_012413 *Homo sapiens* glutaminyl-peptide cyclotransferase (QPCT), mRNA | | | |
| Qiagen QT00013881 hQPCT | 108 | 3/4 | Yes |
| NM_017659 *Homo sapiens* glutaminyl-peptide cyclotransferase-like (QPCTL), mRNA | | | |
| Qiagen QT00074074 hQPCTL | 120 | 2/3 | Yes |

Example 7

Potency of Different IsoQC-inhibitors in RAW264.7 and THP-1 Cells

A. Inhibition of pGlu-MCP-1 Formation in RAW264.7

The mouse monocyte/macrophage cell line RAW264.7 was used to investigate the effect of glutaminyl cyclase (QC) inhibitors on the formation of the N-terminal pyroglutamate (pGlu) of MCP-1 secreted by the cells after LPS stimulation. 40.000 cells/100 µl were seeded per well in a 96-well microplate and grown in DMEM (Invitrogen) containing 10% FBS and Gentamycin (Invitrogen). After 24 h the medium was changed to 150 µl DMEM/10% FBS/Gentamycin containing an appropriate concentration of inhibitor or control (DMSO). For inhibitor screening experiments the test compounds were used in a final concentration of 10 µM. Four replicates were performed for each compound. 30 min after inhibitor application cells were stimulated by addition of LPS (10 ng/ml, from *E. coli* strain 055:B5, Sigma). 24 h after LPS stimulation, the supernatant was harvested and stored at −20° C. until analysis of MCP-1. Total MCP-1 and pGlu1-MCP-1 (mMCP-1 N1pE) were determined by specific ELISAs. (See Example 5B below)

B. ELISA for Detection of Total mMCP-1 and mMCP-1 N1pE

For determination of total mMCP-1 and mMCP-1 N1pE, specific ELISAs were developed. Briefly, 25 ng of capture antibody rabbit-anti mJE (Peprotech) were coated per well of a 96 well plate in coating buffer (PBS, pH 7.4). Plates were incubated over night at room temperature. Afterwards, each well was blocked for 2 h by addition of 200 µl blocking buffer (protein free (TBS) blocking buffer (Perbio)) and then washed 3 times using 300 µl of wash buffer (protein free T20 (TBS) blocking buffer (Perbio)). Standard peptides (Peprotech) and samples were diluted using dilution buffer (protein free T20 (TBS) blocking buffer)) and 100 µl were applied onto the test plate. The incubation of test samples and standard peptides was carried out for 2 h at room temperature and afterwards the plate was washed 3 times using wash buffer. For detection of mMCP-1 N1pE, anti-pE1-MCP-1 specific monoclonal antibody clone 4B8 (produced by Probiodrug, 0.65 mg/ml) was applied in a concentration of 0.25 µg/ml in combination with anti-mouse-HRP conjugate (KPL) in a dilution of 1:2000. For the detection of total MCP-1, rat-anti mouse MCP-1 (R&D Systems, 1 mg/ml) was applied in a concentration of 0.25 µg/ml in combination with anti-rat-HRP conjugate (Sigma) in a dilution of 1:2.000. Antibodies were diluted in dilution buffer, applied in a volume of 100 µl to each well and incubated for 2 h at room temperature. Thereafter, wells were washed 5 times with 300 µl of wash buffer followed by application of the chromogen SureBlue (KPL) in a volume of 100 µl to each well. After incubation in the dark for 30 min, the reaction was abrogated using 50 µl Stop Solution (1.2 N H$_2$SO$_4$) and absorption was determined at 450 nm. The reference wavelength of 550 nm was subtracted from sample absorption at 450 nm.

C. Results

Using the mMCP-1 N1pE assay in RAW264.7 cells, the efficacy of QC inhibitors to suppress the formation of pGlu1-MCP-1 by the mouse-QC-negative and mouse-isoQC-positive cell line RAW264.7 could be demonstrated. A correlation of the inhibitory constants for human-isoQC with the inhibition of pGlu-MCP-1 formation was found. Only compounds, which show a strong inhibition of isoQC (K$_i$<100 nM) are capable of efficiently inhibiting the formation of pGlu-MCP-1, whereas strong QC but weak isoQC inhibitors show only weak cellular potency in inhibiting pGlu-MCP-1 formation in RAW264.7 cells.

inserted into the yeast expression vector, as shown in FIG. 13) was fused in frame with the pPiCZαA-plasmid-encoded α-factor secretion signal, directing the protein into the secretory pathway. After amplification of mouse-isoQC utilizing the primer 10 (sense) (SEQ ID NO: 37) and primer 11 (antisense) (SEQ ID NO: 38) (Table 9), the fragment was inserted into the expression vector employing the restriction sites of NotI and EcoR I. For insertion of a glycosylation site, a mutation was introduced in codon 56 (Ile56Asn) of the open reading frame of isoQC (again assuming that methionine II is the first amino acid of the protein) by primers 12 (sense) (SEQ ID NO: 39) and 13 (antisense) (SEQ ID NO: 40) (Table 9). The mutagenesis was performed according to standard PCR techniques followed by digestion of the parent DNA using DpnI (quik-change II site-directed mutagenesis kit, Stratagene, Catalog No. 200524).

TABLE 9

Oligonucleotides used for cloning and mutation of murine isoQC

| Oligo-nucleo-tide | Sequence (5'→3'), restriction sites (underlined) | Purpose | SEQ ID NO: |
|---|---|---|---|
| 10 | ATAT<u>GAATTC</u>GAGGAGATGTCACGGAGC | Amplification of m-isoQC starting with Glu 43 | 37 |
| 11 | ATATAT<u>GCGGCCGC</u>CTAGAGTCCCAGGTACT CGGC | Amplification of m-isoQC for insertion into pPICZαA vector | 38 |
| 12 | GATCTGCGGGTCCCGCTGAACGGAAGCCTTT CAGAAGCC | Change of Ile 56 to Asn | 39 |
| 13 | GGCTTCTGAAAGGCTTCCGTTCAGCGGGACC CGCAGATC | Change of Ile 56 to Asn | 40 |

Thus, the RAW cells provide an excellent system to investigate the inhibition of isoQC independently from potentially disturbing influences of substrate conversion by QC.

Example 8

Methods for the Isolation and Characterization of IsoQC from Murine Origin Including Methods for Protein Detection by Western-blot A. Host Strains and Media Escherichia coli strain DH5α was used for propagation of plasmids and P. pastoris strain X-33 was used for the expression of human isoQC in yeast. E. coli and P. pastoris strains were grown, transformed and analyzed according to the manufacturer's instructions (Qiagen (DH5α), invitrogen (X-33)). The media required for E. coli, i.e. Luria-Bertani (LB) medium, was prepared according to the manufacturer's recommendations. The media required for Pichia pastoris, i.e. BMMY, BMGY, YPD, YPDS and the concentration of the antibiotics, i.e. Zeocin, were prepared as described in the Pichia Manual (Invitrogen, catalog. No. K1740-01). The manual also includes all relevant descriptions for the handling of yeast.

B. Molecular Cloning of Plasmid Vectors Encoding the Mouse IsoQC

All cloning procedures were performed applying standard molecular biology techniques. For expression in Pichia pastoris X-33, the pPiCZαA vector (Invitrogen) was used. The cDNA of the mature mouse isoQC starting with codon 43 (Glu 43) of the open reading frame (counting from methionine II, i.e. the transmembrane sequence is omitted and not C. Transformation of P. pastoris and Mini-Scale Expression 1-2 µg of plasmid DNA were applied for transformation of competent P. pastoris cells by electroporation according to the manufacturer's instructions (BioRad). Selection was done on plates containing 100 µg/ml Zeocin. In order to test the recombinant yeast clones for mouse-isoQC expression, cells were grown for 24 h in 10 ml conical tubes containing 2 ml BMGY. Afterwards, the yeast was centrifuged and resuspended in 2 ml BMMY containing 0.5% methanol. This concentration was maintained by addition of methanol every 24 h for about 72 h. Subsequently, QC activity in the supernatant was determined. Clones that displayed the highest activity were chosen for further experiments and fermentation.

D. Expression and Purification of M-isoQC in Pichia pastoris

Figure 14:
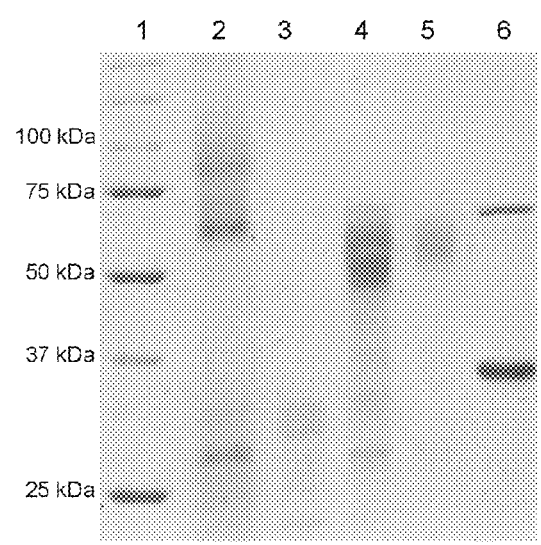
FIG. 14 shows the SDS-PAGE analysis illustrating the purification of mouse-isoQC after fermentation. Proteins were visualized by Coomassie staining. Lane 1, molecular mass standards (kilodaltons) (Dual Color, Bio-Rad); lane 2, supernatant after expression; lane 3, mouse-isoQC containing fractions after initial hydrophobic interaction chromatography in expanded bed modus; lane 4, mouse-isoQC after hydrophobic interaction chromatography; lane 5, mouse-isoQC after UnoQ column. lane 6 mouse-isoQC after gel filtration and treatment with deglycosylation enzyme EndoHF. The isoQC protein corresponds to a protein between 50 kDa and 70 kDa. The deglycosylated protein corresponds to a protein band at 37 kDa. The mouse-isoQC was purified to homogeneity.

Large scale-expression of isoQCs in Pichia pastoris was performed in a 5 L reactor (Biostad B; Braun Biotech, Melsungen, Germany). Briefly, the fermentation was carried out in basal salt medium supplemented with trace salts at pH 5.5. Initially, the biomass was accumulated in a batch and a fed-batch phase with glycerol as the sole carbon source for about 28 h. Expression of the isoQCs was initiated by methanol-feeding according to a three-step profile recommended by Invitrogen for an entire fermentation time of approximately 65 h. After expression, the cells were separated from the medium by centrifugation (8.000×g, 20 min), and the pellet was discarded. Ammonia was added to the supernatant to a final concentration of 0.8 M, subsequently again centrifuged and the resulting supernatant was further used for the first purification step. The isoQC proteins were purified utilizing a 4-step protocol (Table 10). Purified protein was used for determination of QC activity and analysis of metal content. The purification is illustrated in FIG. 14.

TABLE 10

Scheme of the purification of mouse isoQC following expression in *P. pastoris*.

| | Purification Step | | | |
|---|---|---|---|---|
| | 1 | 2 | 3 | 4 |
| Method | HIC-EBA | HIC | IEX | SEC |
| Column type (Amersham Biosciences AB, Sweden) | STREAMLINE Butyl | Butyl Sepharose 4 Fast Flow | UNO Q | Superdex 75 prep grade |
| Column size | d = 2.5 cm<br>l = 42 cm<br>CV = 206 cm³ | d = 2.6 cm<br>l = 10 cm<br>CV = 53 cm³ | d = 1.2 cm<br>l = 5.3 cm<br>CV = 6 cm³ | d = 2.6 cm<br>l = 87 cm<br>CV = 461 cm³ |
| Equilibration Buffer | 50 mM NaH₂PO₄ 0.8M (NH₄)₂SO₄ | 50 mM NaH₂PO₄ 0.7M (NH₄)₂SO₄ | 30 mM Bis-Tris | 30 mM NaH₂PO₄ |
| pH | 7.0 | 7.0 | 6.8 | 7.0 |
| Volume | 4 CV | 4 CV | 5 CV | 2 CV |
| Intermediate (Wash) Buffer | 50 mM NaH₂PO₄ 0.8M (NH₄)₂SO₄ | 50 mM NaH₂PO₄ 0.7M (NH₄)₂SO₄ | 30 mM Bis-Tris | — |
| pH | 7.0 | 7.0 | 6.8 | |
| Volume | 5 CV | 4 CV | 4 CV | |
| Elution Buffer | 50 mM NaH₂PO₄ | 50 mM NaH₂PO₄ gradient from 0.7-0M AS | 30 mM Bis-Tris; 3M NaCl (0-15% gradient) | 30 mM NaH₂PO₄ 0.5M NaCl |
| pH | 7.0 | 7.0 | 6.8 | 7.0 |
| Volume | 1.5 CV | 5 CV | 10 CV | 1.5 CV |

E. Fluorometric Assays and Spectrophotomeric Assay for the Determination of QC Activity Fluorometric Assays All measurements were performed with a NovoStar reader for microplates (BMG Labtechnologies) at 30° C. QC activity was evaluated fluorometrically using H-Gln-βNA. The samples consisted of 0.2 mM fluorogenic substrate, 0.25 U pyroglutamyl aminopeptidase (Qiagen, Hilden, Germany) in 0.05 M Tris/HCl, pH 8.0 and an appropriately diluted aliquot of isoQC in a final volume of 250 µl. Excitation/emission wavelengths were 320/410 nm. The assay reactions were initiated by addition of glutaminyl cyclase. isoQC activity was determined from a standard curve of β-naphthylamine under assay conditions. One unit is defined as the amount of isoQC catalyzing the formation of 1 µmol pGlu-βNA from H-Gln-βNA per minute under the described conditions.

In a second fluorometric assay, isoQC activity was determined using H-Gln-AMC as substrate. Reactions were carried out at 30° C. utilizing the NOVOStar reader for microplates (BMG Labtechnologies). The samples consisted of varying concentrations of the fluorogenic substrate, 0.1 U pyroglutamyl aminopeptidase (Qiagen) in 0.05 M Tris/HCl, pH 8.0 and an appropriately diluted aliquot of isoQC in a final volume of 250 µl. Excitation/emission wavelengths were 380/460 nm. The assay reactions were initiated by addition of glutaminyl cyclase. QC activity was determined from a standard curve of 7-amino-4-methylcoumarin under assay conditions. The kinetic data were evaluated using GraFit sofware.

Spectrophotometric Assay of IsoQC

This assay was used to determine the kinetic parameters for most of the isoQC substrates. isoQC activity was analyzed spectrophotometrically using a continuous method (Schilling, S. et al. 2003 Biol Chem 384, 1583-1592) utilizing glutamic dehydrogenase as auxiliary enzyme. Samples consisted of the respective isoQC substrate, 0.3 mM NADH, 14 mM α-Ketoglutaric acid and 30 U/ml glutamic dehydrogenase in a final volume of 250 µl. Reactions were started by addition of isoQC and pursued by monitoring of the decrease in absorbance at 340 nm for 8-15 min. The initial velocities were evaluated and the enzymatic activity was determined from a standard curve of ammonia under assay conditions. All samples were measured at 30° C., using the Sunrise reader for microplates. Kinetic data were evaluated using GraFit software.

G. Generation of IsoQC-Specific Antibodies and Detection of IsoQCs by Western Blot Analysis The purified recombinant proteins human-isoQC and rat-isoQC protein, together with an adjuvant, were used to immunize rabbits. Following five injections, rabbits were sacrificed and the antibodies purified by lectin affinity chromatography. Two rabbits were immunized using human isoQC (h-isoQC), two further animals received rat isoQC (r-isoQC) injections.

For the detection of native isoQCs, specific polyclonal antibodies against human-isoQC (pAb 3284) and rat-isoQC (pAb 3286), both developed and produced by Probiodrug AG, were obtained. To characterize the specificity of the antibodies, HEK293 cells were transfected with human-isoQC, human QC, rat-isoQC and rat QC. Cells ($2*10^6$) and media were analyzed for QC and isoQC expression. Furthermore, untransfected cells ($3*10^6$) from different mammalian species (HEK293 cells, SH-SY5Y cells, U343 cells, RAW264.7 cells, N2a cells and PC12 cells) were analyzed for basal isoQC expression. For immunoblotting, the cells were disrupted using 200 µl RIPA buffer (Pierce) and sonicated for 10 s. Protein was loaded onto a Tris-Glycine, 4-20% gradient, SDS-PAGE gel (Serva) and separated. Proteins were transferred onto a nitrocellulose membrane (Roth) using semidry conditions. Subsequently, the membrane was blocked for 2 h using 5% (w/v) dry milk in TBS-T [20 mM Tris/HCl (pH 7.5), 500 mM NaCl, 0.05% (v/v) Tween 20]. For the detection of isoQCs the antibodies were diluted 1:1000 in 5% dry milk in TBS-T and incubated over night at 4° C. Blots were developed by applying horseradish peroxidase-conjugated secondary antibodies (anti-rabbit, Cell Signaling) and the SuperSignal West Pico System (Pierce) according to the manufacturer's guidelines.

H. Results (1) Expression and Purification of Mouse-isoQC

Mouse-isoQC was successfully expressed in the methylotrophic yeast *P. pastoris*. The protein starting with glutamate 43 including a glycosylation site at position 56 was expressed in large scale by fermentation in a 5l bioreactor. The purification was carried out as described in Table 10. The purification procedure resulted in an isolation of homogeneous recombinant protein (FIG. 14).

(2) Characterization of Mouse-isoQC

Figure 15:
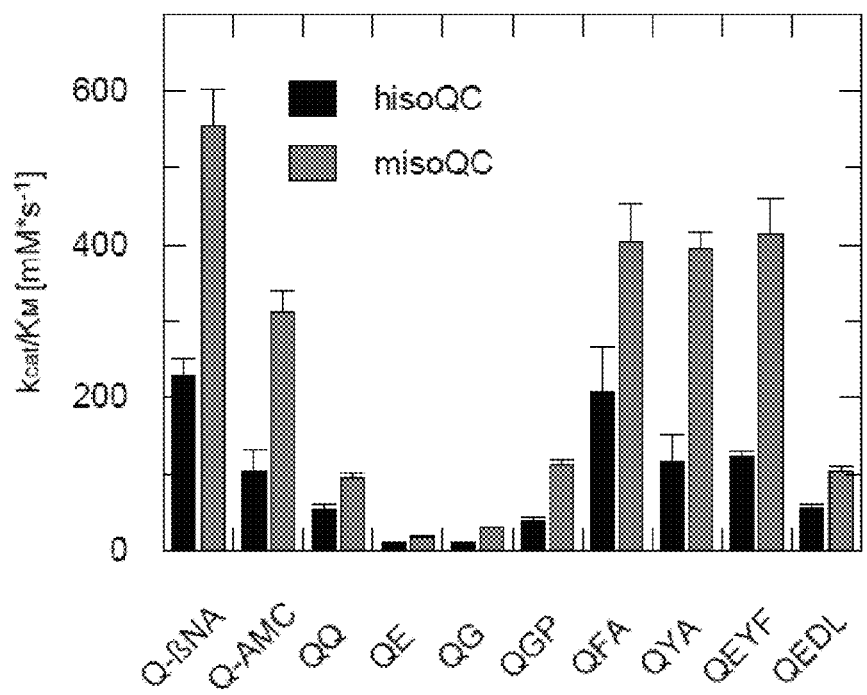
FIG. 15 shows the specificity constants for conversion of dipeptide-surrogates, dipeptides and oligopeptides by mouse-isoQC and human isoQC. The highest specificity was displayed by mouse-isoQC, indicating a higher overall enzymatic activity.

Several different peptide substrates were analyzed (Table 11). All substrates were converted by mouse-isoQC, suggesting a broad substrate specificity similar to human isoQC. As observed previously for human isoQC, highest specificity constants ($k_{cat}/K_M$) were observed for substrates carrying large hydrophobic amino acids adjacent to the N-terminal glutaminyl residue, e.g. Gln-Phe-Ala (QFA). In contrast, negatively charged residues in that position led to a drastic drop in specificity, as observed for Gln-Glu (QE), indicating a negatively charged active site of mouse-isoQC. Compared to human isoQC, mouse-isoQC exerted a two to three times higher enzymatic activity (FIG. 15). The broad specificity supports conversion of many different physiological substrates by all isoQCs described in this invention.

TABLE 11

Kinetic parameters of conversion of peptide substrates by murine and rat isoQC

| Substrate | $K_M$ (mM) m-isoQC | $k_{cat}$ (s$^{-1}$) m-isoQC | $k_{cat}/K_M$ (mM$^{-1}$ * s$^{-1}$) m-isoQC |
|---|---|---|---|
| Q-βNA | 0.032 ± 0.003 | 17.48 ± 0.97 | 554.36 ± 47.02 |
| QAMC | 0.022 ± 0.001 | 6.98 ± 0.35 | 311.31 ± 27.16 |
| QQ | 0.092 ± 0.005 | 8.66 ± 0.37 | 95.08 ± 6.06 |
| QE | 0.47 ± 0.04 | 7.79 ± 0.44 | 16.88 ± 2.32 |
| QG | 0.16 ± 0.01 | 4.57 ± 0.12 | 28.58 ± 1.77 |
| QGP | 0.102 ± 0.006 | 11.4 ± 0.4 | 111.44 ± 6.81 |
| QYA | 0.058 ± 0.004 | 22.88 ± 0.86 | 394.23 ± 21.36 |
| QFA | 0.060 ± 0.006 | 24.1 ± 0.5 | 403.47 ± 48.83 |
| QEYF | 0.029 ± 0.003 | 11.78 ± 0.61 | 413.05 ± 46.04 |
| QEDL | 0.132 ± 0.011 | 13.7 ± 0.8 | 104.33 ± 4.59 |

(3) Western-blot Analysis

Figure 16:
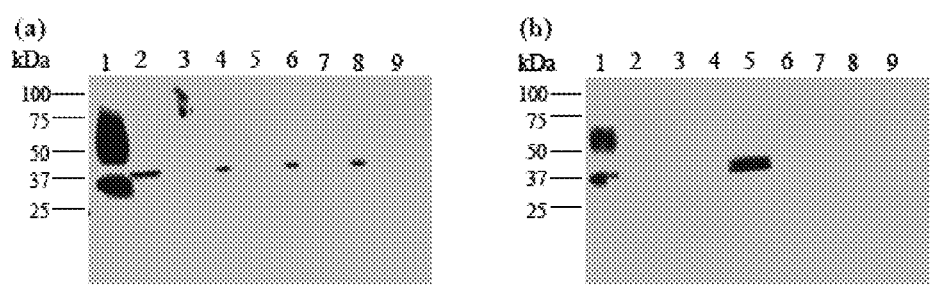
FIG. 16 shows the Western blot analysis for the determination of human isoQC antibody pAb 3284 after transfection of HEK293 cells with different QC and isoQC constructs (per transfected construct, 32 µl disrupted cells and 32 µl 1:10 concentrated media were loaded on a SDS-Gel).

In order to investigate the specificity of the polyclonal isoQC antibodies, (as generated in G. above) HEK293 cells were transfected with human isoQC, rat-isoQC, human QC and rat QC and the expression was analyzed using Western-blot (FIG. 16). By application of human isoQC antibody a band at 37 kDa in the cells transfected with human isoQC, human QC, rat-isoQC and ratQC was detected. The most intense signal was visible in the HEK293 cells which where transfected with human isoQC (FIG. 16a). The isoQCs are enzymes, which are located in the Golgi complex. Accordingly, a signal from the human isoQC transfected cells was expected. The difference in the signal intensity points to a detection of basally expressed human isoQC. After washing the western blot membrane using Restore™ Western Blot Stripping Buffer (Thermo Scientific) and incubation with human QC antibody (pAb 8695) a signal in the media of hQC transfected cells appeared (FIG. 16b). Thus, the generated polyclonal h-isoQC antibody displays no cross-reactivity between isoQC and QC.

In order to analyze, whether the basal expression of human isoQC and mouse and rat-isoQC can be detected applying the novel antibodies, several different, untransfected cell lines were analyzed (FIG. 17). Applying the antibody pAb 3284 (which has been isolated from h-isoQC immunized rabbits) and cell extracts from the human cell lines HEK293, SH-SY5Y and U343, a signal of h-isoQC at 37 kDa was detected. A signal was not detected in the mouse cell lines RAW and N2a as well as in the rat cell line PC12. The Western-blot with rat-isoQC antibody (pAb 3286) visualizes a protein of 37 kDa in the mouse and rat but not in the human cell lines. Therefore, this antibody is able to detect the rat and the mouse isoQC. Accordingly, both antibodies are specific either for human isoQC or rodent (rat and mouse) isoQC. Thus, a detection of basally expressed isoQC is feasible using the polyclonal antibodies as described in G. above in Western-blot analysis. Moreover, the antibodies can be applied for deciphering, which of the two potential start methionines (FIG. 13) is used in different organisms as human and rat. Because of a difference in the molecular mass between the proteins starting at Met I and MetII, the Western-blot analysis as described in this invention can be used to discriminate between the proteins.

The presented data proof an expression of isoQC in all cell lines of investigation. An immunodetection applying the antibodies pAb 3284 and pAb 3286 for isoQC for the first time might be useful for the development of novel analytic procedures for the characterization and detection of certain kinds of inflammation and in particular, neuroinflammation. The method as described is useful for the characterization of QPCT and QPCTL knock-out mice.

Example 9

Thioglycollate-induced Peritonitis in C57/BL6J Wild Type Mice

A. Experimental Procedures

C57/BL6J mice were purchased from Charles River Laboratories (Kisslegg, Germany). For each experiment, the mice were age- and sex-matched. An intraperitoneal injection of 25 ml/kg body weight of sterile 8% (w/v) thioglycollate (Sigma-Aldrich) was used to induce peritonitis. 30 min before the thioglycollate-stimulus, animals were injected with different doses of QC-inhibitor. For lavage of the peritoneum, the animals were anesthetized using 2% isofluran. The peritoneal exudates were collected by washing the peritoneum with 8 ml of sterile PBS 4 h after thioglycollate injection. Cells of 1 ml lavage fluid were collected by centrifugation (300 g, 10 min) and stained according to the manufacturer's instructions for BD Trucount tubes (BD Trucount tubes; catalog no. 340334; BD Biosciences, Heidelberg, Germany). Cells were blocked with CD16/32 (Caltag) at 4° C. for 15 min. and stained with 7/4-FITC (Serotec, Düsseldorf, Germany)/Ly6G-PE (Miltenyi, Bergisch Gladbach, Germany) as well as IgG1-PE (BD)/IgG2a-FITC (Miltenyi) as isotype controls at room temperature for 15 min. After staining, erythrocytes were lysed with BD FACSLyse (BD) in the dark at room temperature for 15 min. After washing with PBS, flow cytometric analysis was performed on a BD FACSCalibur (BD) based on 5000 beads per sample as reference standard.

B. Results

After injection of thioglycollate into the peritoneum of C57/BL6J mice an infiltration of monocytes to this compartment was detected using FACS analysis. The application of the QC/isoQC-specific inhibitor isoQC-I in this model provokes a dose-dependent reduction of the infiltrating monocytes. A reduction could already be observed using 6 mg/kg isoQC-I. 18 mg/kg reduced the infiltration of monocytes down to baseline values, detected when saline alone was injected (FIG. 18a). In analogy, the determination of pGlu-MCP-1 in respective lavage-fluids shows a reduction of pGlu-content, suggesting a treatment effect due to action of the inhibitor at the target enzyme (FIG. 18b).

Accordingly, a similar effect would be expected in the inventive animal model (see example 8 below).

Example 10

Thioglycollate-induced Peritonitis in isoQC (QPCTL) Knock Out Mice

QPCTL knock-out mice were generated on the basis of a genomic mutagenesis approach.

The application of thioglycollate in QPCTL knock out animals does not stimulate monocyte infiltration to the peritoneum. However, in QPCTL wild type littermates an infiltration of monocytes was detected (FIG. 19a), since the activity of isoQC is present there, resulting in proper maturation of MCPs. Granulocyte infiltration was not affected by the isoQC (QPCTL) knock out (FIG. 19b). The impaired infiltration of monocytes correlated with a reduced concentration of pGlu-MCP-1 in QPCTL knock out mice, whereas the total MCP-1 level remained normal (FIG. 20). Therefore, mouse-isoQC knock out has an impact of pGlu-MCP-1 formation and the reduction of pGlu-MCP-1 has an impact on monocyte recruitment to the peritoneum in this animal model. In addition, the genetic proof of principle substantiates the specificity of QC-inhibitor application in the thioglycollate-induced peritonitis. With this experiment it can be proven, that an inhibition of QC results in deactivation of pGlu-MCPs and is therefore a novel treatment strategy for inflammatory diseases.

Example 11

LPS-stimulation of PBMCs Isolated from isoQC (QPCTL) Knock Out Mice

A. Isolation of Plasma and PBMCs

For isolation of peripheral blood mononuclear cells (PBMCs), QPCTL knock out animals and wild type littermates were anesthetized using 2% isofluran and herparinized blood was collected by cardiac puncture. Afterwards, blood was pooled from animals having the same genetic background (isoQC homozygous knock out and wild type animals, respectively) and plasma was collected obtained by centrifugation of the heparinized blood for 10 min at 1000×g. The plasma was divided in aliquots and stored at −80° C. The sedimented blood cells were resuspended in cell culture medium (RPMI1640, 10% FBS, 100 µg/ml Gentamicin).

For isolation of PBMCs, a density gradient was used: 15 ml of LSM 1077 (Lymphocyte Separation Medium, PAA) were filled in a 50 ml Leucosep tube (Greiner). The medium was centrifuged for 1 min at 1000×g. Thereafter, the blood cells were filled into the Leucosep tube (Greiner). The solution was centrifuged for 10 min at 1000×g without activated deceleration to avoid swirling. The liquid covering 1 cm of the upper phase was discarded to avoid a thrombocyte contamination of the sample. Afterward, the medium was completely removed, whereby a circular ring within the Leucosep tube prevented contamination of the PBMC fraction with pelleted erythrocytes. PBMCs were washed 2 times using 10 ml sterile PBS followed by centrifugation. Finally, the cells were resuspended in culture medium (RPMI 1640, 10% FBS, 50 µg/ml Gentamicin), plated in a 25 cm$^2$ tissue culture flask and grown over night at 37° C. and 5% $CO_2$. The next day, PBMCs adhered to the plastic. Therefore, the supernatant containing lymphocytes was removed, cells were washed once with PBS and subsequently dislodged using accutase (PAA). After centrifugation, cells were counted using a Neubauer counting chamber and transferred to a 96-well plate in culture medium (RPMI 1640, 10% FBS, 50 µg/ml Gentamicin). The final cell density was about 1*10$^5$ cells per well. Cells were stimulated using 10 µg/ml LPS from E. coli strain O55:B5 (Sigma) for 24 h. Afterwards, medium was collected and analyzed using total-MCP-1 and pGlu-MCP-1 specific ELISA.

B. Results

Stimulation of PBMCs isolated from QPCTL knock out mice and wild type littermates leads to an increased total MCP-1 concentration in the culture supernatant. Unstimulated PBMCs secrete only low amounts of total MCP-1 (FIG. 21a). The total-MCP-1 level detected in the medium of cells from wild type animals is higher compared to the respective cells from knock out animals. MCP-1 secreted from wild-type-PBMCs possesses a pGlu-modified N-terminus, indicated by the equal amount of total- and pGlu-MCP-1 (FIG. 21a, 21b). In contrast, the cells from QPCTL knock out mice generate only scarce amounts of the N-terminally pGlu-modified MCP-1 as indicated by a low amount of pGlu-MCP-1, detected by ELISA (FIG. 21a) and a low ratio of pGlu-MCP-1 vs. total MCP-1 of approximately 10% compared to >90% in wild type littermates (FIG. 21b).

Example 12

Determination of the Zinc Content of Murine IsoQC

A. TXRF Measurements

After purification of mouse isoQC, the enzyme was desalted by size-exclusion chromatography using a Sephadex G-25 fast desalting column (1.0×10 cm), which was pre-equilibrated in 10 mM Tris-HCl, pH 7.6. The protein was concentrated to 3 mg/ml. Elemental analysis was performed using total reflection X-ray fluorescence (TXRF). The elution buffer was used as a background control. Five microliters of undiluted sample solution or control buffer was applied onto the TXRF quartz glass sample support and dried under IR radiation. Afterwards, 5 µl of diluted Se aqueous standard solution (internal standard, Aldrich; Taufkirchen, Germany) was added to each sample and dried again. The X-ray fluorescence signal was collected for 100 s. For all determinations, an Extra II TXRF module containing molybdenum and tungsten primary X-ray sources (Seifert, Ahrensburg, Germany) connected to a Link QX 2000 detector/analysis device (Oxford Instruments, High Wycombe, UK) was used. The X-ray sources were operated at 50 kV and 38 mA.

B. Inactivation/Reactivation

Mouse isoQC and mouse QC were inactivated by dialysis against 1.0 l of buffer containing 5 mM 1,10-phenantroline, 5 mM EDTA, 500 mM NaCl in 50 mM BisTris pH 6.8 over night at 4° C. The chelating agents were separated from the apoenzymes by dialysis against 1 l of 50 mM BisTris, pH 6.8, 500 mM NaCl, containing 50 g/l Chelex-100 (Bio-RAD, Munich), or 10 mM $NaH_2PO_4$, pH 6.8 containing 50 g/l Chelex-100 at 4° C. The buffer was changed 2 times, after 2 and 4 h of dialysis. The final dialysis was performed for 5 h. All buffers were prepared in metal-free polystyrene containers. Subsequently, the apoenzyme was centrifuged at 20.000×g for 1 h at 4° C., and the protein concentration was determined by UV absorbance.

The reactivation experiments were carried out by incubation of 20 µl of a transition metal solution with 20 µl of apoenzyme in Bis-Tris buffer at room temperature for 15 min. Finally, enzymatic activity was assessed as described above, except the reaction buffer contained 2 mM EDTA in order to avoid rapid reactivation of the enzymes by adventitious zinc ions present in the buffers.

C. CD-spectroscopic Analysis

For the spectroscopic analysis the proteins were prepared in 10 mM $NaH_2PO_4$. CD-spectra of mouse QC and mouse isoQC were acquired with a Jasco J-715 spectrapolarimeter using quartz cuvettes of 1 mm pathlength. The mean of 10 scans between 190 and 260 nm was calculated and the spectra were corrected by subtraction of the buffer spectra. The percentage of secondary structure elements was calculated using the Jasco secondary structure estimation program based on the method of Yang. The apoenzymes and reactivation of the enzymes was confirmed by QC activity measurements after spectra analysis.

D. Results

For the mouse QC, a metal content of 1 mol zinc/mol of enzyme was determined, previously. The zinc binding motif of QC is also conserved in the sequence of the isoQCs. Therefore, the metal content of mouse isoQC was analyzed, using TXRF. The measurements of three independent enzyme samples determined a zinc content of 0.99±0.38 mol of zinc/mol of enzyme. Thus, the isoQC proteins represent single zinc metalloenzymes as shown here for the first time.

For human isoQC it was shown that the protein can be inactivated by heterocyclic chelators like 1,10-phenantroline, dipicolinic acid and EDTA. Dialysis against buffer containing 5 mM 1,10-phenantrolin and 5 mM EDTA resulted in inactivation of mouse-isoQC. After removal of the chelator, addition of $ZnSO_4$ resulted in complete reactivation of mouse-isoQC. To verify the results, different amounts of zinc were titrated to the apoenzymes (mouse isoQC, mouse QC and *Drosophila melanogaster* (Drome) QC) (FIG. 22*a*). All tested enzymes are 100% reactivated by adding 1 mol of zinc/mol of enzyme as well as with 2 mol of zinc/mol of enzyme. With a ratio of 0.5 zinc/mol of enzyme an activity of at least 60% was reached.

Furthermore, a reactivation of mouse-isoQC by other metal ions was examined. By addition of 1 mol of cobalt/mol of enzyme, a reactivation was achieved. However, the final activity was only 50% compared to the reactivation with zinc ions. No reactivation was achieved using calcium or manganese ions (FIG. 22*b*).

To investigate the influence of zinc binding on the protein structure, the secondary structure of the apoenzyme and of the reactivated mouse-isoQC was evaluated via CD spectra from 190-260 nm. In both cases the calculation of the secondary structure revealed an α helical portion of 50%. Thus, zinc binding has no influence on the overall secondary structure. This supports that the metal ion primarily plays a catalytic role, (FIG. 23).

According to these results, mutation of the residue responsible for complexation of the catalytic active zinc ion, i.e. residues Asp187, Glu227 or His352, is a strategy to generate a mouse or rat QPCTL knock-out model.

Example 13

TransWell Chemotaxis Assay

Human acute monocytic leukaemia cell line THP-1 was cultured in RPMI1640, 10% FBS, in a humidified atmosphere of 5% $CO_2$ at 37° C. The chemotactic assay was performed using 24-well TransWell plates with a pore size of 5 µm (Corning). 600 µl of chemoattractant solution were applied to the lower chamber. Serum-free RPMI was applied as negative control. THP-1 cells were harvested and resuspended in RPMI1640 in a concentration of $1*10^6$ cells/100 µl and applied in 100 µl aliquots to the upper chamber. Cells were allowed to migrate towards the chemoattractant for 2 h at 37° C. Subsequently, cells from the upper chamber were discarded and the lower chamber was mixed with 50 µl 70 mM EDTA in PBS and incubated for 15 min at 37° C. to release cells attached to the membrane. Afterwards, migrated cells were counted using a cell counter system (Schärfe System, Reutlingen). The chemotactic index was calculated by dividing cells migrated to the stimulus from cells migrated to the negative control.

Example 14

Determination of QC-activity in Brain Tissue

Aim

The Goal of the analysis was to characterize the QC enzymatic activity in wild type mice (isoQC$^{+/+}$) and isoQC knock-out (isoQC$^{-/-}$) mice, both having the same genetic background.

Methods

QC activity was determined using a discontinuous assay based on separation and quantification of the substrate Gln-βNA and the product pGlu-βNA using HPLC-UV. Briefly, test samples from brain or peripheral tissue were homogenized in a buffer consisting of 10 mM Tris, 100 mM NaCl, 5 mM EDTA, 0.5% Triton X-100 and 10% Glycerol, pH 7.5, using a Precellys homogenizer (Peqlab). The homogenate was further sonicated and centrifuged at 16.000×g for 30 min and 4° C. The protein concentration of the resulting supernatant containing QC and isoQC was adjusted to 5-7 mg/ml. Reaction samples consisted of 50 µM H-Gln-βNA in 25 mM MOPS, pH 7.0, 0.1 mM N-ethylmaleinimide (NEM) and enzyme solution in a final volume of 1 ml. The reaction temperature was 37° C. Test samples were removed for up to one hour, and the reaction stopped by boiling for 5 min followed by centrifugation at 16.000×g for 10 min. The supernatant was applied to HPLC analyses using a RP18 LiChroCART HPLC Cartridge and the HPLC system D-7000 (Merck-Hitachi). The samples (20 µl) were injected and separated by increasing concentration of solvent A (acetonitrile containing 0.1% TFA) from 8% to 20% in solvent B (H2O containing 0.1% TFA). QC activity was quantified from a standard curve of pGlu-βNA (Bachem) determined under assay conditions.

The assay does not descriminate between isoQC or QC, only total levels of activity can be determined.

Results

The analysis shows a differential influence of the isoQC depletion in isoQC knock-out (isoQC$^{-/-}$) mice. In all tested tissues, a tendency to decreased activity was observed due to the knock-out of isoQC. The difference was more significant in brain regions with relatively low overall activity, e.g. cortex or cerebellum (FIG. 35). Negligible differences were observed in tissues with high activity, e.g. hypothalamus. The results show, that isoQC is expressed throughout the brain, apparently at similar levels. The results are supported by data from QC knock-out mice, which showed a high drop in activity in hypothalamus, hippocampus and brainstem, in contrast to the isoQC knock-out mice analyzed here. The data support the house-keeping character of isoQC expression and the high expression of its sisietr enzyme QC in brain tissue with high levels of neuropeptide hormone processing like hypothalamus.

ABBREVIATIONS

° C. degree Celsius
A alanine, ala
Aβ amyloid-β peptide
ABri amyloid peptide in familial British dementia
ADan amyloid peptide in familial Danish dementia
AMC amino methyl coumarine
as antisense
Asp aspartate
Asn asparagine
βNA beta-naphtylamine
bp base pair
BSA bovine serum albumin
BMMY buffered Methanol complex medium
BMGY buffered glycerol comlex medium
C cysteine, Cys
CCL2 MCP-1, monocyte chemoattractant protein 1
CCL7 MCP-3, monocyte chemoattractant protein 3
CCL8 MCP-2, monocyte chemoattractant protein 2
CCL13 MCP-4, monocyte chemoattractant protein 4
cDNA copy-DNA
C-His C-terminal histidine tag
Cl chlorine
Cm centimeter
C-terminus carboxy-terminus
CV column volume
Cys cysteine, cys
d diameter
D aspartic acid, Asp
Da Dalton
DMSO dimethyl sulphoxide
DNA desoxyribonucleic acid
E Glutamic acid, Glu
*E. coli* Escherichia coli
EC glutamyl cyclase
EGFP enhanced green fluorescent protein
ES enzyme-substrate complex
F Phenylalanine, Phe
g relative centrifugal force
G Glycine, Gly
GF gel filtration
Gln glutamine
Glu glutamic acid
GnRH gonadotropin-releasing hormone (gonadoliberin)
GST glutathion S-transferase
H hydrogen
h human or hour
HET heterozygous
HIC hydrophobic interaction chromatography
HIC-EBA hydrophobic interaction chromatography, expanded bed absorption
His histidine
HOM homozygous
HPLC high performance liquid chromatography
I inhibitor or isoleucine
ID identification
IEX ion exchange chromatography
Ile Isoleucine
ip intraperitoneal
K potassium
k constant
kDa kilo-dalton
Ki inhibition constant (for inhibitor binding)
k.o. knock-out
l length
L Leucine, Leu
LB Luria-Bertani
LPS lipopolysaccharide
m mouse, murine
M molar
μl micro-liter
μM micro-molar
Maldi-tof matrix assisted laser desorption/ionization time-of-flight
max maximum
MES 2-(N-morpholino)ethanesulfonic acid
Met methionine
min minutes
mM milli-molar
MS Multiple Sclerosis
mRNA messenger-RNA
N asparagine
Na sodium
NADH nicotinamide adenine dinucleotide
nm nanometer
NO number
NT Neurotensin
N-terminus amino terminus
O oxygen
OD optical density
P product or phosphor or proline, Pro
PBS phosphate-buffered saline
PCR polymerase chain reaction
pGlu pyroglutamic acid
pH pondus hydrogenii
Pro proline
Pyr pyroglutamate
Q Glutamine, Gln
QC glutaminyl cyclase (glutaminyl-peptide cyclotransferase)
QQ Dipeptide Gln-Gln
QE Dipeptide Gln-Glu
QG Dipeptide Gln-Gly
QGP Tripeptide Gln-Gly-Pro
QYA Tripeptide Gln-Tyr-Ala
QFA Tripeptide Gln-Phe-Ala
QEYF Tetrapeptide Gln-Glu-Tyr-Phe
QEDL Tetrapeptide Gln-Glu-Asp-Leu
qPCR quantitative real-time polymerase chain reaction
QPCTL glutaminyl-peptide cyclotransferase-like
RNA ribonucleic acid
RT reverse transcription; reverse transcriptase
S substrate
s sense
SDS sodium dodecyl sulfate
SDS-PAGE SDS-polyacrylamid gel electrophoresis
SEC size exclusion chromatography
SEQ sequence
Ser Serine
TRH thyreotropin-realeasing hormone (thyreoliberin)
Tris Tris(hydroxymethyl)-aminomethane,
U unit
UV ultraviolet
V velocity
WT wildtype
Y Tyrosine, Tyr
YPD Yeast extract, Peptone, Dextrose-medium
YPDS Yeast extract, Peptone, Dextrose-medium containing sorbitol
YSS yeast signal sequence
Zn zinc

What is claimed is:

1. A mouse or rat comprising cells containing a DNA QPCTL gene carrying a knock-out mutation, wherein
   (A) the mouse or rat carries at least one QPCTL allele where the QPCTL gene carries a Thymidine to Adenosine (T→A) nucleotide substitution at nucleotide position 442 of SEQ ID NO. 1, leading to the introduction of a stop codon into the QPCTL open reading frame; or
   (B) the QPCTL gene carries at least one mutation, results in the mutation of at least one amino residue that is responsible for complexation of the catalytic active zinc ion; and wherein the mutation in the QPCTL gene comprising SEQ ID NO: 2 or SEQ ID NO: 5 results in the mutation of at least one amino acid residue selected from the group consisting of Asp187, Glu227, and His352.

2. The mouse or rat of claim 1, wherein the mouse or rat is heterozygous for the knock-out mutation in the QPCTL gene.

3. The mouse or rat of claim 1, wherein the mouse or rat is homozygous for the knock-out mutation in the QPCTL gene.

4. The mouse or rat of claim 1, wherein the mouse or rat is a mouse.

5. The mouse or rat of claim 1, wherein the mouse or rat is a rat.

6. The mouse or rat of claim 1, wherein the QPCTL gene carries a constitutive knock-out mutation.

7. The mouse or rat of claim 1, wherein the mouse or rat carries at least one QPCTL allele where the QPCTL gene carries a Thymidine to Adenosine (T→A) nucleotide substitution at nucleotide position 442 of SEQ ID NO. 1, leading to the introduction of a stop codon into the QPCTL open reading frame.

8. The mouse or rat of claim 7, wherein the mouse or rat is a mouse of the mouse line QPCTL_L144X.

9. The mouse or rat of claim 1,
   wherein the QPCTL gene carries at least one mutation, which results in the mutation of at least one amino residue that is responsible for complexation of the catalytic active zinc ion; and
   wherein the mutation in the QPCTL gene comprising SEQ ID NO: 2 or SEQ ID NO: 5 results in the mutation of at least one amino acid residue selected from the group consisting of Asp187, Glu227, and His352.

10. The mouse or rat of claim 1, wherein the mouse or rat demonstrates a phenotype that can be reversed or ameliorated with a QPCTL inhibitor.

11. The mouse or rat of claim 1, wherein the QPCTL gene is operably linked to a tissue-specific promoter.

12. The mouse or rat of claim 1, further comprising an exogenous test compound.

13. A cell or cell line containing a DNA QPCTL gene carrying a knock-out mutation, wherein said cell or cell line is derived from the mouse or rat according to claim 1.

14. A mouse or rat comprising cells containing a QPCTL gene comprising SEQ ID NO: 1, SEQ ID NO: 4, or SEQ ID NO: 6 having at least one knock-out mutation.

15. The mouse or rat of claim 14, wherein the cells contain a QPCTL gene comprising SEQ ID NO: 1 or SEQ ID NO: 4 having at least one knock-out mutation.

16. The mouse or rat of claim 14, wherein the QPCTL gene encodes a QPCTL polypeptide of SEQ ID NO: 2, SEQ ID NO: 5, or SEQ ID NO: 7, and the at least one knock-out mutation reduces QPCTL polypeptide activity in the mouse or rat.

17. The mouse or rat of claim 14, wherein the QPCTL gene encodes a QPCTL polypeptide of SEQ ID NO: 2 or SEQ ID NO: 5, and the at least one knock-out mutation reduces QPCTL polypeptide activity in the mouse or rat.

18. A mouse or rat comprising cells containing a QPCTL gene encoding a polypeptide of SEQ ID NO: 2, SEQ ID NO: 5, or SEQ ID NO: 7, the QPCTL gene having at least one knock-out mutation.

19. The mouse or rat of claim 18, wherein the cells contain a QPCTL gene encoding a polypeptide of SEQ ID NO: 2 or SEQ ID NO: 5, the QPCTL gene having at least one knock-out mutation.

* * * * *

SEQUENCE LISTING

<160> NUMBER OF SEQ ID NOS: 40

<210> SEQ ID NO 1
<211> LENGTH: 2100
<212> TYPE: DNA
<213> ORGANISM: Mus musculus

<400> SEQUENCE: 1

| | | | | | |
|---|---|---|---|---|---|
| gcaaagctac | catgagtccc | gggagccgcg | ggcggcccg | gcagcggctc | gaggatcgtg | 60 |
| gcctcatgaa | accaccctca | ctttccaagc | gccgtcttct | gccgcgagtg | cagttcctgc | 120 |
| ccctgctgct | gctggcgctg | gctatgggct | tggctttcta | tatcgtctgg | aacagctggc | 180 |
| accctgggt | tgaggagatg | tcacggagcc | gggatctgcg | ggtcccgctg | atcggaagcc | 240 |
| tttcagaagc | caagctgcgg | ctggtggtag | ggcagctgga | tccgcagcgt | ctctgggaa | 300 |
| ctttcctgcg | tcccttattg | attgtgcgac | ccccgggtag | ttctggcaat | ctccaagtga | 360 |
| gaaagttcct | ggaggctacg | ttgcagtccc | tgtcggcagg | ctggcatgtt | gaactggacc | 420 |
| cattcacggc | ctcaaccccc | ttggggccac | tggacttcgg | gaacgtggtg | gccacacttg | 480 |
| acccaggagc | tgcccgtcac | ctcaccctcg | cctgccatta | tgactctaag | ttcttccctc | 540 |
| cggggttgcc | ccccttttgtg | ggggccacag | attcagctgt | gccctgtgcc | ctgcttctgg | 600 |
| agttggtcca | ggcccttgat | gccatgctga | gcagaatcaa | gcagcaggca | gcaccggtga | 660 |
| ccctgcagct | gcttttcttg | gatggggagg | aggcactgaa | ggagtgggga | ccaaaggact | 720 |
| ccctctatgg | ctcccggcac | ctagctcaga | tcatggagtc | tataccacac | agccctggcc | 780 |
| ccaccaggat | ccaggctatt | gagctctttg | tcctcctcga | ccttctggga | gcatccagtc | 840 |
| cgatcttctt | cagtcacttc | cctcgcacag | cccgctggtt | ccagcgactg | aggagcattg | 900 |
| agaagcgcct | tcaccggctg | aacctactgc | agtctcaccc | ccaggaagtg | atgtacttcc | 960 |
| aacccgggga | gccccccggc | cctgtggaag | atgaccacat | ccccttcctt | cgcagagggg | 1020 |
| tcccggtgct | ccacctcatt | gccacgccct | tccctgctgt | gtggcacaca | cctgctgaca | 1080 |
| ccgaggccaa | cctccaccca | cccactgtgc | ataacctgag | ccgcatcctt | gctgtgttcc | 1140 |
| tggccgagta | cctgggactc | tagcctgcag | cctgatacct | tgaaggaatc | ttatacactt | 1200 |
| agctgtggac | tggacagggg | caccttgagc | cagtgcaggg | tggccagtct | cacctcagat | 1260 |
| gtatgctaca | accatgtgaa | gtcaccgtgt | ttcaaggatg | caaggaacac | tgaggcacga | 1320 |
| aagagccaaa | ggaaataagg | aatcctttgg | cttctgtcct | gaagtaaata | actggaaggt | 1380 |
| tccagggacc | aaatgatgtg | tcacgggctg | gcacgtggac | cagcaccacc | aaccaaatga | 1440 |
| atccattgcg | gctaatgttt | gatgtcagtt | catttgctac | cgtactccac | atgggcatgg | 1500 |
| gctcataact | taggacagag | acgaagccta | gttcgatggt | ctacggtctg | cttggctcag | 1560 |
| gggtgccaac | ctcgagggta | aaggggaacg | gaaggccaca | gcgctcatga | aaagtgtcac | 1620 |
| taaatgaact | tcctcactgc | aaaggtgaga | tcttccagag | taagaggatg | aaatggttct | 1680 |
| caaagtactc | cacagtggga | cctctttgca | ggaaggtatt | tcaagtgaag | ctgcctccag | 1740 |
| gattctttgg | gaaatactgc | cttttggcagg | ttgagagtgg | gaatggactg | aatagacaga | 1800 |
| ggtccacctg | gatggagtta | acccgaacct | acccttttcct | tttgttgtgt | gtgcaactct | 1860 |
| agtcaagttt | ctttttttctt | gagactttgt | ttctctgtgt | agccctgcct | gatttgaaac | 1920 |
| tcaatctata | gaccagctgg | cctcaaattt | agagattcac | cttcctctac | ctccagactt | 1980 |
| gctgggatta | aaggcgtgtg | ccccactgc | ctggctggcc | tggaactttc | tatgtagatc | 2040 |
| ttgaacacaa | gagccgtgac | tccaccgtca | ctggaattga | aaggaaaagc | caccacaccc | 2100 |

<210> SEQ ID NO 2
<211> LENGTH: 383
<212> TYPE: PRT
<213> ORGANISM: Mus musculus

<400> SEQUENCE: 2

```
Met Ser Pro Gly Ser Arg Gly Arg Pro Arg Gln Arg Leu Glu Asp Arg
1               5                   10                  15

Gly Leu Met Lys Pro Pro Ser Leu Ser Lys Arg Arg Leu Leu Pro Arg
            20                  25                  30

Val Gln Phe Leu Pro Leu Leu Leu Ala Leu Ala Met Gly Leu Ala
        35                  40                  45

Phe Tyr Ile Val Trp Asn Ser Trp His Pro Gly Val Glu Glu Met Ser
    50                  55                  60

Arg Ser Arg Asp Leu Arg Val Pro Leu Ile Gly Ser Leu Ser Glu Ala
65                  70                  75                  80

Lys Leu Arg Leu Val Val Gly Gln Leu Asp Pro Gln Arg Leu Trp Gly
                85                  90                  95

Thr Phe Leu Arg Pro Leu Leu Ile Val Arg Pro Pro Gly Ser Ser Gly
            100                 105                 110

Asn Leu Gln Val Arg Lys Phe Leu Glu Ala Thr Leu Gln Ser Leu Ser
        115                 120                 125

Ala Gly Trp His Val Glu Leu Asp Pro Phe Thr Ala Ser Thr Pro Leu
    130                 135                 140

Gly Pro Leu Asp Phe Gly Asn Val Val Ala Thr Leu Asp Pro Gly Ala
145                 150                 155                 160

Ala Arg His Leu Thr Leu Ala Cys His Tyr Asp Ser Lys Phe Phe Pro
                165                 170                 175

Pro Gly Leu Pro Pro Phe Val Gly Ala Thr Asp Ser Ala Val Pro Cys
            180                 185                 190

Ala Leu Leu Leu Glu Leu Val Gln Ala Leu Asp Ala Met Leu Ser Arg
        195                 200                 205

Ile Lys Gln Gln Ala Ala Pro Val Thr Leu Gln Leu Leu Phe Leu Asp
    210                 215                 220

Gly Glu Glu Ala Leu Lys Glu Trp Gly Pro Lys Asp Ser Leu Tyr Gly
225                 230                 235                 240

Ser Arg His Leu Ala Gln Ile Met Glu Ser Ile Pro His Ser Pro Gly
                245                 250                 255

Pro Thr Arg Ile Gln Ala Ile Glu Leu Phe Val Leu Asp Leu Leu
            260                 265                 270

Gly Ala Ser Ser Pro Ile Phe Phe Ser His Phe Pro Arg Thr Ala Arg
        275                 280                 285

Trp Phe Gln Arg Leu Arg Ser Ile Glu Lys Arg Leu His Arg Leu Asn
    290                 295                 300

Leu Leu Gln Ser His Pro Gln Glu Val Met Tyr Phe Gln Pro Gly Glu
305                 310                 315                 320

Pro Pro Gly Pro Val Glu Asp Asp His Ile Pro Phe Leu Arg Arg Gly
                325                 330                 335

Val Pro Val Leu His Leu Ile Ala Thr Pro Phe Pro Ala Val Trp His
            340                 345                 350

Thr Pro Ala Asp Thr Glu Ala Asn Leu His Pro Pro Thr Val His Asn
        355                 360                 365

Leu Ser Arg Ile Leu Ala Val Phe Leu Ala Glu Tyr Leu Gly Leu
```

```
                  370                 375                 380

<210> SEQ ID NO 3
<211> LENGTH: 382
<212> TYPE: PRT
<213> ORGANISM: Mus musculus

<400> SEQUENCE: 3

Met Ser Pro Gly Ser Arg Gly Arg Pro Arg Gln Arg Leu Glu Asp Arg
1               5                   10                  15

Gly Leu Met Lys Pro Pro Ser Leu Ser Lys Arg Arg Leu Leu Pro Arg
            20                  25                  30

Val Gln Phe Leu Pro Leu Leu Leu Ala Leu Ala Met Gly Leu Ala
        35                  40                  45

Phe Tyr Ile Val Trp Asn Ser Trp His Pro Val Glu Glu Met Ser
    50                  55                  60

Arg Ser Arg Asp Leu Arg Val Pro Leu Ile Gly Ser Leu Ser Glu Ala
65                  70                  75                  80

Lys Leu Arg Leu Val Val Gly Gln Leu Asp Pro Gln Arg Leu Trp Gly
                85                  90                  95

Thr Phe Leu Arg Pro Leu Leu Ile Val Arg Pro Gly Ser Ser Gly
                100                 105                 110

Asn Leu Gln Val Arg Lys Phe Leu Glu Ala Thr Leu Gln Ser Leu Ser
            115                 120                 125

Ala Gly Trp His Val Glu Leu Asp Pro Phe Thr Ala Ser Thr Pro Leu
        130                 135                 140

Gly Pro Leu Asp Phe Gly Asn Val Val Ala Thr Leu Asp Pro Gly Ala
145                 150                 155                 160

Ala Arg His Leu Thr Leu Ala Cys His Tyr Asp Ser Lys Phe Phe Pro
                165                 170                 175

Pro Gly Leu Pro Pro Phe Val Gly Ala Thr Asp Ser Ala Val Pro Cys
            180                 185                 190

Ala Leu Leu Leu Glu Leu Val Gln Ala Leu Asp Ala Met Leu Ser Arg
        195                 200                 205

Ile Lys Gln Gln Ala Ala Pro Val Thr Leu Gln Leu Leu Phe Leu Gly
    210                 215                 220

Glu Glu Ala Leu Lys Glu Trp Gly Pro Lys Asp Ser Leu Tyr Gly Ser
225                 230                 235                 240

Arg His Leu Ala Gln Ile Met Glu Ser Ile Pro His Ser Pro Gly Pro
                245                 250                 255

Thr Arg Ile Gln Ala Ile Glu Leu Phe Val Leu Leu Asp Leu Leu Gly
            260                 265                 270

Ala Ser Ser Pro Ile Phe Phe Ser His Phe Pro Arg Thr Ala Arg Trp
        275                 280                 285

Phe Gln Arg Leu Arg Ser Ile Glu Lys Arg Leu His Arg Leu Asn Leu
    290                 295                 300

Leu Gln Ser His Pro Gln Glu Val Met Tyr Phe Gln Pro Gly Glu Pro
305                 310                 315                 320

Pro Gly Pro Val Glu Asp Asp His Ile Pro Phe Leu Arg Arg Gly Val
                325                 330                 335

Pro Val Leu His Leu Ile Ala Thr Pro Phe Pro Ala Val Trp His Thr
            340                 345                 350

Pro Ala Asp Thr Glu Ala Asn Leu His Pro Pro Thr Val His Asn Leu
        355                 360                 365
```

Ser Arg Ile Leu Ala Val Phe Leu Ala Glu Tyr Leu Gly Leu
    370                 375                 380

<210> SEQ ID NO 4
<211> LENGTH: 1152
<212> TYPE: DNA
<213> ORGANISM: Rattus norvegicus

<400> SEQUENCE: 4

| | | |
|---|---|---|
| atgagtccgg ccagccgcgg gcggtctcgg cagcggctcg gggatcgcgg cctcatgaaa | 60 |
| ccaccctcac tttccaagcg ccgtcttctg ccgcgggtgc agctcctgcc cctgctgctg | 120 |
| ctggcgctgg ccctgggctt ggcttttat atcgtctgga atagctggca ccctggggtt | 180 |
| gaggaggtat cacggagccg ggatctgcgg gtcccgctga tcggaagcct ttcagaagcc | 240 |
| aagctgcggc ttgtggtagg gcagctggat ccacagcgtc tctggggaac ttttctgcgt | 300 |
| cccttgttga ttgtacgacc cccaggtagt cctggcaatc tccaagtgag aaagttcctg | 360 |
| gaggctacgt tgcagtccct atcggcaggc tggcacgtgg aactggaccc attcacagcc | 420 |
| tcaaccccct tggggccact ggacttcggg aacgtggtgg ccaccttga cccaggagct | 480 |
| gcccgtcacc tcaccctcgc ctgccattat gactctaagt tcttccctcc tgggttaccc | 540 |
| cccttgtgg gggccacaga ttcagccgtg ccctgtgccc tgcttctgga gttagtccag | 600 |
| gcccttgatg tcatgctgag cagaatcaag cagcaggcag caccagtgac cctgcagctg | 660 |
| ctcttcttgg acggggagga ggcactgaag gagtggggac caaaggactc cctctatggt | 720 |
| tcccggcacc tagctcagat catggagtct ataccgcaca gccctggccc caccaggatc | 780 |
| caggctattg agctctttgt ccttcttgac cttctgggag cgcccagtcc aatcttcttc | 840 |
| agtcacttcc cccgcacagc ccgctggttc aacgactgc ggagcatcga aagcgccttt | 900 |
| caccgtctga acctactgca gtctcacccc caggaagtga tgtacttcca acccggggag | 960 |
| ccccctggcc ctgtggaaga tgaccacatc cccttccttc gcagagggt cccgtgctc | 1020 |
| cacctcattg cgatgccctt ccctgccgtg tggcacacac ctgctgacac tgaggctaac | 1080 |
| ctccacccgc ccacggtgca caacctgagc cgcatcctcg ccgtgttcct ggctgagtac | 1140 |
| ctgggtctct ag | 1152 |

<210> SEQ ID NO 5
<211> LENGTH: 383
<212> TYPE: PRT
<213> ORGANISM: Rattus norvegicus

<400> SEQUENCE: 5

Met Ser Pro Ala Ser Arg Gly Arg Ser Arg Gln Arg Leu Gly Asp Arg
1               5                   10                  15

Gly Leu Met Lys Pro Pro Ser Leu Ser Lys Arg Arg Leu Leu Pro Arg
            20                  25                  30

Val Gln Leu Leu Pro Leu Leu Leu Ala Leu Ala Leu Gly Leu Ala
        35                  40                  45

Phe Tyr Ile Val Trp Asn Ser Trp His Pro Gly Val Glu Glu Val Ser
    50                  55                  60

Arg Ser Arg Asp Leu Arg Val Pro Leu Ile Gly Ser Leu Ser Glu Ala
65                  70                  75                  80

Lys Leu Arg Leu Val Val Gly Gln Leu Asp Pro Gln Arg Leu Trp Gly
                85                  90                  95

Thr Phe Leu Arg Pro Leu Leu Ile Val Arg Pro Pro Gly Ser Pro Gly
            100                 105                 110

```
Asn Leu Gln Val Arg Lys Phe Leu Glu Ala Thr Leu Gln Ser Leu Ser
            115                 120                 125
Ala Gly Trp His Val Glu Leu Asp Pro Phe Thr Ala Ser Thr Pro Leu
        130                 135                 140
Gly Pro Leu Asp Phe Gly Asn Val Val Ala Thr Leu Asp Pro Gly Ala
145                 150                 155                 160
Ala Arg His Leu Thr Leu Ala Cys His Tyr Asp Ser Lys Phe Phe Pro
                165                 170                 175
Pro Gly Leu Pro Pro Phe Val Gly Ala Thr Asp Ser Ala Val Pro Cys
            180                 185                 190
Ala Leu Leu Leu Glu Leu Val Gln Ala Leu Asp Val Met Leu Ser Arg
        195                 200                 205
Ile Lys Gln Gln Ala Ala Pro Val Thr Leu Gln Leu Leu Phe Leu Asp
    210                 215                 220
Gly Glu Glu Ala Leu Lys Glu Trp Gly Pro Lys Asp Ser Leu Tyr Gly
225                 230                 235                 240
Ser Arg His Leu Ala Gln Ile Met Glu Ser Ile Pro His Ser Pro Gly
                245                 250                 255
Pro Thr Arg Ile Gln Ala Ile Glu Leu Phe Val Leu Leu Asp Leu Leu
            260                 265                 270
Gly Ala Pro Ser Pro Ile Phe Phe Ser His Phe Pro Arg Thr Ala Arg
        275                 280                 285
Trp Phe Gln Arg Leu Arg Ser Ile Glu Lys Arg Leu His Arg Leu Asn
    290                 295                 300
Leu Leu Gln Ser His Pro Gln Glu Val Met Tyr Phe Gln Pro Gly Glu
305                 310                 315                 320
Pro Pro Gly Pro Val Glu Asp Asp His Ile Pro Phe Leu Arg Arg Gly
                325                 330                 335
Val Pro Val Leu His Leu Ile Ala Met Pro Phe Pro Ala Val Trp His
            340                 345                 350
Thr Pro Ala Asp Thr Glu Ala Asn Leu His Pro Pro Thr Val His Asn
        355                 360                 365
Leu Ser Arg Ile Leu Ala Val Phe Leu Ala Glu Tyr Leu Gly Leu
    370                 375                 380

<210> SEQ ID NO 6
<211> LENGTH: 1149
<212> TYPE: DNA
<213> ORGANISM: Homo sapiens

<400> SEQUENCE: 6
atgcgttccg gggccgcgg gcgaccccgc ctgcggctgg gggaacgtgg cctcatggag      60
ccactcttgc cgccgaagcg ccgcctgcta ccgcgggttc ggctcttgcc tctgttgctg     120
gcgctggccg tgggctcggc gttctacacc atttggagcg ctggcaccg caggactgag     180 gagctgccgc tgggccggga gctgcgggtc ccattgatcg gaagcctccc cgaagcccgg     240
ctgcggaggg tggtgggaca actggatcca cagcgtctct ggagcactta tctgcgcccc     300
ctgctggttg tgcgaacccc gggcagcccg ggaaatctcc aagtcagaaa gttcctggag     360
gccacgctgc ggtccctgac agcaggttgg cacgtggagc tggatccctt cacagcctca     420
acacccctgg ggccagtgga ctttggcaat gtggtggcca cactggaccc aagggctgcc     480
cgtcacctca cccttgcctg ccattatgac tcgaagctct cccaccccgg atcgaccccc     540
tttgtagggg ccacggattc ggctgtgccc tgtgccctgc tgctggagct ggcccaagca     600
```

```
cttgacctgg agctgagcag ggccaaaaaa caggcagccc cggtgaccct gcaactgctc    660
ttcttggatg gtgaagaggc gctgaaggag tggggaccca aggactccct ttacggttcc    720
cggcacctgg cccagctcat ggagtctata cctcacagcc ccggcccac caggatccag    780 gctattgagc tctttatgct tcttgatctc ctgggagccc caatcccac cttctacagc    840 cacttccctc gcacggtccg ctggttccat cggctgagga gcattgagaa cgtctgcac    900 cgtttgaacc tgctgcagtc tcatcccag gaagtgatgt acttccaacc cggggagccc    960
tctggctctg tggaagacga ccacatcccc ttcctccgca gaggggtacc cgtgctccat   1020
ctcatctcca cgcccttccc tgctgtctgg cacaccctg cggacaccga ggtcaatctc   1080
cacccaccca cggtacacaa cttgtgccgc attctcgctg tgttcctggc tgaatacctg   1140
gggctctag                                                            1149

<210> SEQ ID NO 7
<211> LENGTH: 382
<212> TYPE: PRT
<213> ORGANISM: Homo sapiens

<400> SEQUENCE: 7

Met Arg Ser Gly Gly Arg Gly Arg Pro Arg Leu Arg Leu Gly Glu Arg
1               5                   10                  15

Gly Leu Met Glu Pro Leu Leu Pro Lys Arg Arg Leu Leu Pro Arg
            20                  25                  30

Val Arg Leu Leu Pro Leu Leu Leu Ala Leu Ala Val Gly Ser Ala Phe
        35                  40                  45

Tyr Thr Ile Trp Ser Gly Trp His Arg Arg Thr Glu Glu Leu Pro Leu
    50                  55                  60

Gly Arg Glu Leu Arg Val Pro Leu Ile Gly Ser Leu Pro Glu Ala Arg
65                  70                  75                  80

Leu Arg Arg Val Val Gly Gln Leu Asp Pro Gln Arg Leu Trp Ser Thr
                85                  90                  95

Tyr Leu Arg Pro Leu Leu Val Val Arg Thr Pro Gly Ser Pro Gly Asn
            100                 105                 110

Leu Gln Val Arg Lys Phe Leu Glu Ala Thr Leu Arg Ser Leu Thr Ala
        115                 120                 125

Gly Trp His Val Glu Leu Asp Pro Phe Thr Ala Ser Thr Pro Leu Gly
    130                 135                 140

Pro Val Asp Phe Gly Asn Val Val Ala Thr Leu Asp Pro Arg Ala Ala
145                 150                 155                 160

Arg His Leu Thr Leu Ala Cys His Tyr Asp Ser Lys Leu Phe Pro Pro
                165                 170                 175

Gly Ser Thr Pro Phe Val Gly Ala Thr Asp Ser Ala Val Pro Cys Ala
            180                 185                 190

Leu Leu Leu Glu Leu Ala Gln Ala Leu Asp Leu Glu Leu Ser Arg Ala
        195                 200                 205

Lys Lys Gln Ala Ala Pro Val Thr Leu Gln Leu Phe Leu Asp Gly
    210                 215                 220

Glu Glu Ala Leu Lys Glu Trp Gly Pro Lys Asp Ser Leu Tyr Gly Ser
225                 230                 235                 240

Arg His Leu Ala Gln Leu Met Glu Ser Ile Pro His Ser Pro Gly Pro
                245                 250                 255

Thr Arg Ile Gln Ala Ile Glu Leu Phe Met Leu Leu Asp Leu Leu Gly
            260                 265                 270
```

```
Ala Pro Asn Pro Thr Phe Tyr Ser His Phe Pro Arg Thr Val Arg Trp
        275                 280                 285

Phe His Arg Leu Arg Ser Ile Glu Lys Arg Leu His Arg Leu Asn Leu
        290                 295                 300

Leu Gln Ser His Pro Gln Glu Val Met Tyr Phe Gln Pro Gly Glu Pro
305                 310                 315                 320

Ser Gly Ser Val Glu Asp Asp His Ile Pro Phe Leu Arg Arg Gly Val
                325                 330                 335

Pro Val Leu His Leu Ile Ser Thr Pro Phe Pro Ala Val Trp His Thr
                340                 345                 350

Pro Ala Asp Thr Glu Val Asn Leu His Pro Pro Thr Val His Asn Leu
        355                 360                 365

Cys Arg Ile Leu Ala Val Phe Leu Ala Glu Tyr Leu Gly Leu
        370                 375                 380

<210> SEQ ID NO 8
<211> LENGTH: 18
<212> TYPE: DNA
<213> ORGANISM: Artificial sequence
<220> FEATURE:
<223> OTHER INFORMATION: Synthetic nucleotide

<400> SEQUENCE: 8
cgtggctcca gtcacaag                                                   18

<210> SEQ ID NO 9
<211> LENGTH: 20
<212> TYPE: DNA
<213> ORGANISM: Artificial sequence
<220> FEATURE:
<223> OTHER INFORMATION: Synthetic oligonucletide

<400> SEQUENCE: 9
tcaaggctag cttgggctac                                                 20

<210> SEQ ID NO 10
<211> LENGTH: 473
<212> TYPE: DNA
<213> ORGANISM: Artificial sequence
<220> FEATURE:
<223> OTHER INFORMATION: PCR Fragment

<400> SEQUENCE: 10
cgtggctcca gtcacaaggc ccttctcccc acctcctccc cagtccctgt ccaccctcct     60
acctctctct tgccactagt tcctggaggc tacgttgcag tccctgtcgg caggctggca   120
tgttgaactg gacccattca cggcctcaac cccttgggg ccactggact cgggaacgt    180 ggtggccaca cttgacccag gagctgcccg tcacctcacc ctcgcctgcc attatgactc   240
taagttcttc cctccggggt tgccccccctt tgtgggggcc acagattcag ctgtgccctg   300
tgccctgctt ctggagttgg tccaggccct tgatgccatg ctgagcagaa tcaagcagca   360
ggtgaggaga aggggcgggt agtctatctc tggcccacat cctcgtttct gtctgctatg   420
ctttcccttt tgatagagg gtttcactag tatgtagccc aagctagcct tga            473

<210> SEQ ID NO 11
<211> LENGTH: 1095
<212> TYPE: DNA
<213> ORGANISM: Mus musculus

<400> SEQUENCE: 11
```

```
atgaaaccac cctcactttc caagcgccgt cttctgccgc gagtgcagtt cctgcccctg        60
ctgctgctgg cgctggctat gggcttggct ttctatatcg tctggaacag ctggcaccct       120
ggggttgagg agatgtcacg gagccgggat ctgcgggtcc cgctgatcgg aagcctttca       180
gaagccaagc tgcggctggt ggtagggcag ctggatccgc agcgtctctg gggaactttc       240
ctgcgtccct tattgattgt gcgaccccg ggtagttctg gcaatctcca agtgagaaag        300
ttcctggagg ctacgttgca gtccctgtcg gcaggctggc atgttgaact ggacccattc       360
acggcctcaa ccccctrgggg gccactggac ttcgggaacg tggtggccac acttgaccca      420
ggagctgccc gtcacctcac cctcgcctgc cattatgact ctaagttctt ccctccgggg       480 ttgccccct tgtggggc cacagattca gctgtgccct gtgccctgct tctggagttg          540
gtccaggccc ttgatgccat gctgagcaga atcaagcagc aggcagcacc ggtgaccctg       600
cagctgcttt tcttgggga ggaggcactg aaggagtggg accaaaggaa ctccctctat        660
ggctcccggc acctagctca gatcatggag tctataccac acagccctgg ccccaccag        720 atccaggcta ttgagctctt tgtcctcctc gaccttctgg gagcatccag tccgatcttc       780
ttcagtcact ccctcgcac agcccgctgg ttccagcgac tgaggagcat tgagaagcgc        840
cttcaccggc tgaacctact gcagtctcac ccccaggaag tgatgtactt ccaacccggg       900 gagcccccg gccctgtgga agatgaccac atcccttcc ttcgcagagg ggtcccggtg         960
ctccacctca ttgccacgcc cttccctgct gtgttgcaca cacctgctga caccgaggcc      1020
aacctccacc cacccactgt gcataacctg agccgcatcc ttgctgtgtt cctggccgag      1080
tacctgggac tctag                                                       1095
```

<210> SEQ ID NO 12
<211> LENGTH: 1098
<212> TYPE: DNA
<213> ORGANISM: Rattus norvegicus

<400> SEQUENCE: 12

```
atgaaaccac cctcactttc caagcgccgt cttctgccgc gggtgcagct cctgcccctg        60
ctgctgctgg cgctggccct gggcttggct ttttatatcg tctggaatag ctggcaccct       120
ggggttgagg aggtatcacg gagccgggat ctgcgggtcc cgctgatcgg aagcctttca       180
gaagccaagc tgcggcttgt ggtagggcag ctggatccac agcgtctctg gggaactttt       240
ctgcgtccct tgttgattgt acgaccccca ggtagtcctg gcaatctcca agtgagaaag       300
ttcctggagg ctacgttgca gtccctatcg gcaggctggc acgtggaact ggacccattc       360
acagcctcaa ccccctrgggg gccactggac ttcgggaacg tggtggccac ccttgaccca     420
ggagctgccc gtcacctcac cctcgcctgc cattatgact ctaagttctt ccctcctggg       480 ttaccccct tgtggggc cacagattca gccgtgccct gtgccctgct tctggagtta         540
gtccaggccc ttgatgtcat gctgagcaga atcaagcagc aggcagcacc agtgaccctg       600
cagctgctct tcttggacgg ggaggaggca ctgaaggagt ggggaccaaa ggactccctc       660
tatggttccc ggcacctagc tcagatcatg gagtctatac cgcacagccc tggccccacc       720
aggatccagg ctattgagct cttttgtcctt cttgaccttc tgggagcgcc cagtccaatc      780
ttcttcagtc acttcccccg cacagcccgc tggttccaac gactgcggag catcgagaag       840
cgccttcacc gtctgaacct actgcagtct caccccagg aagtgatgta cttccaaccc        900
ggggagcccc ctggccctgt ggaagatgac cacatccct tccttcgcag agggtcccg         960
```

```
gtgctccacc tcattgcgat gcccttccct gccgtgtggc acacacctgc tgacactgag    1020
gctaacctcc acccgcccac ggtgcacaac ctgagccgca tcctcgccgt gttcctggct    1080
gagtacctgg gtctctag                                                  1098
```

<210> SEQ ID NO 13
<211> LENGTH: 364
<212> TYPE: PRT
<213> ORGANISM: Mus musculus

<400> SEQUENCE: 13

```
Met Lys Pro Pro Ser Leu Ser Lys Arg Arg Leu Leu Pro Arg Val Gln
1               5                   10                  15

Phe Leu Pro Leu Leu Leu Ala Leu Ala Met Gly Leu Ala Phe Tyr
            20                  25                  30

Ile Val Trp Asn Ser Trp His Pro Gly Val Glu Glu Met Ser Arg Ser
        35                  40                  45

Arg Asp Leu Arg Val Pro Leu Ile Gly Ser Leu Ser Glu Ala Lys Leu
50                  55                  60

Arg Leu Val Val Gly Gln Leu Asp Pro Gln Arg Leu Trp Gly Thr Phe
65                  70                  75                  80

Leu Arg Pro Leu Leu Ile Val Arg Pro Pro Gly Ser Ser Gly Asn Leu
                85                  90                  95

Gln Val Arg Lys Phe Leu Glu Ala Thr Leu Gln Ser Leu Ser Ala Gly
            100                 105                 110

Trp His Val Glu Leu Asp Pro Phe Thr Ala Ser Thr Pro Leu Gly Pro
        115                 120                 125

Leu Asp Phe Gly Asn Val Val Ala Thr Leu Asp Pro Gly Ala Ala Arg
130                 135                 140

His Leu Thr Leu Ala Cys His Tyr Asp Ser Lys Phe Phe Pro Pro Gly
145                 150                 155                 160

Leu Pro Pro Phe Val Gly Ala Thr Asp Ser Ala Val Pro Cys Ala Leu
                165                 170                 175

Leu Leu Glu Leu Val Gln Ala Leu Asp Ala Met Leu Ser Arg Ile Lys
            180                 185                 190

Gln Gln Ala Ala Pro Val Thr Leu Gln Leu Leu Phe Leu Gly Glu Glu
        195                 200                 205

Ala Leu Lys Glu Trp Gly Pro Lys Asp Ser Leu Tyr Gly Ser Arg His
210                 215                 220

Leu Ala Gln Ile Met Glu Ser Ile Pro His Ser Pro Gly Pro Thr Arg
225                 230                 235                 240

Ile Gln Ala Ile Glu Leu Phe Val Leu Leu Asp Leu Leu Gly Ala Ser
                245                 250                 255

Ser Pro Ile Phe Phe Ser His Phe Pro Arg Thr Ala Arg Trp Phe Gln
            260                 265                 270

Arg Leu Arg Ser Ile Glu Lys Arg Leu His Arg Leu Asn Leu Leu Gln
        275                 280                 285

Ser His Pro Gln Glu Val Met Tyr Phe Gln Pro Gly Glu Pro Pro Gly
290                 295                 300

Pro Val Glu Asp Asp His Ile Pro Phe Leu Arg Arg Gly Val Pro Val
305                 310                 315                 320

Leu His Leu Ile Ala Thr Pro Phe Pro Ala Val Leu His Thr Pro Ala
                325                 330                 335

Asp Thr Glu Ala Asn Leu His Pro Pro Thr Val His Asn Leu Ser Arg
            340                 345                 350
```

Ile Leu Ala Val Phe Leu Ala Glu Tyr Leu Gly Leu
        355                 360

<210> SEQ ID NO 14
<211> LENGTH: 365
<212> TYPE: PRT
<213> ORGANISM: Rattus norvegicus

<400> SEQUENCE: 14

Met Lys Pro Pro Ser Leu Ser Lys Arg Arg Leu Leu Pro Arg Val Gln
1               5                   10                  15

Leu Leu Pro Leu Leu Leu Leu Ala Leu Ala Leu Gly Leu Ala Phe Tyr
            20                  25                  30

Ile Val Trp Asn Ser Trp His Pro Gly Val Glu Glu Val Ser Arg Ser
        35                  40                  45

Arg Asp Leu Arg Val Pro Leu Ile Gly Ser Leu Ser Glu Ala Lys Leu
    50                  55                  60

Arg Leu Val Val Gly Gln Leu Asp Pro Gln Arg Leu Trp Gly Thr Phe
65                  70                  75                  80

Leu Arg Pro Leu Leu Ile Val Arg Pro Gly Ser Pro Gly Asn Leu
            85                  90                  95

Gln Val Arg Lys Phe Leu Glu Ala Thr Leu Gln Ser Leu Ser Ala Gly
            100                 105                 110

Trp His Val Glu Leu Asp Pro Phe Thr Ala Ser Thr Pro Leu Gly Pro
            115                 120                 125

Leu Asp Phe Gly Asn Val Val Ala Thr Leu Asp Pro Gly Ala Ala Arg
        130                 135                 140

His Leu Thr Leu Ala Cys His Tyr Asp Ser Lys Phe Phe Pro Pro Gly
145                 150                 155                 160

Leu Pro Pro Phe Val Gly Ala Thr Asp Ser Ala Val Pro Cys Ala Leu
                165                 170                 175

Leu Leu Glu Leu Val Gln Ala Leu Asp Val Met Leu Ser Arg Ile Lys
            180                 185                 190

Gln Gln Ala Ala Pro Val Thr Leu Gln Leu Leu Phe Leu Asp Gly Glu
            195                 200                 205

Glu Ala Leu Lys Glu Trp Gly Pro Lys Asp Ser Leu Tyr Gly Ser Arg
    210                 215                 220

His Leu Ala Gln Ile Met Glu Ser Ile Pro His Ser Pro Gly Pro Thr
225                 230                 235                 240

Arg Ile Gln Ala Ile Glu Leu Phe Val Leu Leu Asp Leu Leu Gly Ala
                245                 250                 255

Pro Ser Pro Ile Phe Phe Ser His Phe Pro Arg Thr Ala Arg Trp Phe
            260                 265                 270

Gln Arg Leu Arg Ser Ile Glu Lys Arg Leu His Arg Leu Asn Leu Leu
        275                 280                 285

Gln Ser His Pro Gln Glu Val Met Tyr Phe Gln Pro Gly Glu Pro Pro
    290                 295                 300

Gly Pro Val Glu Asp Asp His Ile Pro Phe Leu Arg Arg Gly Val Pro
305                 310                 315                 320

Val Leu His Leu Ile Ala Met Pro Phe Pro Ala Val Trp His Thr Pro
                325                 330                 335

Ala Asp Thr Glu Ala Asn Leu His Pro Pro Thr Val His Asn Leu Ser
            340                 345                 350

Arg Ile Leu Ala Val Phe Leu Ala Glu Tyr Leu Gly Leu

<210> SEQ ID NO 15
<211> LENGTH: 31
<212> TYPE: DNA
<213> ORGANISM: Artificial sequence
<220> FEATURE:
<223> OTHER INFORMATION: Synthetic olignucleotide

<400> SEQUENCE: 15
atatctcgag tccatcgcca ccatggtgag c                              31

<210> SEQ ID NO 16
<211> LENGTH: 31
<212> TYPE: DNA
<213> ORGANISM: Artificial sequence
<220> FEATURE:
<223> OTHER INFORMATION: Synthetic oligouleotide

<400> SEQUENCE: 16
atatctcgag ttacttgtac agctcgtcca t                              31

<210> SEQ ID NO 17
<211> LENGTH: 28
<212> TYPE: DNA
<213> ORGANISM: Artificial sequence
<220> FEATURE:
<223> OTHER INFORMATION: Synthetic oligonucleotide

<400> SEQUENCE: 17
atatgaattc atgagtcccg ggagccgc                                  28

<210> SEQ ID NO 18
<211> LENGTH: 35
<212> TYPE: DNA
<213> ORGANISM: Artificial sequence
<220> FEATURE:
<223> OTHER INFORMATION: Synthetic oligonucleotide

<400> SEQUENCE: 18
atatgcggcc gcatgagtcc caggtactcg gccag                          35

<210> SEQ ID NO 19
<211> LENGTH: 28
<212> TYPE: DNA
<213> ORGANISM: Artificial sequence
<220> FEATURE:
<223> OTHER INFORMATION: Synthetic oligonucleotide

<400> SEQUENCE: 19
atatgaattc atgaaaccac cctcactt                                  28

<210> SEQ ID NO 20
<211> LENGTH: 28
<212> TYPE: DNA
<213> ORGANISM: Artificial sequence
<220> FEATURE:
<223> OTHER INFORMATION: Synthetic oligonucleotide

<400> SEQUENCE: 20
atatgaattc atgagtccgg ccagccgc                                  28

<210> SEQ ID NO 21
<211> LENGTH: 35
<212> TYPE: DNA
<213> ORGANISM: Artificial Sequence

```
<220> FEATURE:
<223> OTHER INFORMATION: Synthetic oligonucleotide

<400> SEQUENCE: 21
atatgcggcc gcatgagacc caggtactca gccag                                      35

<210> SEQ ID NO 22
<211> LENGTH: 38
<212> TYPE: DNA
<213> ORGANISM: Artificial sequence
<220> FEATURE:
<223> OTHER INFORMATION: Synthetic oligonucleotide

<400> SEQUENCE: 22
atatgcggcc gcatgctgtt ccagacgata tagaaagc                                   38

<210> SEQ ID NO 23
<211> LENGTH: 38
<212> TYPE: DNA
<213> ORGANISM: Artificial sequence
<220> FEATURE:
<223> OTHER INFORMATION: Synthetic oligonucleotide

<400> SEQUENCE: 23
atatgcggcc gcatgctatt ccagacgata taaaaagc                                   38

<210> SEQ ID NO 24
<211> LENGTH: 20
<212> TYPE: DNA
<213> ORGANISM: Artificial sequence
<220> FEATURE:
<223> OTHER INFORMATION: Synthetic olignucleotide

<400> SEQUENCE: 24
gggaggcaga cacaatcaat                                                       20

<210> SEQ ID NO 25
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 25
tctgacagct gggaatctga                                                       20

<210> SEQ ID NO 26
<211> LENGTH: 20
<212> TYPE: DNA
<213> ORGANISM: Artificial sequence
<220> FEATURE:
<223> OTHER INFORMATION: Synthetic oligonucloetide

<400> SEQUENCE: 26
ggcatggatc tgttggtctt                                                       20

<210> SEQ ID NO 27
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 27
tcagattccc agctgtcaga                                                       20
```

<210> SEQ ID NO 28
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 28
gcagcggaga ccagactca                                              19

<210> SEQ ID NO 29
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 29
aggcagcgga gaccaga                                                17

<210> SEQ ID NO 30
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 30
ggttggtggt ggttcttctc                                             20

<210> SEQ ID NO 31
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 31
ctgaattcgt tgcatgatgt g                                           21

<210> SEQ ID NO 32
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 32
cccactcagc ctgaagtctc                                             20

<210> SEQ ID NO 33
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 33
cttccgggtt aagagtgctg                                             20

<210> SEQ ID NO 34
<211> LENGTH: 20
<212> TYPE: DNA
<213> ORGANISM: Artificial sequence
<220> FEATURE:
<223> OTHER INFORMATION: Synthetic oligonucleotide

```
<400> SEQUENCE: 34
gtgccagact tcagggaaag                                              20

<210> SEQ ID NO 35
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 35
gctatgggct tggctttcta                                              20

<210> SEQ ID NO 36
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 36
caataaggga cgcaggaaag                                              20

<210> SEQ ID NO 37
<211> LENGTH: 28
<212> TYPE: DNA
<213> ORGANISM: Artificial sequence
<220> FEATURE:
<223> OTHER INFORMATION: Synthetic olignucleotide

<400> SEQUENCE: 37
atatgaattc gaggagatgt cacggagc                                     28

<210> SEQ ID NO 38
<211> LENGTH: 35
<212> TYPE: DNA
<213> ORGANISM: Artificial sequence
<220> FEATURE:
<223> OTHER INFORMATION: Synthetic oligonucleotide

<400> SEQUENCE: 38
atatatgcgg ccgcctagag tcccaggtac tcggc                             35

<210> SEQ ID NO 39
<211> LENGTH: 39
<212> TYPE: DNA
<213> ORGANISM: Artificial sequence
<220> FEATURE:
<223> OTHER INFORMATION: Synthetic oligonucletide

<400> SEQUENCE: 39
gatctgcggg tcccgctgaa cggaagcctt tcagaagcc                         39

<210> SEQ ID NO 40
<211> LENGTH: 39
<212> TYPE: DNA
<213> ORGANISM: Artificial sequence
<220> FEATURE:
<223> OTHER INFORMATION: Synthetic oligonucleotide

<400> SEQUENCE: 40
ggcttctgaa aggcttccgt tcagcgggac ccgcagatc                         39
```